(12) United States Patent
Chang et al.

(10) Patent No.: US 8,865,914 B2
(45) Date of Patent: Oct. 21, 2014

(54) FLUORESCENT PROBES FOR DETECTION OF COPPER

(71) Applicant: The Regents of the University of California, Oakland, CA (US)

(72) Inventors: Christopher J. Chang, Berkeley, CA (US); Genevieve C. Van De Bittner, Berkeley, CA (US); Tasuku Hirayama, Gifu (JP); Jefferson Chan, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/830,767

(22) Filed: Mar. 14, 2013

(65) Prior Publication Data

US 2014/0051863 A1    Feb. 20, 2014

Related U.S. Application Data

(60) Provisional application No. 61/649,512, filed on May 21, 2012.

(51) Int. Cl.
| | | |
|---|---|---|
| *C07D 311/86* | (2006.01) | |
| *C07D 307/94* | (2006.01) | |
| *C07D 403/08* | (2006.01) | |
| *C07F 7/10* | (2006.01) | |
| *C07F 5/04* | (2006.01) | |
| *C07D 311/82* | (2006.01) | |
| *A61K 49/00* | (2006.01) | |
| *C07D 209/12* | (2006.01) | |
| *C07D 207/323* | (2006.01) | |

(52) U.S. Cl.
CPC ............ *C07D 307/94* (2013.01); *C07D 311/82* (2013.01); *A61K 49/0052* (2013.01); *C07D 209/12* (2013.01); *C07D 403/08* (2013.01); *C07D 311/86* (2013.01); *C07D 207/323* (2013.01); *C07F 7/10* (2013.01); *A61K 49/0041* (2013.01); *C07F 5/04* (2013.01)
USPC ........... 548/405; 548/455; 549/391; 549/467; 556/406

(58) Field of Classification Search
None
See application file for complete search history.

(56) References Cited

PUBLICATIONS

Que, et al., Chem. Rev., 108:1517 (2008).*

* cited by examiner

*Primary Examiner* — Michael Barker
(74) *Attorney, Agent, or Firm* — Jeffry S. Mann

(57) ABSTRACT

The invention provides fluorescent sensors for the selective detection of a metal such as copper. The sensors may be considered to be derivatives of cyanine, fluorescein, rhodamine, rhodol, Tokyo green, or BODIPY. The sensors find particular use in detecting copper in cells and living animals.

20 Claims, 23 Drawing Sheets

FIG. 1A
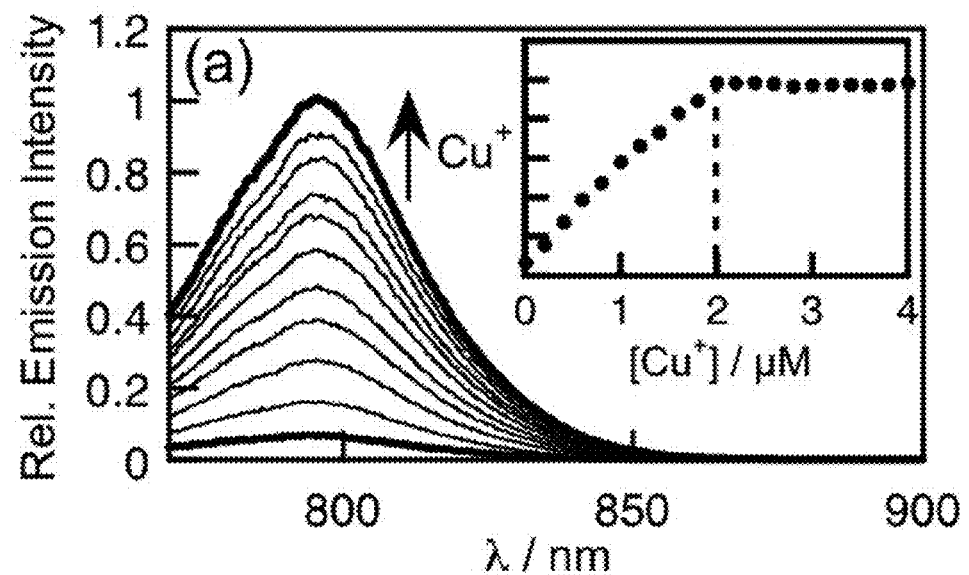
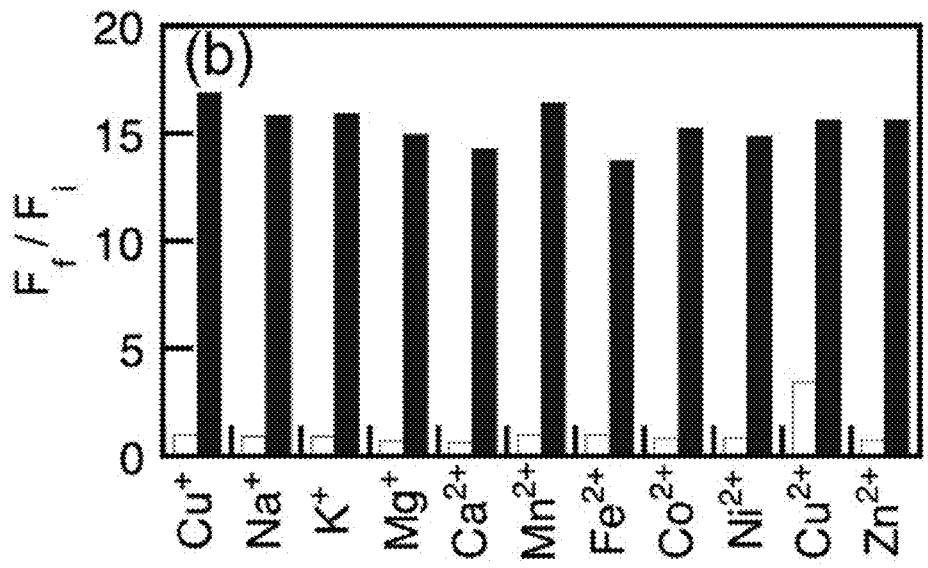
FIG. 1B

FIG. 2A
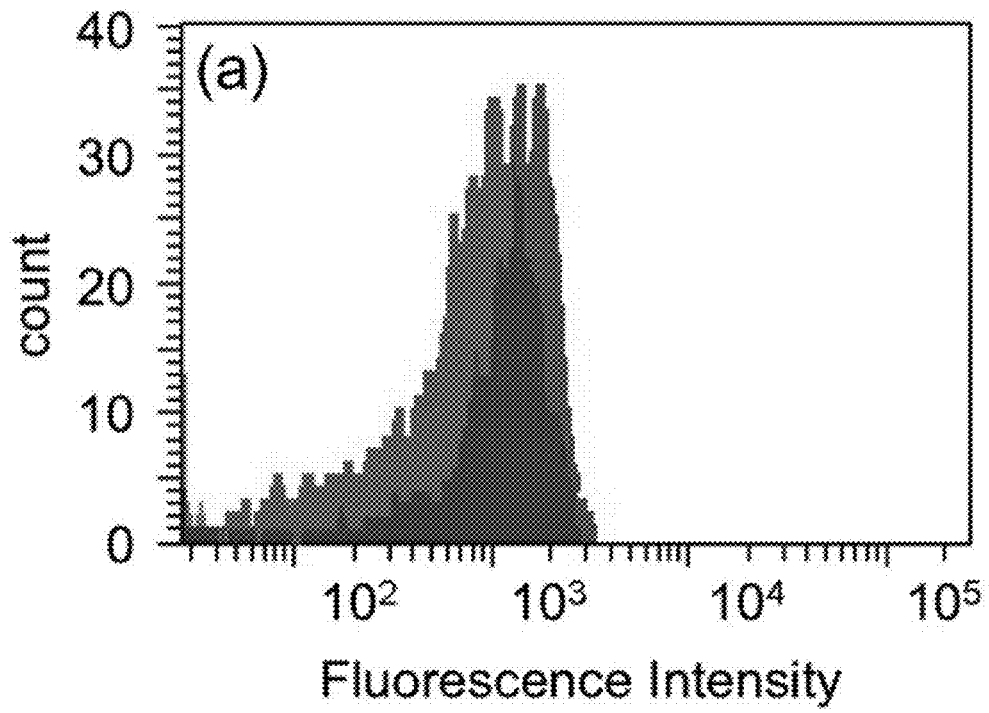
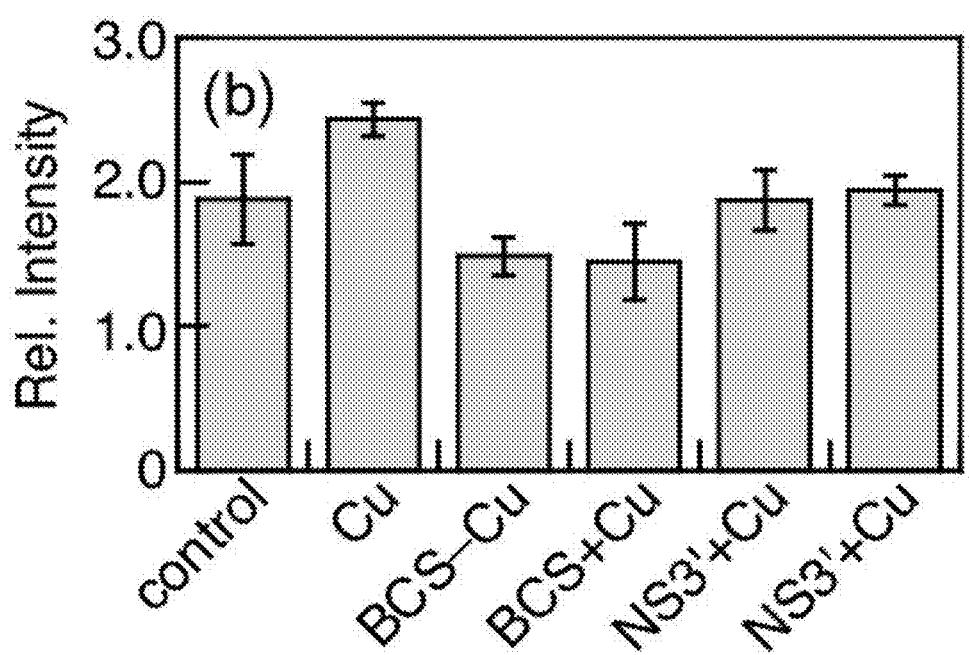
FIG. 2B scale bar : 20 μm

FIG. 4A
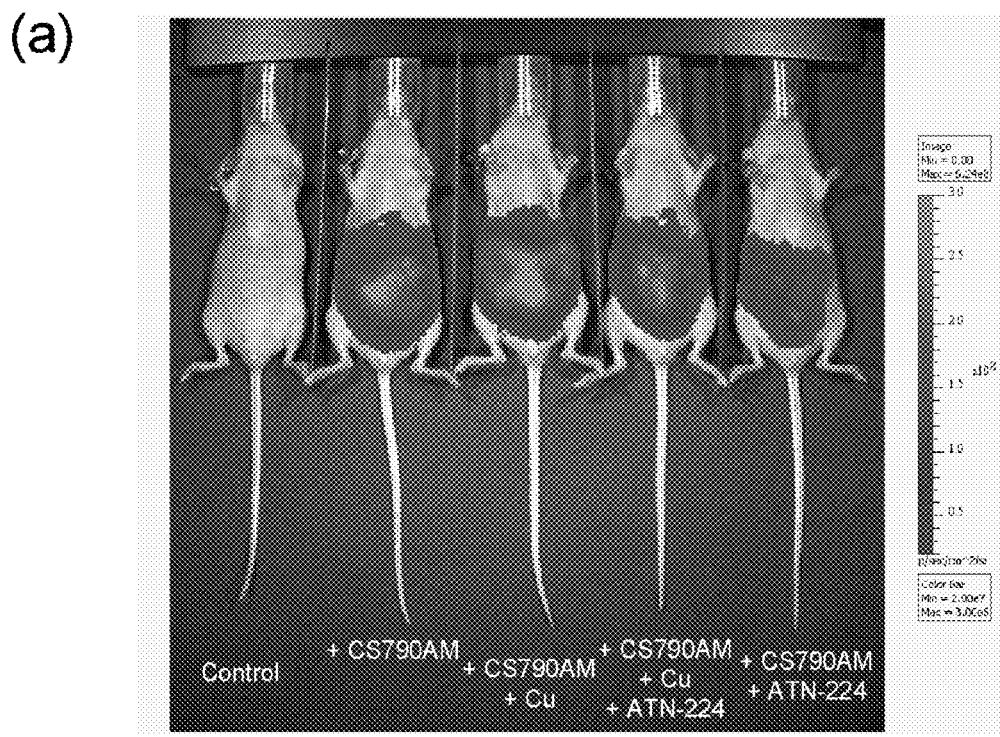
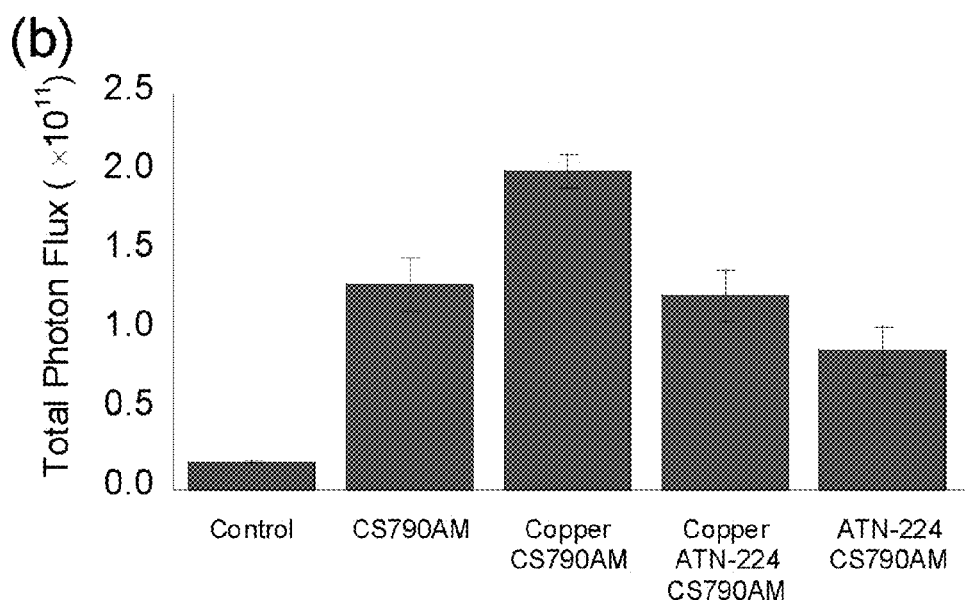
FIG. 4B

FIG. 6A
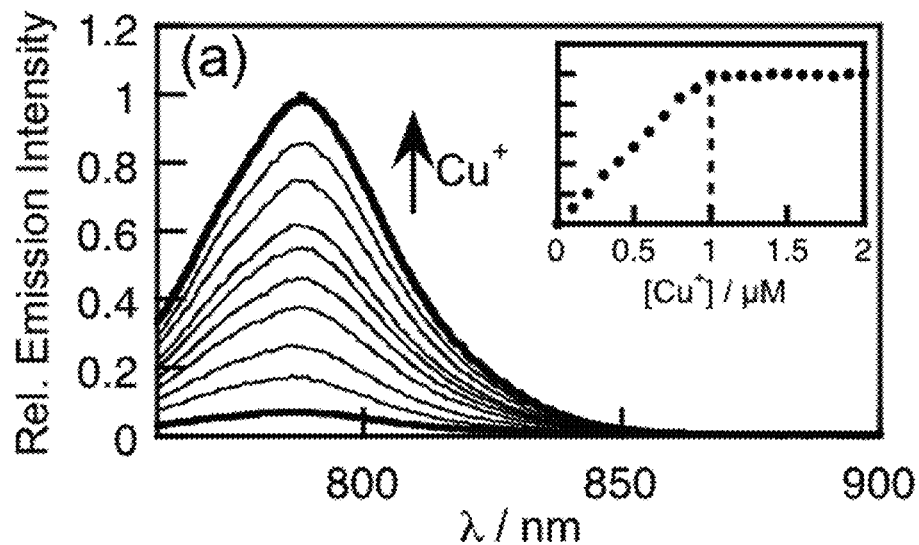
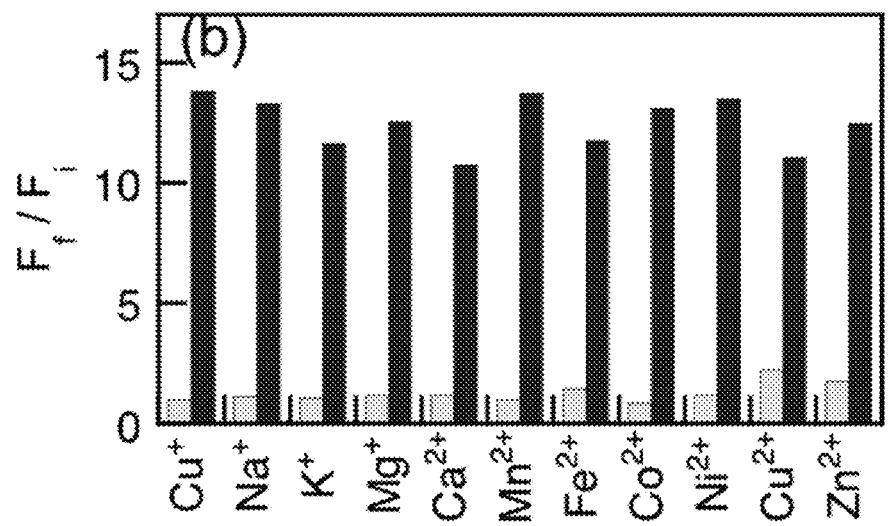
FIG. 6B

FIG. 7A
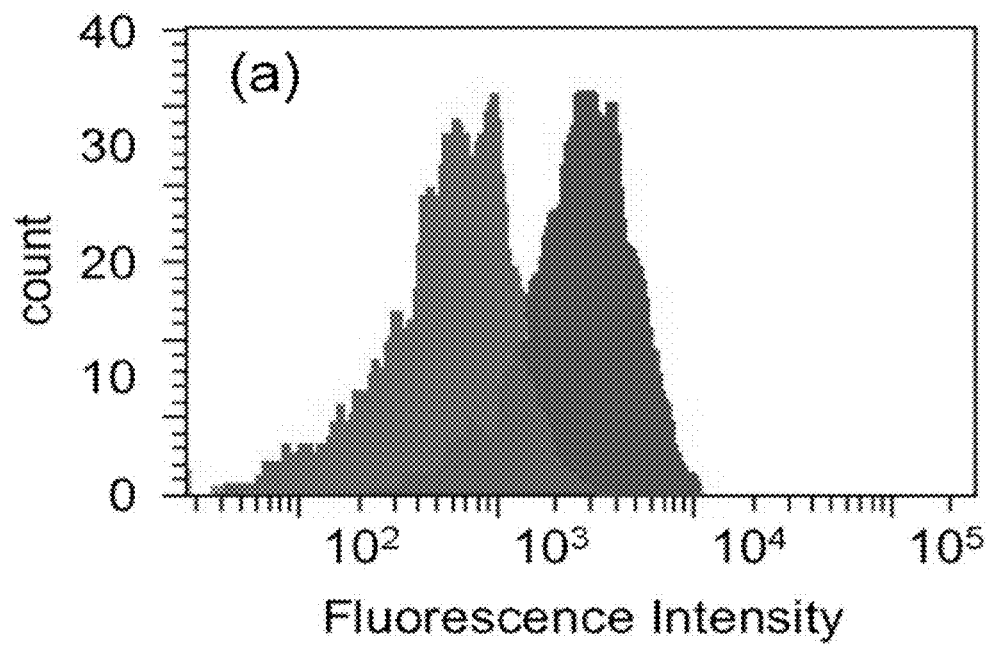
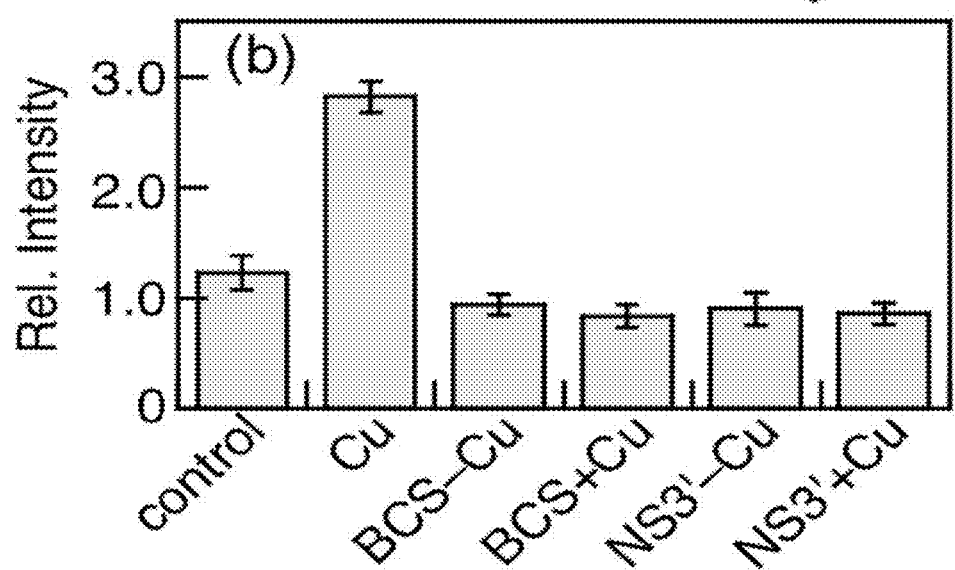
FIG. 7B scale bar : 20 μm

FIG. 9A
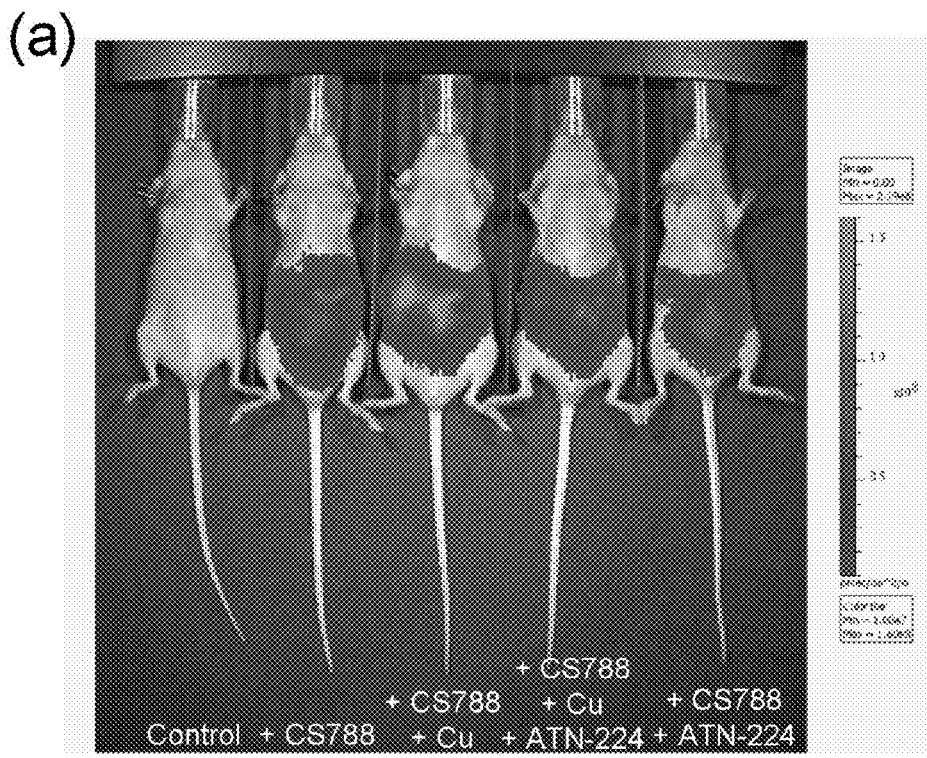
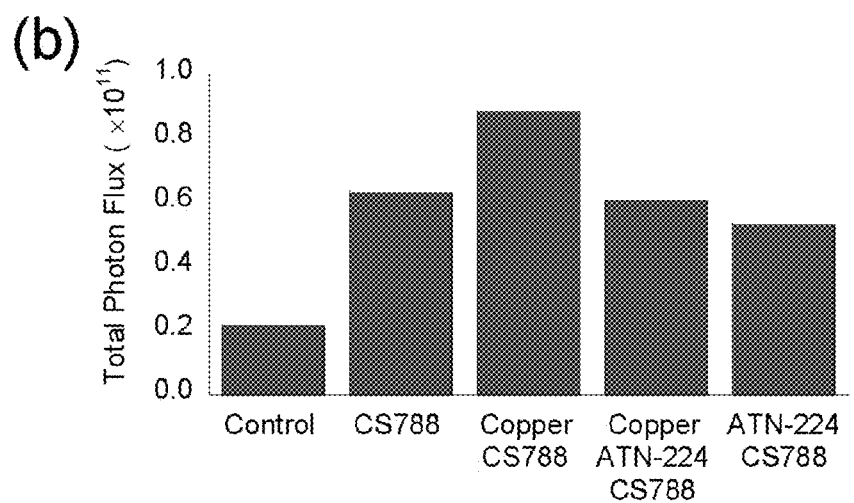
FIG. 9B

FIG. 11A  FIG. 11B  FIG. 11C
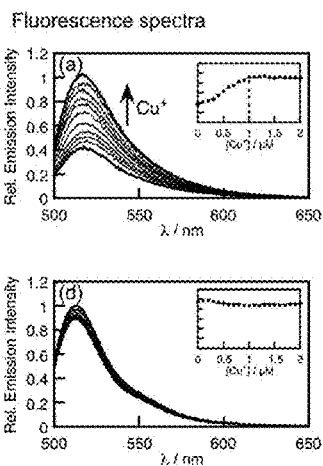
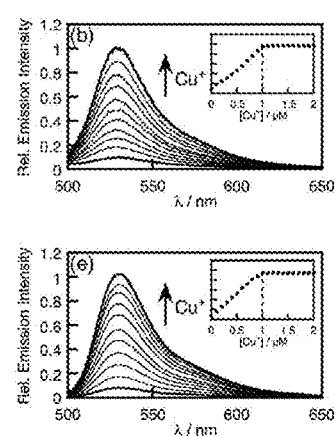
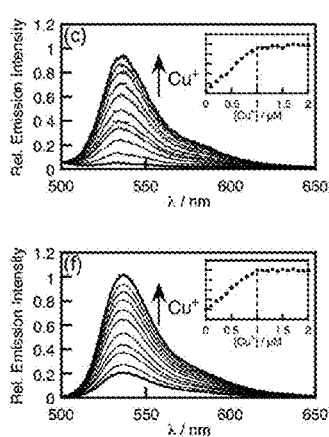
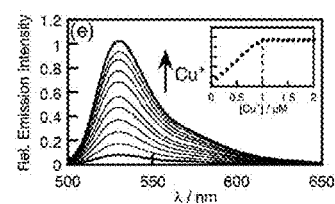
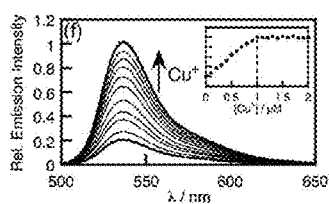
(a) TG-NS4, (b) MeTG-NS4, (c) Me2TG-NS4, (d) TG-CNS4, (e) MeTG-CNS4, (f) Me2TG-NS4
FIG. 11D  FIG. 11E  FIG. 11F FIG. 12A        FIG. 12B        FIG. 12C
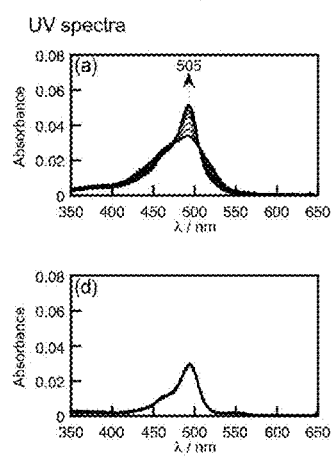
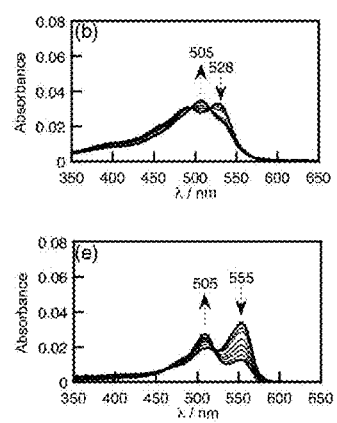
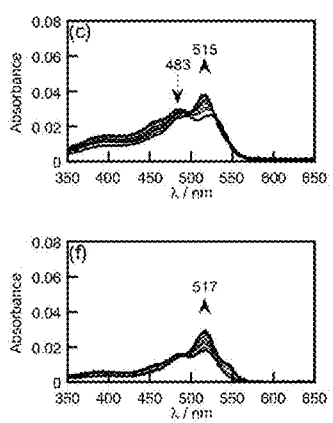
(a) TG-NS4, (b) MeTG-NS4, (c) Me2TG-NS4, (d) TG-CNS4, (e) MeTG-CNS4, (f) Me2TG-NS4
FIG. 12D        FIG. 12E        FIG. 12F FIG. 13A  FIG. 13B  FIG. 13C
Hill plot
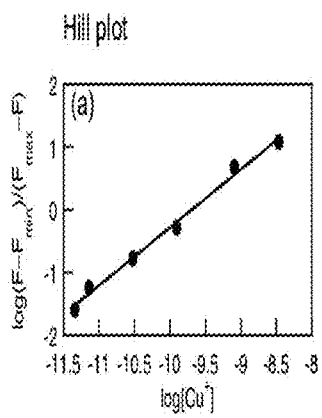
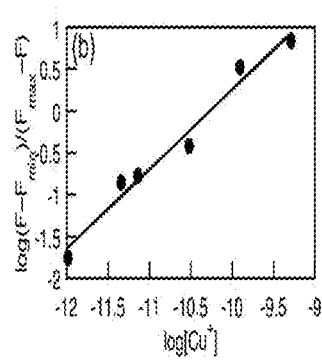
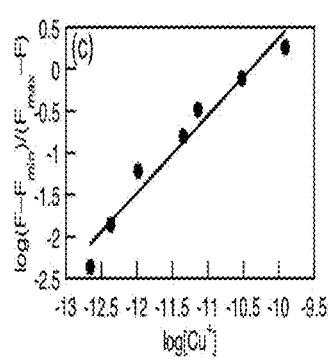
(d)
n.d.
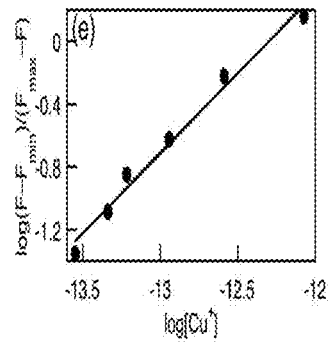
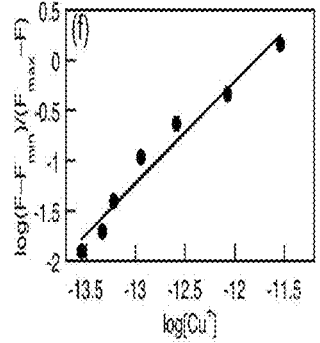
(a) TG-NS4, (b) MeTG-NS4, (c) Me2TG-NS4, (d) TG-CNS4, (e) MeTG-CNS4, (f) Me2TG-NS4
FIG. 13D  FIG. 13E  FIG. 13F FIG. 14A  FIG. 14B  FIG. 14C
Kd titration
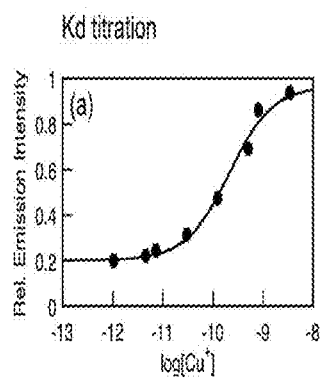
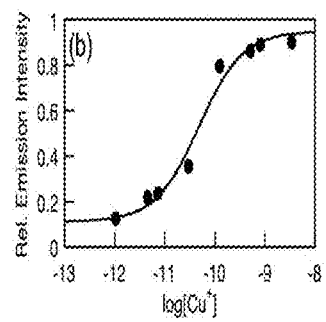
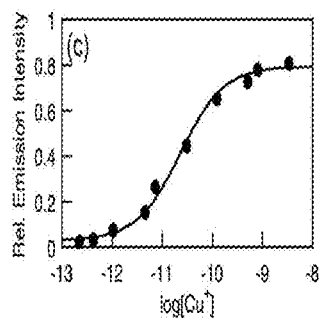
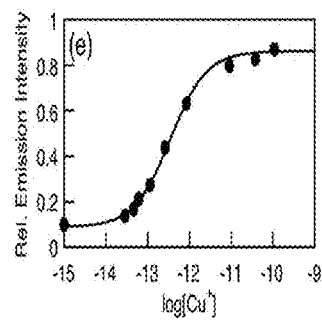
(a) TG-NS4, (b) MeTG-NS4, (c) Me2TG-NS4, (d) TG-CNS4, (e) MeTG-CNS4, (f) Me2TG-NS4
FIG. 14D  FIG. 14E  FIG. 14F pH dependency (fluo)

(a) TG-NS4, (b) MeTG-NS4, (c) Me2TG-NS4, (d) TG-CNS4, (e) MeTG-CNS4, (f) Me2TG-NS4

FIG. 16A
FIG. 16B
FIG. 16C
pKa calculation
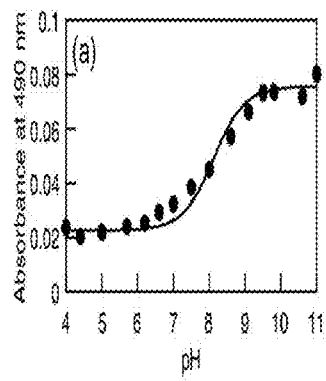
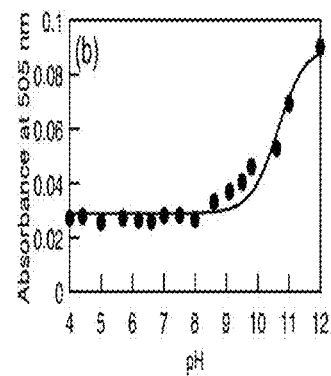
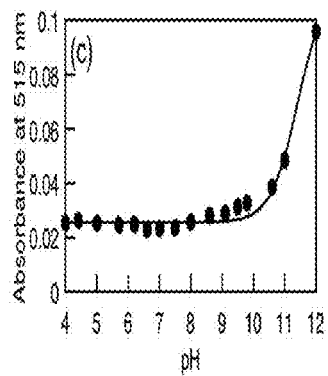
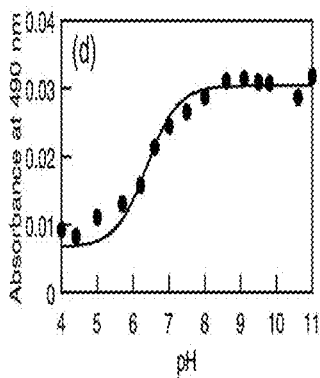
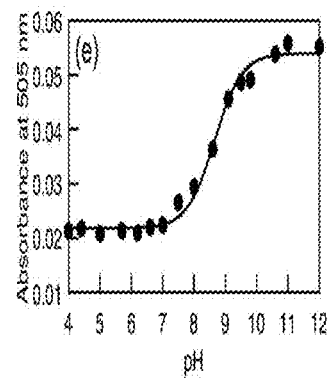
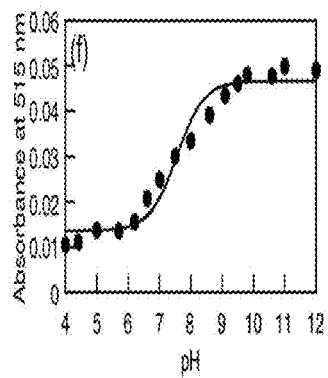
(a) TG-NS4, (b) MeTG-NS4, (c) Me2TG-NS4, (d) TG-CNS4, (e) MeTG-CNS4, (f) Me2TG-NS4
FIG. 16D
FIG. 16E
FIG. 16F FIG. 17A
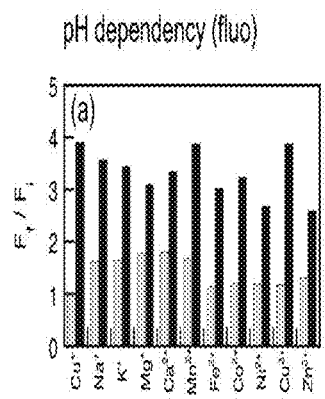
FIG. 17B
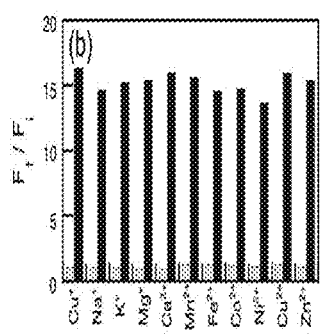
FIG. 17C
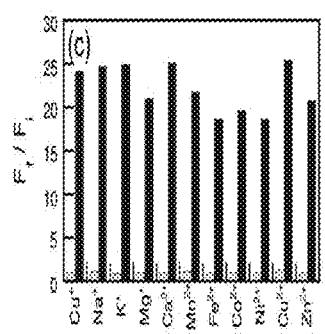
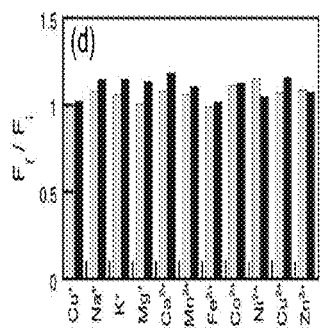
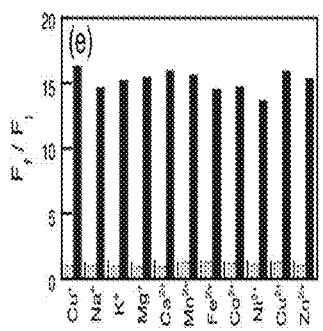
(a) TG-NS4, (b) MeTG-NS4, (c) Me2TG-NS4, (d) TG-CNS4, (e) MeTG-CNS4, (f) Me2TG-NS4
FIG. 17D    FIG. 17E    FIG. 17F FIG. 18A    FIG. 18B
Cellular imaging with MeTG-CNS4
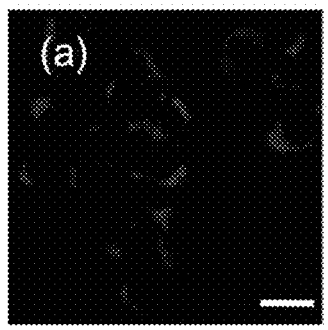
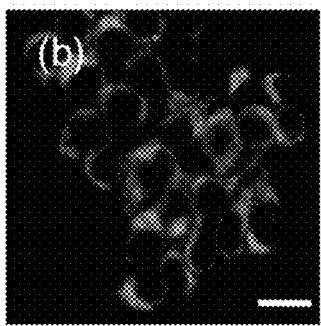
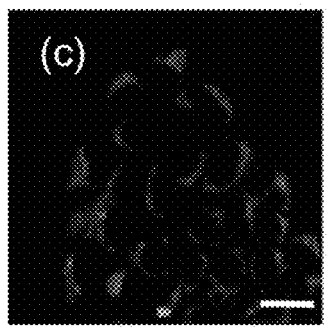
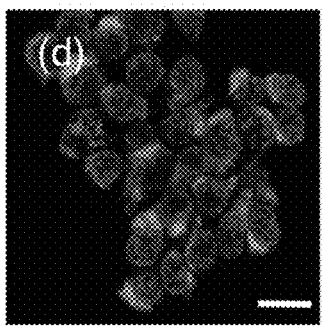
scale bar = 20 μm
(a) no Cu, (b) Cu, (c) Cu + NS3', (d) Cu (nuclear stain)
FIG. 18C    FIG. 18D (a)

(b)

FLUORESCENT PROBES FOR DETECTION OF COPPER

CROSS-REFERENCES TO RELATED APPLICATIONS

This application claims the benefit under 35 U.S.C. §119(e) of U.S. Provisional Application No. 61/649,512, filed May 21, 2012, the disclosure of which is incorporated herein by reference in its entirety for all purposes.

TECHNICAL FIELD

The field of the invention relates to fluorescent sensors for the selective detection of a metal such as copper. The sensors find particular use in detecting copper in cells and living animals.

BACKGROUND

It has been well demonstrated that copper is involved in the development and progression of many diseases, including Menkes disease, Wilson's disease, neurodegenerative diseases, anemia, heart disease, and cancer. Furthermore, copper is a well-known metal cofactor in many enzymes and is necessary for proper cellular function.

A number of copper-sensing agents are known. Zeng, L.; Miller, E. W.; Pralle, A.; Isacoff, E. Y.; Chang, C. J. "A Selective Turn-On Fluorescent Sensor for Imaging Copper in Living Cells", *J. Am. Chem. Soc.*, 2006, 128, 10-11. Miller, E. W.; Zeng, L.; Domaille, D. W.; Chang, C. J. "Preparation and Use of Coppersensor-1, a Synthetic Fluorophore for Live-Cell Copper Imaging", *Nature Protocols,* 2006, 1, 824-827. Domaille, D. W.; Zeng, L.; Chang, C. J. "Visualizing Ascorbate-Triggered Release of Labile Copper within Living Cells using a Ratiometric Fluorescent Sensor", *J. Am. Chem. Soc.,* 2010, 132, 1194-1195. Riefke, B.; Licha, K.; Semmler, W.; Nolte, D.; Ebert, B.; Rinneberg, H., In vivo characterization of cyanine dyes as contrast agents for near-infrared imaging, Proceedings of SPIE—The International Society for Optical Engineering (1996), 2927 (Optical and Imaging Techniques for Biomonitoring II), 199-208; Rajopadhye, Milind; Groves, Kevin. "Biocompatible cyanine fluorescent imaging agents and method of in vivo optical imaging", WO 2007028163 A1; Peterson, Jeffrey D.; Rajopadhye, Milind. "Viable near-infrared fluorochrome labeled cells, methods of making labeled cells and in vivo imaging methods for tracking, locating or detg. quantity of viable cells", WO 2008109832 A2; Kojima, H, "Development of near-infrared fluorescent probes for in vivo imaging", Yakugaku Zasshi, 2008, 128(11): 1653-1663.

There is a great demand for systems that can be used to detect and study copper in both cells, and more importantly, living organisms.

SUMMARY OF INVENTION

We have developed multiple molecular sensors for the detection of copper, which are based on fluorescent scaffolds. In the absence of copper, these fluorescent sensors have little to no fluorescent signal following excitation by a light source. However, in the presence of copper, these fluorescent sensors have an increase in fluorescent signal following excitation by a light source. Some of the developed fluorescent copper sensors emit light in the near-infrared region of the electromagnetic spectrum, making them ideal for in vivo imaging because they circumvent issues of autofluorescence and signal attenuation by tissue. In fact, two of these fluorescent copper sensors, Copper Sensor 788 (CS788) and Copper Sensor 790C Acetoxy Methyl Ester (CS790AM), have been used to detect changes in the level of copper in healthy mice. Use of these NIR fluorescent sensors is the first example of the use of turn-on fluorescent sensors for the detection of a metal ion in living mice. Given the success we have had with detecting copper in living mice, the most common animal model for studying human disease, we anticipate that our sensors will be useful for studying the roles that copper plays in healthy mice under various circumstances, such as dietary changes, and the roles copper plays in the development and progression of many diseases, including Menkes disease, Wilson's disease, neurodegenerative diseases, anemia, heart disease, and cancer, which are among the main causes of death and decreased quality of life in the United States. Furthermore, because our sensors are nontoxic and based on fluorescence optical imaging, they have the potential to be used in humans to help diagnose diseases or determine efficacy of treatments for various diseases.

Our fluorescent sensors are especially useful for studying copper in health and disease because they have been shown to detect endogenous levels of copper in living mice. This indicates that the copper sensors have a high sensitivity towards copper and that they will be useful for studying copper in many different contexts. Furthermore, our sensors are nontoxic and can be used to monitor individual mice over time, which means that the involvement of copper in the development of a disease state can be monitored in particular mice and can be compared between different groups of mice (e.g. older vs. younger, male vs. female).

BRIEF DESCRIPTION OF THE DRAWINGS

FIG. 1A-B. (a) Plot of fluorescence response of 1 μM CS790 upon addition of $Cu^+$ (0.1 μM increments up to 1 μM). Spectra were acquired in 20 mM HEPES, pH 7, with excitation at 760 nm. (b) Fluorescence responses of CS790 to various metal ions. Bars represent the final integrated fluorescence response over the initial integrated fluorescence response. Initial spectra were acquired in 20 mM HEPES, pH 7. White bars represent the addition of an excess of the appropriate metal ion to a solution of CS790. Concentrations of transition metals were kept at 10 μM, and those of alkali and alkali earth metals were 2 mM. Black bars represent the subsequent addition of $Cu^+$ to the solution. Excitation was provided at 760 nm.

FIG. 2A-B. (a) Flow cytometry data for HEK293 cells incubated without (left peak) and with 100 μM copper chloride for 12 h. Images were acquired after incubation with CS790AM for 15 min. (b) Relative intensities for flow cytometry data. BCS was added simultaneously with copper chloride and NS3' (tris(2-(ethylthio)ethyl)amine) was added simultaneously with CS790AM. $\lambda(ex)$=633 nm.

FIG. 4A-B. Live-mouse imaging with CS790AM. (a) Image of mice injected with DPBS, $CuCl_2$, and/or ATN-224, followed 2 hours later by injection with DPBS or CS790AM. (b) Integrated fluorescence from individual mice. Statistical analyses were performed with a two-tailed Student's t-test. $P<0.05$ (n=3) and error bars are ±s.d. All changes in signal are statistically significant, except the change between CS790AM and copper, ATN-244, and CS790AM.

FIG. 6A-B. (a) Plot of fluorescence response of 1 µM CS788 upon addition of Cu$^+$ (0.1 µM increments up to 1 µM). Spectra were acquired in 20 mM HEPES, pH 7, with excitation at 730 nm. (b) Fluorescence responses of CS788 to various metal ions. Bars represent the final integrated fluorescence response over the initial integrated fluorescence response. Initial spectra were acquired in 20 mM HEPES, pH 7. White bars represent the addition of an excess of the appropriate metal ion to a solution of CS788. Concentrations of transition metals were kept at 10 µM, and those of alkali and alkali earth metals were 2 mM. Black bars represent the subsequent addition of Cu+ to the solution. Excitation was provided at 730 nm.

FIG. 7A-B. (a) Flow cytometry data for HEK293 cells incubated without (left peak) and with 100 µM copper chloride for 12 h. Images were acquired after incubation with CS788 for 15 min. (b) Relative intensities for flow cytometry data. BCS was added simultaneously with copper chloride and NS3' was added simultaneously with CS788. λ(ex)=633 nm.

FIG. 9A-B. Live-mouse imaging with CS788. (a) Image of mice injected with DPBS, CuCl$_2$, and/or ATN-224, followed 2 hours later by injection with DPBS or CS788. (b) Integrated fluorescence from individual mice.

FIG. 11A-F. Fluorescence spectra for response of 1 µM Tokyo Green-based dyes to added Cu$^+$ (0.1 µM increments up to 1 µM).

FIG. 12A-F. Absorbance spectra for response of 1 µM Tokyo Green-based dyes to added Cu$^+$ (0.1 µM increments up to 1 µM).

FIG. 13A-F. Hill plots for Tokyo Green-based dyes.

FIG. 14A-F. Kd titrations for Tokyo Green-based dyes.

FIG. 16A-F. pKa titration by UV-vis measurements. Measurement conditions: 1 µM probe at each pH value. Absorbance value measured at indicated wavelengths.

FIG. 17A-F. Selectivity of Tokyo Green-based dyes toward Cu(I). Fluorescence responses of 1 µM dye upon addition of various metal ions (10 µM of transition metal ions and 1 mM of alkali and alkali earth metal ions). White bars: without Cu(I). Black bars: with 2 µM Cu(I).

FIG. 18A-D. Live-cell imaging of intracellular Cu$^+$ levels with MeTG-CNS4 using confocal microscopy. (a) HEK293 cells incubated with MeTG-CNS4. (b) HEK293 cells incubated with 100 µM copper chloride and stained with MeTG-CNS4. (c) HEK293 cells incubated with copper chloride, followed by addition of NS3' and MeTG-CNS4. (d) Overlay of (b) and nuclear stain.

DESCRIPTION OF EMBODIMENTS

Definitions

Figure 3A:
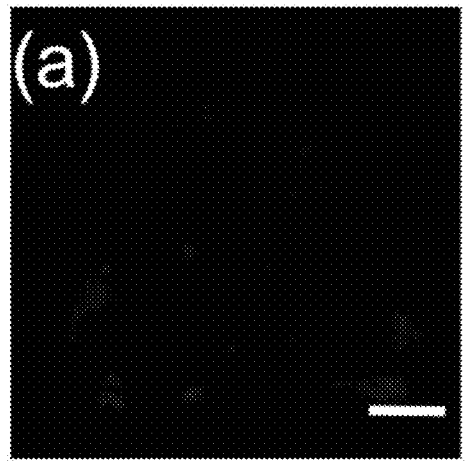
FIG. 3A-D. Live-cell imaging of intracellular $Cu^+$ levels by confocal microscopy. (a) HEK293 cells incubated with CS790AM. (b) HEK293 cells incubated with 100 μM copper chloride and stained with CS790AM. (c) HEK293 cells incubated with 100 μM copper chloride, followed by addition of a copper chelator and CS790AM. (d) Overlay of (b) and nuclear stain.
Figure 3B:
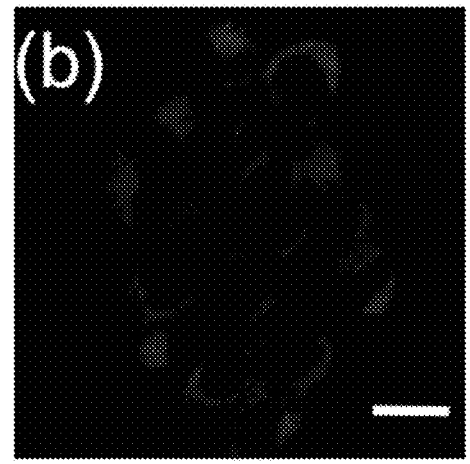
Figure 3C:
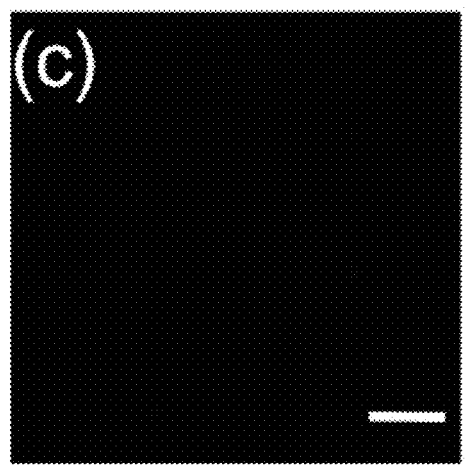
Figure 3D:
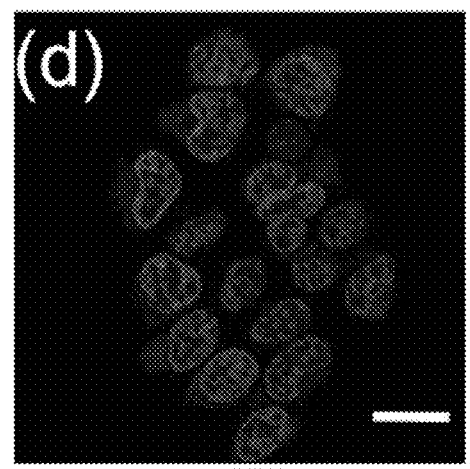
Figure 5A:
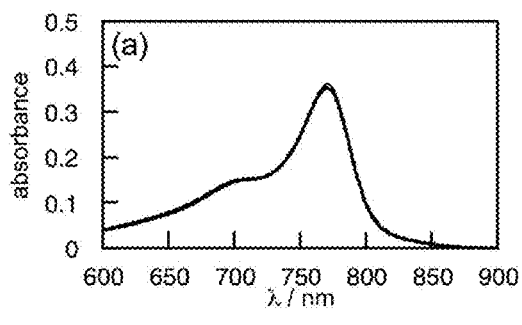
FIG. 5A-D. (a) Absorbance spectra for response of CS790 to added Cu$^+$ (0.1 µM increments up to 1 µM). (b) Fluorescence response of CS790 to Cu(I) at various pHs. White circles: without Cu(I). Black circles: with Cu(I). (c) Job's plot of CS790 and Cu(I). (d) Fluorescence response of CS790 to a Cu(I)-buffered solution. Thiourea was used as a competing ligand for Cu(I).
Figure 5B:
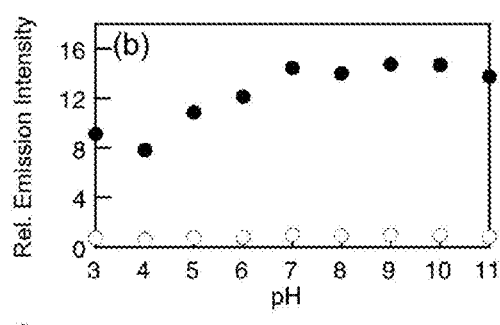
Figure 5C:
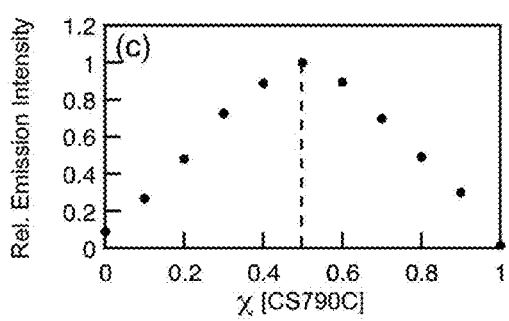
Figure 5D:
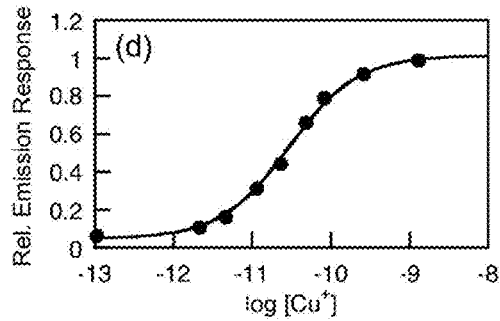
Figure 8A:
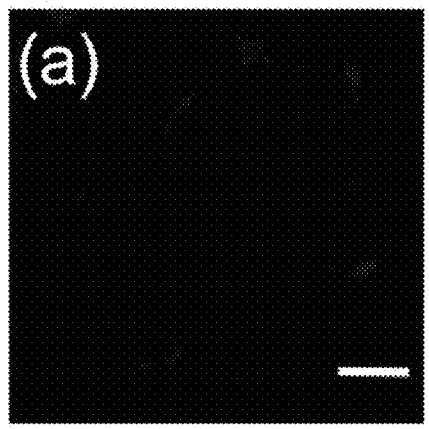
FIG. 8A-D. Live-cell imaging of intracellular Cu$^+$ levels by confocal microscopy. (a) HEK293 cells incubated with CS788. (b) HEK293 cells incubated with 100 µM copper chloride and stained with CS788. (c) HEK293 cells incubated with 100 µM copper chloride, followed by addition of a copper chelator and CS788. (d) Overlay of (b) and nuclear stain.
Figure 8B:
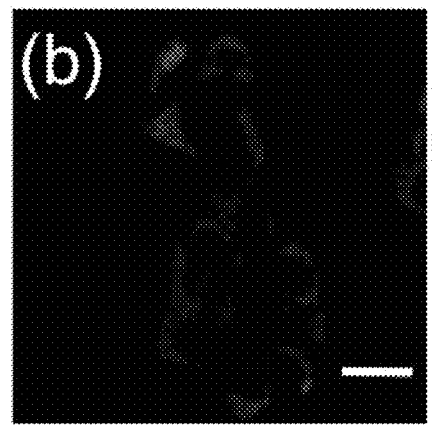
Figure 8C:
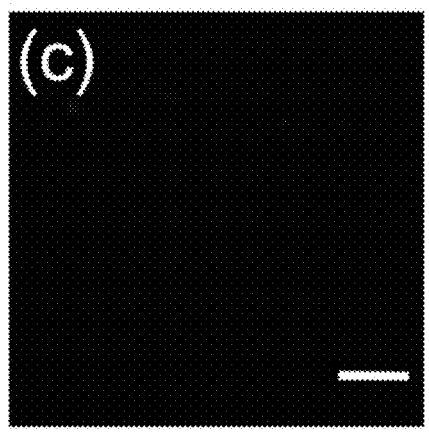
Figure 8D:
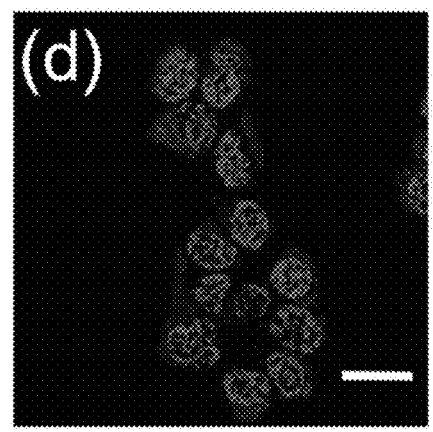
Figure 10A:
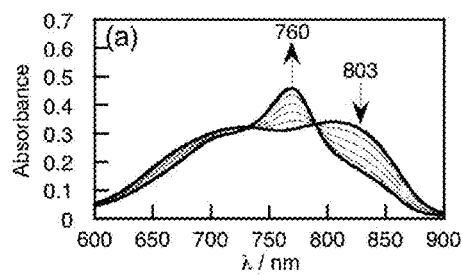
FIG. 10A-D. (a) Absorbance spectra for response of CS788 to added Cu$^+$ (0.1 µM increments up to 1 µM). (b) Fluorescence response of CS788 to Cu(I) at various pHs. White circles: without Cu(I). Black circles: with Cu(I). (c) Job's plot of CS788 and Cu(I). (d) Fluorescence response of CS788 to a Cu(I)-buffered solution. Thiourea was used as a competing ligand for Cu(I).
Figure 10B:
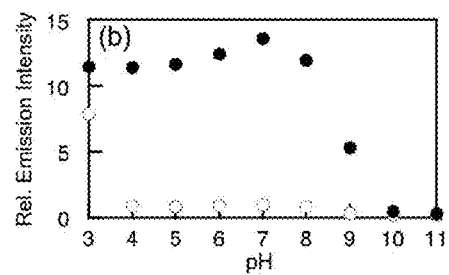
Figure 10C:
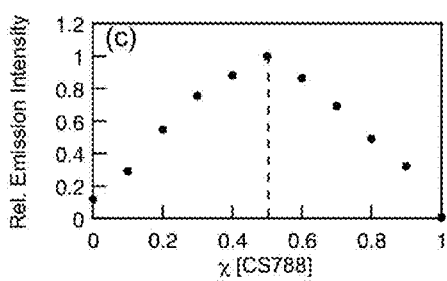
Figure 10D:
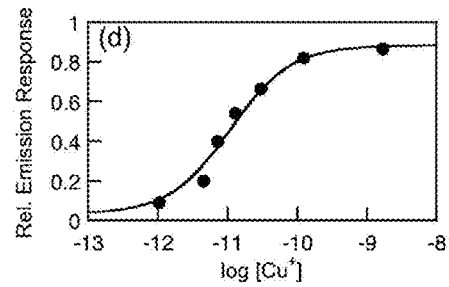
Figure 15A:
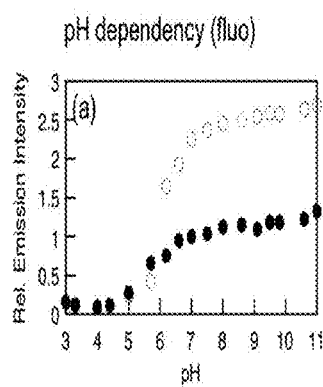
FIG. 15A-F. pH dependency of fluorescence response to Cu(I). Measurement conditions: 1 µM probe at each pH value. λ(ex)=488 nm. Fluorescence intensities at their maximum wavelength were plotted. Black circles: without Cu(I). White circles: with 2 µM Cu(I).
Figure 15B:
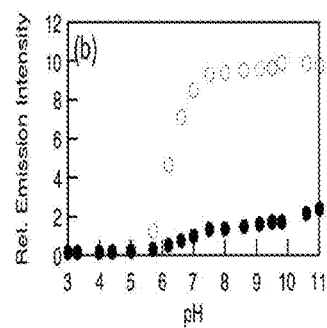
Figure 15C:
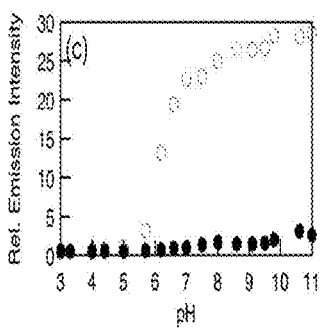
Figure 15D:
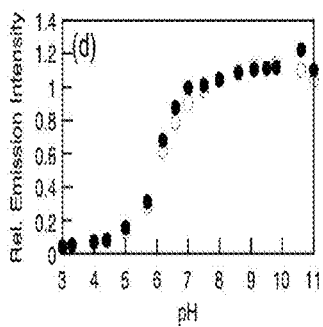
Figure 15E:
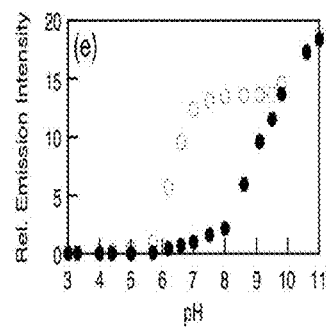
Figure 15F:
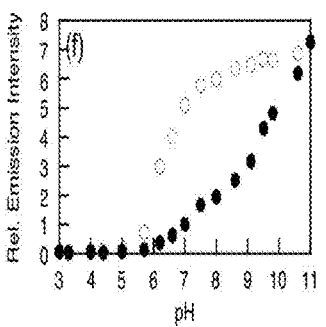
Figure 19A:
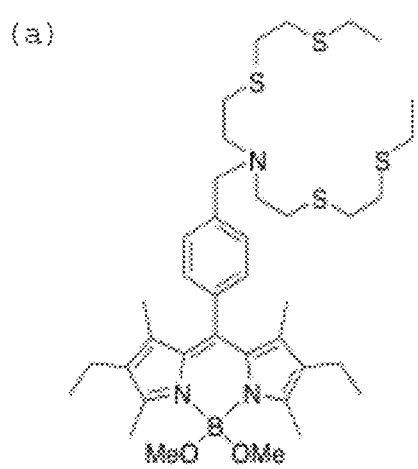
FIG. 19A-F. (a) Chemical structure of CS7. (b) Absorbance spectra for response of 2 µM CS7 to added Cu$^+$. (c) Fluorescence spectra for response of 2 µM CS7 to added Cu$^+$. (d) Kd titration for CS7. (e) Selectivity of CS7 toward Cu(I). Fluorescence responses of CS7 upon addition of various metal ions. (f) Job's plot of CS7 and Cu(I).
Figure 19B:
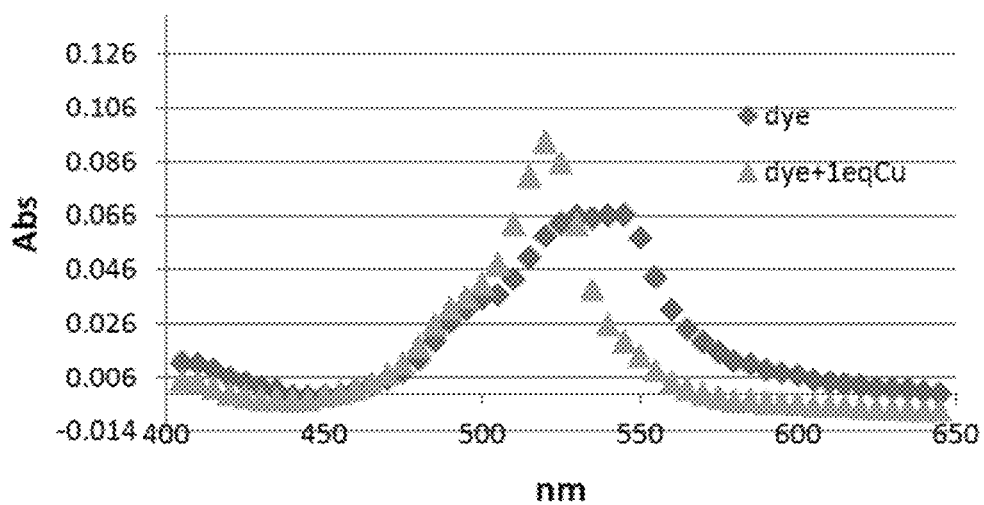
Figure 19C:
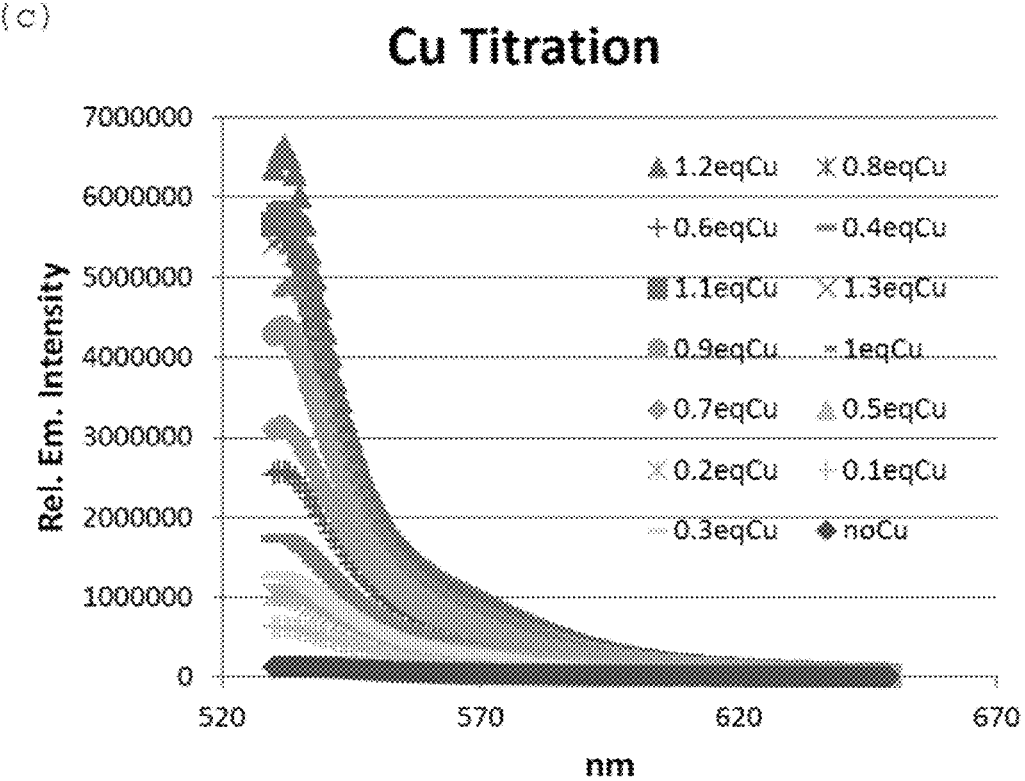
Figure 19D:
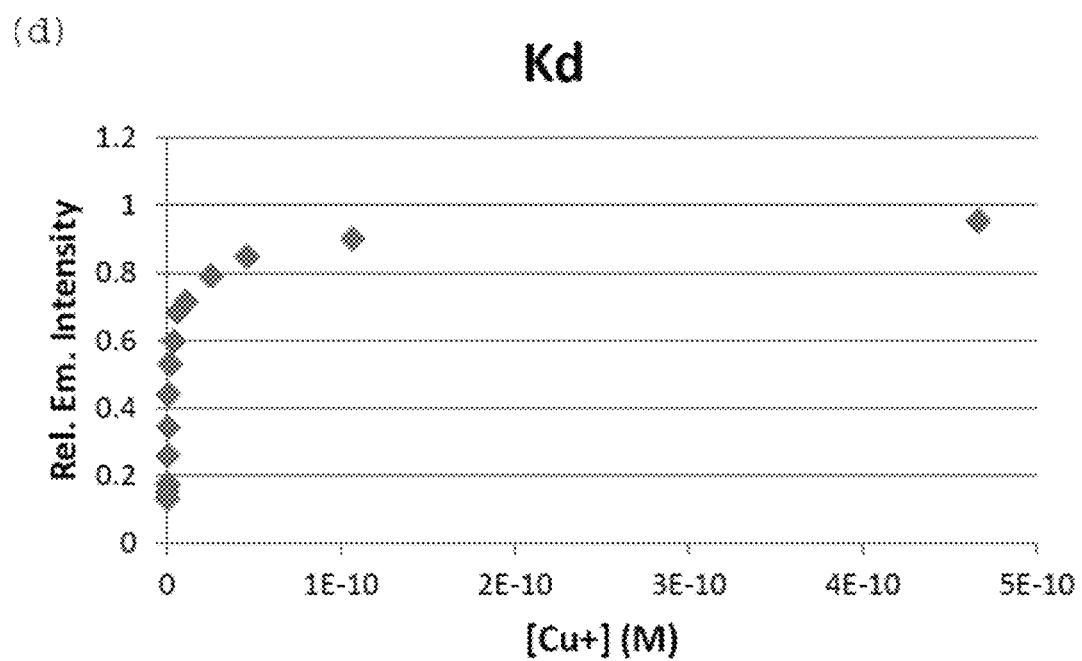
Figure 19E:
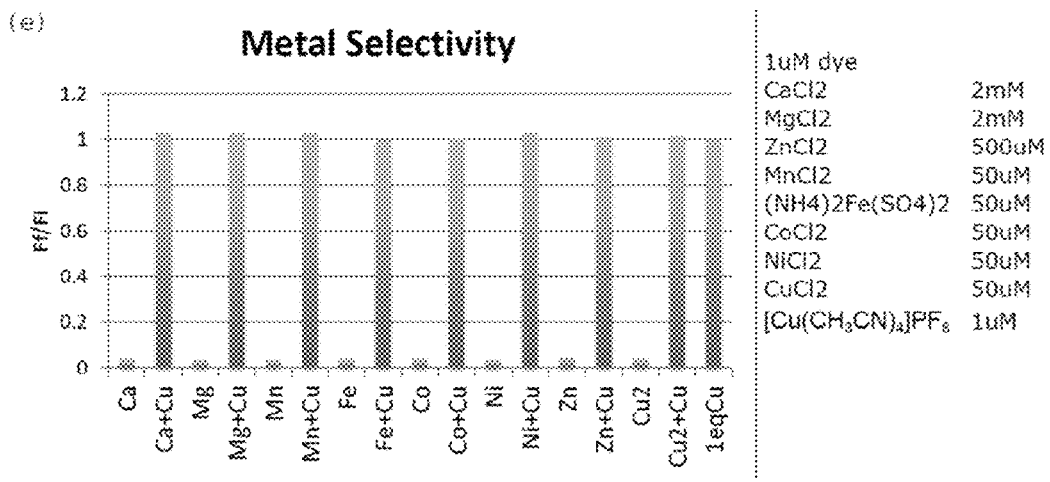
Figure 19F:
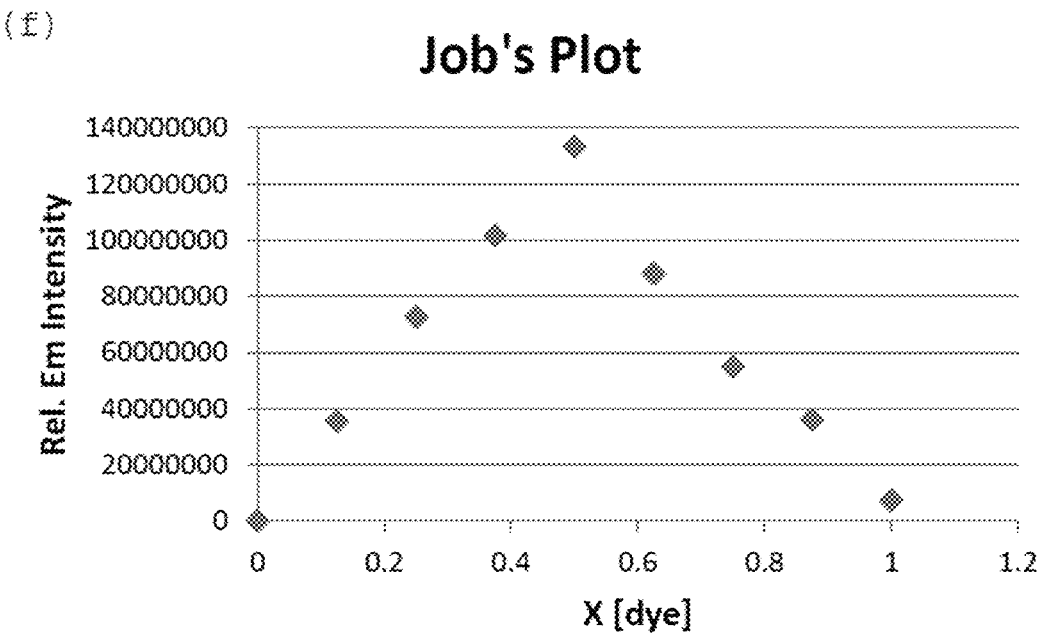
Figure 20A:
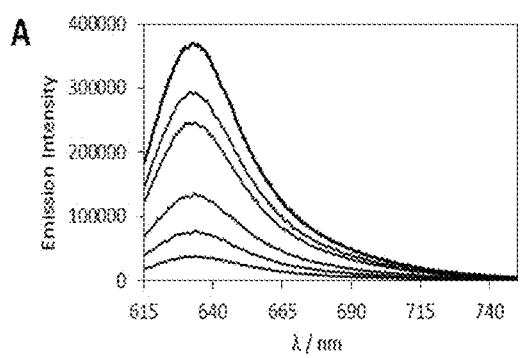
FIG. 20A-D. a) Fluorescence response of 2 µM compound 12 (of Example 6) to addition of Cu(I). Spectra acquired in 20 mM HEPES, pH 7, with excitation at 612 nm. b) Absorbance response 2 µM compound 12 (of Example 6) in 20 mM HEPES, pH 7 to addition of Cu(I). c) Fluorescence responses of compound 12 (of Example 6) to various metal ions. Bars represent the final integrated fluorescence response (Ff) over the initial integrated emission (Fi). Initial spectra were acquired in 20 mM HEPES, pH 7. Gray bars represent the addition of an excess of the appropriate metal ion (2 mM for Na$^+$, Mg$^{2+}$, K$^+$, Ca$^{2+}$, Zn$^{2+}$ and 50 µM for all other cations) to a 2 µM solution of compound 12 (of Example 6). Black bars represent the subsequent addition of 2.5 µM Cu$^+$ to the solution. Excitation was provided at 612 nm, and the emission was integrated over 615-750 nm. d) Normalized fluorescence response of 2 µM compound 12 (of Example 6) to buffered Cu$^+$ solutions for K$_d$ value determination. Thiourea was used as the competing ligand. Excitation was provided at 612 nm, and the emission was integrated over 615-750 nm. The observed K$_d$ value is 3×10$^{-13}$ M.
Figure 20B:
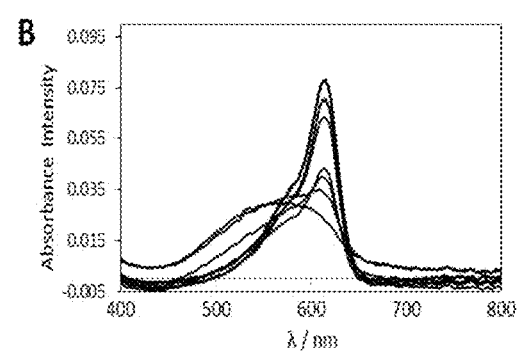
Figure 20C:
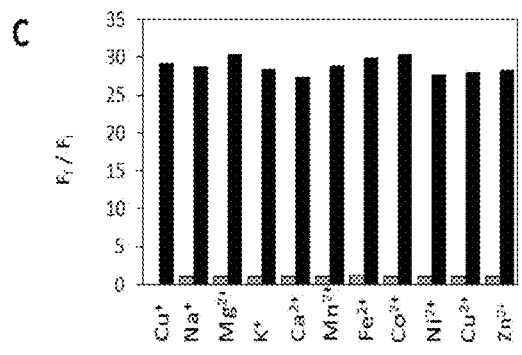
Figure 20D:
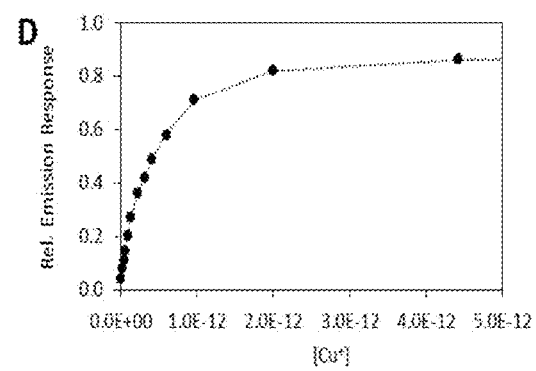

The term "alkyl", by itself or as part of another substituent, means a straight or branched chain, or cyclic hydrocarbon radical, or combination thereof, which may be fully saturated, mono- or polyunsaturated and includes mono-, di- and multivalent radicals, having the number of carbon atoms optionally designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl" can refer to "alkylene", which by itself or as part of another substituent means a divalent radical derived from an alkane, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being sometimes preferred. A "lower alkyl" or "lower alkylene" is a shorter chain alkyl or alkylene group, generally having eight or fewer carbon atoms. In some embodiments, alkyl refers to any combination (including singles) selected from C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

The term "heteroalkyl," by itself or in combination with another term, means, unless otherwise stated, a stable straight or branched chain, or combinations thereof, consisting of one or more carbon atoms and at least one heteroatom selected from the group consisting of O, N, Si and S, (preferably O, N and S) and wherein the nitrogen and sulfur atoms may optionally be oxidized and the nitrogen heteroatom may optionally be quaternized. In some embodiments, a heteroalkyl is any $C_2$-$C_{30}$ alkyl, $C_2$-$C_{25}$ alkyl, $C_2$-$C_{20}$ alkyl, $C_2$-$C_{15}$ alkyl, $C_2$-$C_{10}$ alkyl or $C_2$-$C_6$ alkyl in any of which one or more carbons are replaced by one or more heteroatoms selected from O, N, Si and S (or from O, N and S). The heteroatoms O, N, Si and S may be placed at any interior position of the heteroalkyl group or at the position at which the alkyl group is attached to the remainder of the molecule. In some embodiments, depending on whether a heteroatom terminates a chain or is in an interior position, the heteroatom may be bonded to one or more H or $C_1$, $C_2$, $C_3$, $C_4$, $C_5$ or $C_6$ alkyl according to the valence of the heteroatom. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

In some embodiments, substituents for alkyl, heteroalkyl, cycloalkyl and heterocycloalkyl are selected from the group of acceptable substituents described below.

The term "acyl" refers to a species that includes the moiety —C(O)R, where R has the meaning defined herein. Exemplary species for R include H, halogen, substituted or unsubstituted alkyl, substituted or unsubstituted aryl, substituted or unsubstituted heteroaryl, and substituted or unsubstituted heterocycloalkyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. In some embodiments, halogen refers to an atom selected from F, Cl and Br.

The term "aryl" means, unless otherwise stated, a polyunsaturated, aromatic, substituent that can be a single ring or multiple rings (preferably 1, 2 or 3 rings), which are fused together or linked covalently. In some embodiments, aryl is a 3, 4, 5, 6, 7 or 8 membered ring, which is optionally fused to one or two other 3, 4, 5, 6, 7 or 8 membered rings. The term "heteroaryl" refers to aryl groups (or rings) that contain from 1, 2, 3 or 4 heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. In some embodiments, substituents for each of the above noted aryl and heteroaryl ring systems are selected from the group of acceptable substituents described below.

In some embodiments, any of alkyl, heteroalkyl, cycloalkyl, heterocycloalkyl, aryl and heteroaryl may be substituted. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents". In some embodiments, an alkyl group substituent is selected from —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O) NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. In one embodiment, R', R", R"' and R"" are each independently selected from hydrogen and unsubstituted alkyl (e.g., $C_1$, $C_2$, $C_3$, $C_4$, $C_5$ and $C_6$ alkyl). In one embodiment, R', R", R"' and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. In one embodiment, R', R", R"' and R"" are each independently selected from hydrogen, unsubstituted alkyl, unsubstituted heteroalkyl, unsubstituted cycloalkyl, unsubstituted heterocycloalkyl, unsubstituted aryl, unsubstituted heteroaryl, alkoxy, thioalkoxy groups, and arylalkyl. When R' and R" are attached to the same nitrogen atom, they can be combined with the nitrogen atom to form a 5-, 6-, or 7-membered ring. For example, —NR'R" can include 1-pyrrolidinyl and 4-morpholinyl. In some embodiments, an alkyl group substituent is selected from substituted or unsubstituted aryl, substituted or unsubstituted heteroaryl and substituted or unsubstituted heterocycloalkyl.

Similar to the substituents described for the alkyl radical, substituents for the aryl and heteroaryl groups are generically referred to as "aryl group substituents." In some embodiments, an aryl group substituent is selected from —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N3, —CH(Ph)$_2$, fluoro($C_1$-$C_4$)alkoxy, and fluoro($C_1$-$C_4$)alkyl, in a number ranging from zero to the total number of open valences on the aromatic ring system. In some embodiments, R', R", R"' and R"" are independently selected from hydrogen and unsubstituted alkyl (e.g., $C_1$, $C_2$, $C_3$, $C_4$, $C_5$ and $C_6$ alkyl). In some embodiments, R', R", R"' and R"" are independently selected from hydrogen, substituted or unsubstituted alkyl, substituted or unsubstituted heteroalkyl, substituted or unsubstituted aryl and substituted or unsubstituted heteroaryl. In some embodiments, R', R", R"' and R"" are independently selected from hydrogen, unsubstituted alkyl, unsubstituted heteroalkyl, unsubstituted aryl and unsubstituted heteroaryl. In some embodiments, an aryl group substituent is selected from substituted or unsubstituted alkyl, substituted or unsubstituted heteroalkyl, substituted or unsubstituted heterocycloalkyl, substituted or unsubstituted aryl and substituted or unsubstituted heteroaryl.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted ($C_1$-$C_6$)alkyl.

The term "heteroatom" includes oxygen (O), nitrogen (N), sulfur (S) and silicon (Si). In some embodiments, a heteroatom is selected from N and S. In some embodiments, the heteroatom is O.

Unless otherwise specified, the symbol "R" is a general abbreviation that represents a substituent group that is selected from acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound includes more than one R, R', R", R"' and R"" group, they are each independently selected.

For groups with solvent exchangeable protons, the ionized form is equally contemplated. For example, COOH also refers to —COO$^-$ and —SO$_3$H also refers to —SO$_3^-$.

Salts (e.g., pharmaceutically acceptable salts), prodrugs, solvates, and hydrates of the compounds disclosed herein are encompassed within the scope of the invention.

For example, when compounds disclosed herein contain a primary, secondary, or tertiary amine, the corresponding protonated amines are encompassed within the scope of the invention.

The term "pharmaceutically acceptable salt" is meant to include a salt of a compound disclosed herein which is prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, or l-lysine), or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M.; Bighley, L. D.; Monkhouse, D. C. Pharmaceutical salts. *J. Pharm. Sci.* 1977, 66 (1), 1-19.). Certain specific compounds disclosed herein contain both basic and acidic functionalities that allow the compounds to be converted into either base or acid addition salts. The neutral forms of the compounds are preferably regenerated by contacting the salt with a base or acid and isolating the parent compounds in the conventional manner. The parent form of the compound differs from the various salt forms in certain physical properties, such as solubility in polar solvents.

The symbol ~~~, displayed perpendicular to a bond, indicates the point at which the displayed moiety is attached to the remainder of the molecule.

In some embodiments, the definition of terms used herein is according to IUPAC.

Embodiments

Binding-Based Probes

Provided herein are compounds that are capable of forming a chelate with a metal ion. Chelation alters the optical properties of the compound, and thus provides a useful means for detecting the metal ion.

In one aspect, the invention provides a compound having the structure:

Formula 1

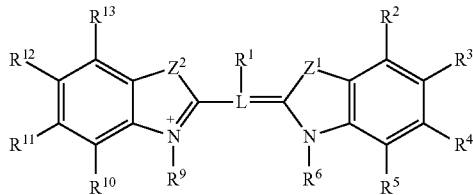

wherein L-R[1] has a structure selected from:

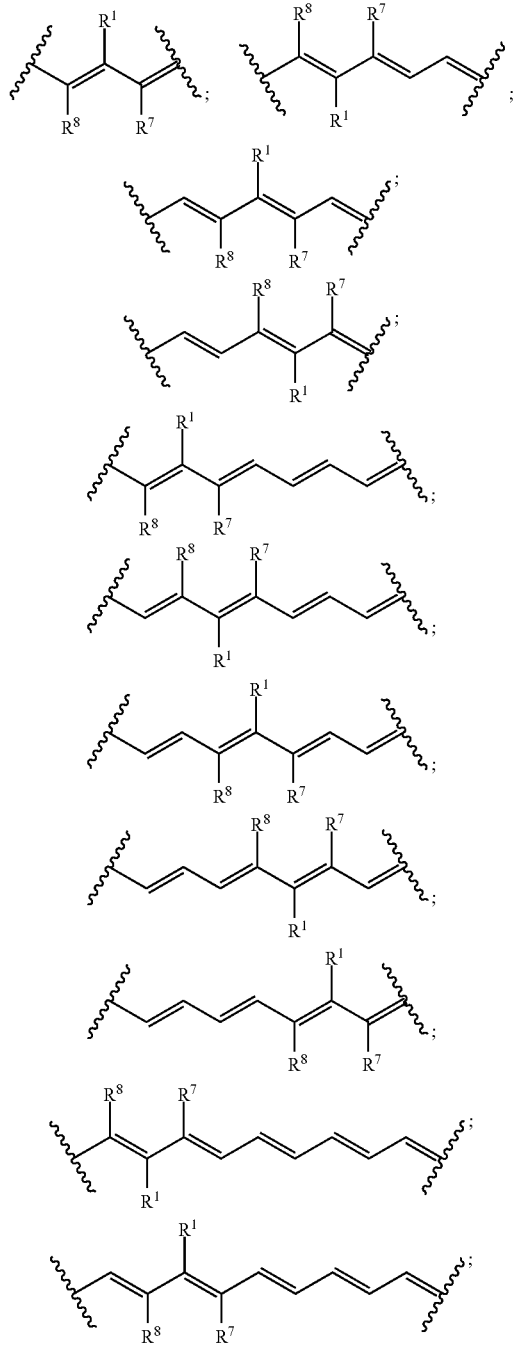

wherein R[7] and R[8] are independently selected from H, substituted or unsubstituted alkyl and substituted or unsubstituted heteroalkyl. R[7] and R[8] that are independently selected from substituted or unsubstituted alkyl and substituted or unsubstituted heteroalkyl are optionally joined to form, along with the atoms to which they are attached, a substituted or unsubstituted cycloalkyl, substituted or unsubstituted heterocycloalkyl, substituted or unsubstituted aryl or substituted or unsubstituted heteroaryl. $Z^1$ is selected from S and —C(R[14])(R[15])—, wherein R[14] and R[15] are independently selected from H, substituted or unsubstituted alkyl and substituted or unsubstituted heteroalkyl. $Z^2$ is selected from S and —C(R[50])(R[51])—, wherein R[50] and R[51] are independently selected from H, substituted or unsubstituted alkyl and substituted or unsubstituted heteroalkyl. R[2], R[3], R[4], R[5], R[10], R[11], R[12] and R[13] are independently selected from H, —SO$_3$H, substituted or unsubstituted alkyl and substituted or unsubstituted heteroalkyl; wherein one or two of R[2], R[3], R[4], R[5], R[10], R[11], R[12] and R[13] are optionally —SO$_3$H and two of R[2], R[3], R[4], R[5], R[10], R[11], R[12] and R[13] that are adjacent and that are independently selected from substituted or unsubstituted alkyl and substituted or unsubstituted heteroalkyl are optionally joined to form, along with the atoms to which they are attached, a substituted or unsubstituted aryl or substituted or unsubstituted heteroaryl. $Z^1$ and R[2] are optionally joined to form, along with the atoms to which they are attached, a substituted or unsubstituted aryl or substituted or unsubstituted heteroaryl. $Z^2$ and R[13] are optionally joined to form, along with the atoms to which they are attached, a substituted or unsubstituted aryl or substituted or unsubstituted heteroaryl. R[6] and R[9] are independently selected from substituted or unsubstituted alkyl and substituted or unsubstituted heteroalkyl. R[1] has the structure —R[1a]—R[1b]—R[1c]—R[1d]; wherein R[1a] is selected from a bond, S, O, substituted or unsubstituted alkyl and substituted or unsubstituted heteroalkyl; R[1b] is selected from a bond, substituted or unsubstituted aryl and substituted or unsubstituted heteroaryl; R[1c] is selected from a bond, substituted or unsubstituted alkyl and substituted or unsubstituted heteroalkyl; and $R^{1d}$ is selected from substituted or unsubstituted heteroalkyl and substituted or unsubstituted heterocycloalkyl.

In some embodiments, L-$R^1$ has the structure:

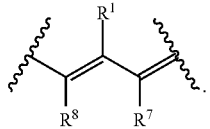

In some embodiments, L-$R^1$ has the structure:

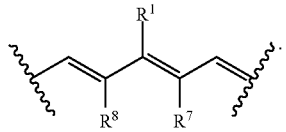

In some embodiments, L-$R^1$ has the structure:

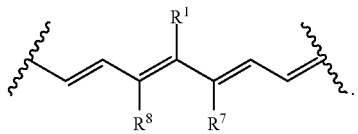

In some embodiments, $R^7$, $R^8$ or both are unsubstituted alkyl. In some embodiments, $R^7$, $R^8$ or both are independently selected from $C_1$, $C_2$, $C_3$, $C_4$, $C_5$ and $C_6$ alkyl. In some embodiments, $R^7$ and $R^8$ are joined to have the structure —(CH$_2$)$_3$—. In some embodiments, $R^7$, $R^8$ or both are H. In some embodiments, $R^7$ and $R^8$ are H.

In some embodiments, $Z^1$ is S. In some embodiments, $Z^1$ is —C($R^{14}$)($R^{15}$)—, wherein $R^{14}$, $R^{15}$ or both are H. In some embodiments, $Z^1$ is —C($R^{14}$)($R^{15}$)—, wherein $R^{14}$ and $R^{15}$ are unsubstituted alkyl. In some embodiments, $R^{14}$, $R^{15}$ or both are independently selected from $C_1$, $C_2$, $C_3$, $C_4$, $C_5$ and $C_6$ alkyl. In some embodiments, $R^{14}$ and $R^{15}$ are methyl. In some embodiments, $Z^2$ is S. In some embodiments, $Z^2$ is —C($R^{50}$)($R^{51}$)—, wherein $R^{50}$, $R^{51}$ or both are H. In some embodiments, $Z^2$ is —C($R^{50}$)($R^{51}$)—, wherein $R^{50}$ and $R^{51}$ are unsubstituted alkyl. In some embodiments, $R^{50}$, $R^{51}$ or both are independently selected from $C_1$, $C_2$, $C_3$, $C_4$, $C_5$ and $C_6$ alkyl. In some embodiments, $R^{50}$ and $R^{51}$ are methyl.

In some embodiments, $R^2$, $R^3$, $R^4$, $R^5$, $R^{10}$, $R^{11}$, $R^{12}$ and $R^{13}$ are H. In some embodiments, $R^2$, $R^4$, $R^5$, $R^{10}$, $R^{11}$ and $R^{13}$ are H; and $R^3$ and $R^{12}$ are —SO$_3$H. In some embodiments, $R^4$, $R^5$, $R^{10}$ and $R^{11}$ are H; $R^2$ and $R^3$ are joined to form, along with the atoms to which they are attached, a phenyl; and $R^{12}$ and $R^{13}$ are joined to form, along with the atoms to which they are attached, a phenyl. In some embodiments, $Z^1$ and $R^2$ are joined to form, along with the atoms to which they are attached, a phenyl. In some embodiments, $Z^2$ and $R^{13}$ are joined to form, along with the atoms to which they are attached, a phenyl.

In some embodiments, $R^6$, $R^9$ or both are substituted alkyl. In some embodiments, $R^6$, $R^9$ or both have the structure —(CH$_2$)$_m$C(O)OR$^{16}$ wherein each m is an integer independently selected from 1, 2, 3, 4, 5 and 6; and each $R^{16}$ is independently selected from H, substituted or unsubstituted alkyl and substituted or unsubstituted heteroalkyl. In some embodiments, m is 2. In some embodiments, $R^{16}$ is substituted heteroalkyl. In some embodiments, $R^{16}$ is substituted alkyl. In some embodiments, $R^{16}$ is —CH$_2$OC(O)CH$_3$. In some embodiments, $R^6$ and $R^9$ are —(CH$_2$)$_2$C(O)OCH$_2$OC(O)CH$_3$. In some embodiments, $R^6$, $R^9$ or both have the structure —(CH$_2$)$_m$SO$_3$H wherein each m is an integer independently selected from 1, 2, 3, 4, 5 and 6. In some embodiments, $R^6$, $R^9$ or both are unsubstituted alkyl. In some embodiments, $R^6$, $R^9$ or both are independently selected from $C_1$, $C_2$, $C_3$, $C_4$, $C_5$ and $C_6$ alkyl. In some embodiments, $R^6$ and $R^9$ are propyl.

In some embodiments, $R^{1a}$, $R^{1b}$, $R^{1c}$ and $R^{1d}$ are chosen according to any embodiment of any compound herein. In other words, any $R^{1a}$, $R^{1b}$, $R^{1c}$, $R^{1d}$ or combination thereof that is suitable for a compound of Formula 2 is also suitable for a compound of Formula 1.

In some embodiments, $R^{1a}$ is a bond. In some embodiments, $R^{1a}$ is O. In some embodiments, $R^{1a}$ is unsubstituted alkyl. In some embodiments, $R^{1a}$ is $C_1$, $C_2$, $C_3$, $C_4$, $C_5$ or $C_6$ alkyl. In some embodiments, $R^{1a}$ is methyl.

In some embodiments, $R^{1b}$ is a bond. In some embodiments, $R^{1b}$ is selected from unsubstituted aryl and unsubstituted heteroaryl. In some embodiments, $R^{1b}$ is unsubstituted aryl. In some embodiments, $R^{1b}$ is substituted aryl. In some embodiments, $R^{1b}$ is phenyl. In some embodiments, $R^{1b}$ is unsubstituted heteroaryl. In some embodiments, $R^{1b}$ is substituted heteroaryl. In some embodiments, $R^{1b}$ is pyridinyl. In some embodiments, $R^{1b}$ is quinolinyl. In some embodiments, $R^{1b}$ is aryl substituted with —S((CH$_2$)$_t$S)$_u$(CH$_2$)$_v$H wherein t is an integer selected from 1, 2 and 3, u is an integer selected from 1, 2 and 3, and v is an integer selected from 1 and 2. In some embodiments, $R^{1b}$ is aryl substituted with —S(CH$_2$)$_3$SCH$_3$. $R^{1b}$ is aryl substituted by a group ortho to —$R^{1c}$—$R^{1a}$.

In some embodiments, $R^{1c}$ is a bond. In some embodiments, $R^{1c}$ is unsubstituted alkyl. In some embodiments, $R^{1c}$ is $C_1$, $C_2$, $C_3$, $C_4$, $C_5$ or $C_6$ alkyl. In some embodiments, $R^{1c}$ is methyl.

In some embodiments, $R^{1d}$ is a $C_5$-$C_{21}$ alkyl or $C_5$-$C_{21}$ cycloalkyl in which at least 1, at least 2 or at least 3 of the carbon atoms are replaced with N or S. In some embodiments, $R^{1d}$ is a $C_5$-$C_{21}$ alkyl or $C_5$-$C_{21}$ cycloalkyl in which at least 1, at least 2 or at least 3 of the carbon atoms are replaced with N or S, wherein a nitrogen atom of $R^{1d}$ is bonded to $R^{1c}$. In these embodiments, any nitrogen atom not directly bonded to $R^{1c}$ may be bonded to H or $C_1$, $C_2$, $C_3$, $C_4$, $C_5$ or $C_6$ alkyl in addition to being bonded to the remainder of the $C_5$-$C_{21}$ alkyl or $C_5$-$C_{21}$ cycloalkyl. In some embodiments, a pair of adjacent C, N or S atoms are members of a ring of at least 6 members.

In some embodiments, $R^{1d}$ has the structure

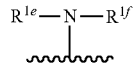

wherein $R^{1e}$ and $R^{1f}$ are independently selected from H and substituted or unsubstituted heteroalkyl, wherein both $R^{1e}$ and $R^{1f}$ are not H. In some embodiments, $R^{1e}$ and $R^{1f}$ are optionally joined to form, along with the atom to which they are attached, a ring of at least 6 members.

In some embodiments, $R^{1e}$ is unsubstituted heteroalkyl. In some embodiments, $R^{1e}$ is —((CH$_2$)$_t$S)$_u$(CH$_2$)$_v$H wherein t is an integer selected from 1, 2 and 3, u is an integer selected from 1, 2 and 3, and v is an integer selected from 1 and 2. In some embodiments, $R^{1e}$ is —(CH$_2$)$_3$SCH$_3$. In some embodiments, $R^{1e}$ is —((CH$_2$)$_2$S)$_2$(CH$_2$)CH$_3$. In some embodiments, $R^{1e}$ is —((CH$_2$)$_2$S)$_p$(CH$_2$)$_2$H wherein p is an integer selected from 1, 2 and 3.

In some embodiments, $R^{1e}$ is substituted alkyl. In some embodiments, $R^{1e}$ is $C_1$, $C_2$, $C_3$, $C_4$, $C_5$ or $C_6$ alkyl substituted with —COOH, phenyl or pyridyl. In some embodiments, $R^{1e}$ is methyl substituted with —COOH. In some embodiments, $R^{1e}$ is methyl substituted with phenyl. In some embodiments, $R^{1e}$ is methyl substituted with pyridyl.

In some embodiments, $R^{1f}$ is unsubstituted heteroalkyl. In some embodiments, $R^{1f}$ is —$((CH_2)_tS)_u(CH_2)_vH$ wherein t is an integer selected from 1, 2 and 3, u is an integer selected from 1, 2 and 3, and v is an integer selected from 1 and 2. In some embodiments, $R^{1f}$ is —$((CH_2)_2S)_2(CH_2)CH_3$. In some embodiments, $R^{1f}$ is H. In some embodiments, $R^{1f}$ is —$((CH_2)_2S)_p(CH_2)_2H$ wherein p is an integer selected from 1, 2 and 3.

In some embodiments, $R^{1f}$ is unsubstituted alkyl. In some embodiments, $R^{1f}$ is $C_1$, $C_2$, $C_3$, $C_4$, $C_5$ or $C_6$ alkyl. In some embodiments, $R^{1f}$ is methyl. In some embodiments, $R^{1f}$ is substituted alkyl. In some embodiments, $R^{1f}$ is $C_1$, $C_2$, $C_3$, $C_4$, $C_5$ or $C_6$ alkyl substituted with —COOH, phenyl or pyridyl. In some embodiments, $R^{1f}$ is methyl substituted with —COOH. In some embodiments, $R^{1f}$ is methyl substituted with phenyl. In some embodiments, $R^{1f}$ is methyl substituted with pyridyl.

In some embodiments, $R^{1d}$ has the structure

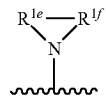

wherein $R^{1e}$—$R^{1f}$— has the structure —$((CH_2)_qS)_r(CH_2)_q$—, wherein q is an integer selected from 2 and 3 and r is an integer selected from 2, 3 and 4.

In some embodiments, $R^{1b}$ is phenyl substituted with unsubstituted heteroalkyl ortho to —$R^{1c}$—$R^{1d}$ wherein $R^{1c}$ is a bond and $R^{1d}$ is

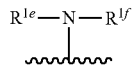

wherein $R^{1e}$ is selected from substituted or unsubstituted alkyl and substituted or unsubstituted heteroalkyl and $R^{1f}$ is selected from H, substituted or unsubstituted alkyl and substituted or unsubstituted heteroalkyl.

In some embodiments, $R^{1b}$ is phenyl substituted with —$S(CH_2)_3SCH_3$.

In some embodiments, $R^{1e}$ is unsubstituted heteroalkyl. In some embodiments, $R^{1e}$ is —$(CH_2)_3SCH_3$.

In some embodiments, $R^{1f}$ is unsubstituted alkyl. In some embodiments, $R^{1f}$ is $C_1$, $C_2$, $C_3$, $C_4$, $C_5$ or $C_6$ alkyl. In some embodiments, $R^{1f}$ is methyl. In some embodiments, $R^{1f}$ is H.

In some embodiments, $R^1$ is

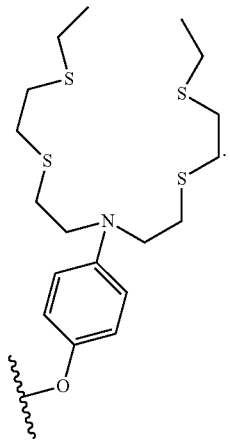 [SMILES: *Oc1ccc(N(CCSCCSCC)CCSCCSCC)cc1]

In some embodiments, $R^1$ is

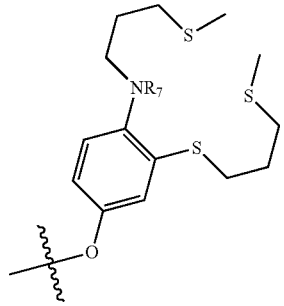

wherein $R_7$ is H.

In some embodiments, $R^{1a}$ is a bond. In some embodiments, $R^{1a}$ is unsubstituted alkyl. In some embodiments, $R^{1a}$ is $C_1$, $C_2$, $C_3$, $C_4$, $C_5$ or $C_6$ alkyl. In some embodiments, $R^{1a}$ is methyl.

In some embodiments, $R^{1b}$ is a bond.

In some embodiments, $R^{1c}$ is a bond.

In some embodiments, $R^{1d}$ has the structure

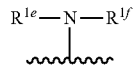

wherein $R^{1e}$ and $R^{1f}$ are independently selected from H and substituted or unsubstituted heteroalkyl, wherein both $R^{1e}$ and $R^{1f}$ are not H.

In some embodiments, $R^{1e}$ is unsubstituted heteroalkyl. In some embodiments, $R^{1e}$ is —$((CH_2)_tS)_u(CH_2)_vH$ wherein t is an integer selected from 1, 2 and 3, u is an integer selected from 1, 2 and 3, and v is an integer selected from 1 and 2. In some embodiments, $R^{1e}$ is —$((CH_2)_2S)_2(CH_2)CH_3$.

In some embodiments, V is unsubstituted heteroalkyl. In some embodiments, $R^{1f}$ is —$((CH_2)_tS)_u(CH_2)_vH$ wherein t is an integer selected from 1, 2 and 3, u is an integer selected from 1, 2 and 3, and v is an integer selected from 1 and 2. In some embodiments, $R^{1f}$ is —$((CH_2)_2S)_2(CH_2)CH_3$.

In some embodiments, $R^1$ is

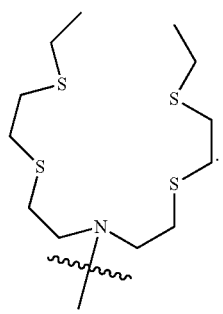 [SMILES: *N(CCSCCSCC)CCSCCSCC]

In some embodiments, $R^1$ is

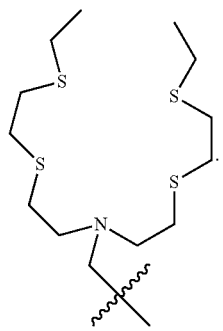 [SMILES: *CN(CCSCCSCC)CCSCCSCC]

Certain compounds according to Formula 1 have been disclosed in Hirayama, T.; Van de Bittner, G. C.; Gray, L. W.; Lutsenko, S.; Chang, C. J. Near-infrared fluorescent sensor for in vivo copper imaging in a murine Wilson disease model. *Proc. Natl. Acad. Sci. U.S.A.* 2012, 109, 2228-2233. [doi: 10.1073/pnas.1113729109]. In some embodiments, the invention provides a compound according to Formula 1, with the proviso that the compound is not a compound disclosed in Hirayama et al. *Proc. Natl. Acad. Sci. U.S.A.* 2012, 109, 2228-2233.

In some embodiments, the invention provides a compound according to Formula 1, wherein the compound is not:

(CS790)

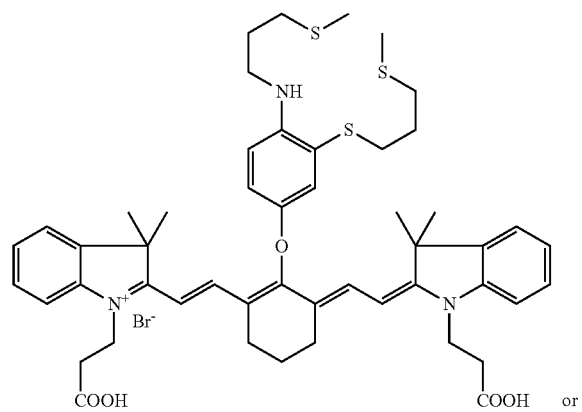

or (CS790AM)

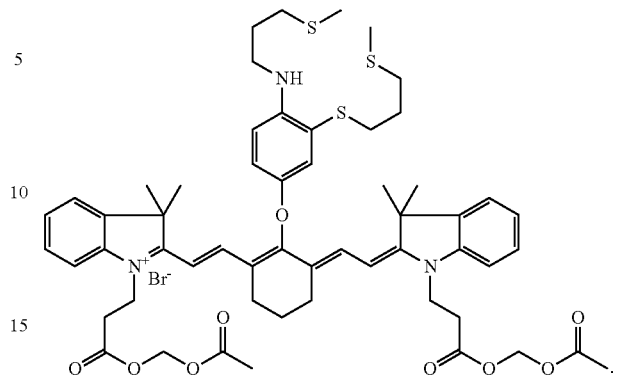

In one aspect, the invention provides a compound having the structure:

Formula 2

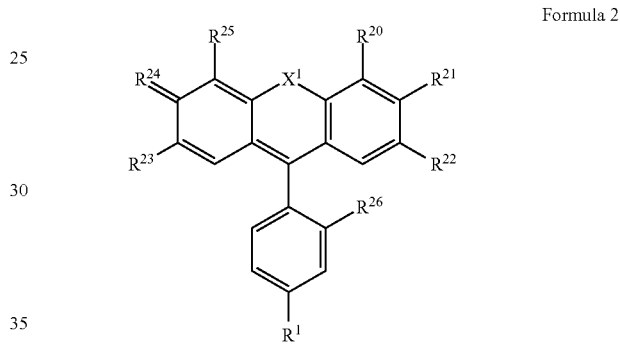

wherein $X^1$ is selected from O, $Si(R^{32})(R^{33})$, $C(R^{32})(R^{33})$, $Sn(R^{32})(R^{33})$, $B(R^{32})(R^{33})$, S, Se, and Te, wherein $R^{32}$ and $R^{33}$ are independently selected from H, substituted or unsubstituted alkyl, and substituted or unsubstituted heteroalkyl. $R^{20}$, $R^{22}$, $R^{23}$ and $R^{25}$ are independently selected from H, halogen, —$SO_3H$, substituted or unsubstituted alkyl and substituted or unsubstituted heteroalkyl. $R^{21}$ is selected from —$OR^{27}$ and —$NR^{28}R^{29}$, wherein $R^{27}$ is selected from H, substituted or unsubstituted alkyl, substituted or unsubstituted heteroalkyl, —$R^{49}$—$OR^{42}$, —$R^{49}$—$C(O)R^{45}$, —$R^{49}$—$C(O)OR^{42}$, —$R^{49}$—$C(O)N(R^{43})R^{44}$, and —$R^{49}$—$N(R^{43})C(O)R^{45}$; wherein $R^{42}$, $R^{43}$, $R^{44}$ and $R^{45}$ are independently selected from H, substituted or unsubstituted alkyl, substituted or unsubstituted heteroalkyl, substituted or unsubstituted aryl and substituted or unsubstituted heteroaryl; and $R^{49}$ is selected from a bond, substituted or unsubstituted alkyl, and substituted or unsubstituted heteroalkyl; and $R^{28}$ and $R^{29}$ are independently selected from H, substituted or unsubstituted alkyl, substituted or unsubstituted heteroalkyl, substituted or unsubstituted aryl and substituted or unsubstituted heteroaryl. $R^{28}$ and $R^{29}$ are optionally joined to form, along with the atoms to which they are attached, a substituted or unsubstituted heterocycloalkyl. $R^{28}$ and $R^{20}$ are optionally joined to form, along with the atoms to which they are attached, a substituted or unsubstituted heterocycloalkyl. $R^{29}$ and $R^{22}$ are optionally joined to form, along with the atoms to which they are attached, a substituted or unsubstituted heterocycloalkyl. $R^{24}$ is selected from O and $NR^{30}R^{31}$, wherein $R^{30}$ and $R^{31}$ are independently selected from H, substituted or unsubstituted alkyl, substituted or unsubstituted heteroalkyl, substituted or unsubstituted aryl and substituted or unsubstituted heteroaryl. $R^{30}$ and $R^{31}$ are optionally joined to form, along with the atoms to which they are attached, a substituted or unsubstituted heterocycloalkyl. $R^{31}$ is optionally present. $R^{30}$ and $R^{25}$ or $R^{30}$ and $R^{23}$ are optionally joined to form, along with the atoms to which they are attached, a substituted or unsubstituted heterocycloalkyl. $R^{31}$ and $R^{23}$ are optionally joined to form, along with the atoms to which they are attached, a substituted or unsubstituted heterocycloalkyl. $R^{26}$ is selected from H, —COOH, substituted or unsubstituted alkyl and substituted or unsubstituted heteroalkyl. $R^1$ is as defined herein.

In some embodiments, $X^1$ is O. In some embodiments, $X^1$ is $Si(R^{32})(R^{33})$. In some embodiments, $X^1$ is $C(R^{32})(R^{33})$. In some embodiments, $X^1$ is $Sn(R^{32})(R^{33})$. In some embodiments, $X^1$ is $B(R^{32})(R^{33})$. In some embodiments, $X^1$ is S. In some embodiments, $X^1$ is Se. In some embodiments, $X^1$ is Te. In some embodiments, $R^{32}$, $R^{33}$ or both are unsubstituted alkyl. In some embodiments, $R^{32}$, $R^{33}$ or both are independently selected from $C_1$, $C_2$, $C_3$, $C_4$, $C_5$ and $C_6$ alkyl. In some embodiments, $R^{32}$, $R^{33}$ or both are methyl. In some embodiments, $R^{32}$ and $R^{33}$ are methyl.

In some embodiments, $R^{21}$ is —OH. In some embodiments, $R^{21}$ is —$OR^{27}$ wherein $R^{27}$ is unsubstituted alkyl. In some embodiments, $R^{27}$ is $C_1$, $C_2$, $C_3$, $C_4$, $C_5$ or $C_6$ alkyl. In some embodiments, $R^{27}$ is methyl. In some embodiments, $R^{21}$ is —$OR^{27}$ wherein $R^{27}$ is substituted alkyl. In some embodiments, $R^{27}$ is substituted $C_1$, $C_2$, $C_3$, $C_4$, $C_5$ or $C_6$ alkyl. In some embodiments, $R^{27}$ is —$CH_2COOH$. In some embodiments, $R^{27}$ is selected from $R^{49}$—$OR^{42}$, —$R^{49}$—$C(O)R^{45}$, —$R^{49}$—$C(O)OR^{42}$, —$R^{49}$—$C(O)N(R^{43})R^{44}$, and —$R^{49}$—$N(R^{43})C(O)R^{45}$; wherein $R^{42}$, $R^{43}$, $R^{44}$ and $R^{45}$ are independently selected from H, substituted or unsubstituted alkyl, substituted or unsubstituted heteroalkyl, substituted or unsubstituted aryl and substituted or unsubstituted heteroaryl; and $R^{49}$ is selected from a bond, substituted or unsubstituted alkyl, and substituted or unsubstituted heteroalkyl. In some embodiments, $R^{49}$ is a bond. In some embodiments, $R^{49}$ is unsubstituted alkyl. In some embodiments, $R^{49}$ is selected from $C_1$, $C_2$, $C_3$, $C_4$, $C_5$ and $C_6$ alkyl. In some embodiments, $R^{49}$ is methyl. In some embodiments, $R^{27}$ is —$R^{49}$—$C(O)OR^{42}$, wherein $R^{42}$ is H. In some embodiments, $R^{21}$ is $NR^{28}R^{29}$ wherein $R^{28}$, $R^{29}$ or both are unsubstituted alkyl. In some embodiments, $R^{28}$, $R^{29}$ or both are independently selected from $C_1$, $C_2$, $C_3$, $C_4$, $C_5$ and $C_6$ alkyl. In some embodiments, $R^{28}$, $R^{29}$ or both are methyl. In some embodiments, $R^{28}$ and $R^{29}$ are methyl. In some embodiments, $R^{28}$ and $R^{20}$ are joined to form, along with the atoms to which they are attached, a substituted or unsubstituted heterocycloalkyl; and $R^{29}$ and $R^{22}$ are joined to form, along with the atoms to which they are attached, a substituted or unsubstituted heterocycloalkyl.

In some embodiments, $R^{21}$ is

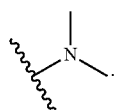

In some embodiments, $R^{21}$ is

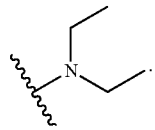

In some embodiments, $R^{21}$ is

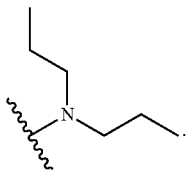

In some embodiments, $R^{21}$ is

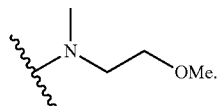 [SMILES: *N(C)CCOC]

In some embodiments, $R^{21}$ is

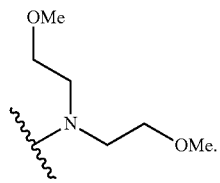 [SMILES: *N(CCOC)CCOC]

In some embodiments, $R^{21}$ is

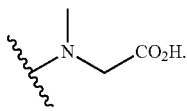

In some embodiments, $R^{21}$ is

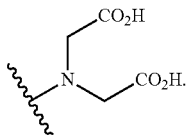 [SMILES: *N(CC(=O)O)CC(=O)O]

In some embodiments, $R^{21}$ is

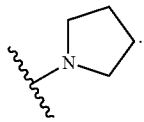

In some embodiments, $R^{21}$ is

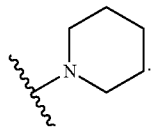 [SMILES: *N1CCCCC1 ; "."]

In some embodiments, $R^{21}$ is

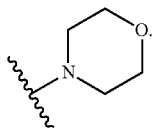

In some embodiments, $R^{21}$ is

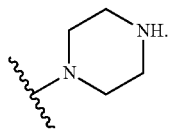 [SMILES: *N1CCNCC1]

In some embodiments, $R^{21}$ is

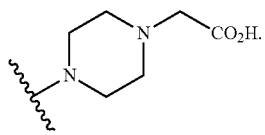 [SMILES: *N1CCN(CC(=O)O)CC1]

In some embodiments, $R^{21}$ is

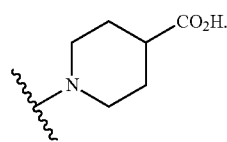 [SMILES: *N1CCC(C(=O)O)CC1]

In some embodiments, $R^{24}$ is O. In some embodiments, $R^{24}$ is $NR^{30}R^{31}$ wherein $R^{30}$, $R^{31}$ or both are unsubstituted alkyl. In some embodiments, $R^{30}$, $R^{31}$ or both are independently selected from $C_1$, $C_2$, $C_3$, $C_4$, $C_5$ and $C_6$ alkyl. In some embodiments, $R^{30}$, $R^{31}$ or both are methyl. In some embodiments, $R^{30}$ and $R^{31}$ are methyl. In some embodiments, $R^{30}$, $R^{31}$ or both are H. In some embodiments, $R^{30}$ is H and $R^{31}$ is not present. In some embodiments, $R^{30}$ is selected from substituted or unsubstituted alkyl and substituted or unsubstituted heteroalkyl; and $R^{31}$ is not present. In some embodiments, $R^{30}$ and $R^{25}$ are joined to form, along with the atoms to which they are attached, a substituted or unsubstituted heterocycloalkyl; and $R^{31}$ and $R^{23}$ are joined to form, along with the atoms to which they are attached, a substituted or unsubstituted heterocycloalkyl.

In some embodiments, $R^{26}$ is H. In some embodiments, $R^{26}$ is unsubstituted alkyl. In some embodiments, $R^{26}$ is selected from $C_1$, $C_2$, $C_3$, $C_4$, $C_5$ and $C_6$ alkyl. In some embodiments, $R^{26}$ is methyl. In some embodiments, $R^{26}$ is substituted alkyl. In some embodiments, $R^{26}$ is selected from substituted $C_1$, $C_2$, $C_3$, $C_4$, $C_5$ and $C_6$ alkyl. In some embodiments, $R^{26}$ is $-CH_2OH$. In some embodiments, $R^{26}$ is $-COOH$.

In some embodiments, $R^{20}$, $R^{22}$, $R^{23}$ and $R^{25}$ are independently selected from H and unsubstituted alkyl. In some embodiments, $R^{20}$, $R^{22}$, $R^{23}$ and $R^{25}$ are independently selected from H and $C_1$, $C_2$, $C_3$, $C_4$, $C_5$ and $C_6$ alkyl. In some embodiments, $R^{20}$, $R^{22}$, $R^{23}$ and $R^{25}$ are independently selected from H and methyl. In some embodiments, $R^{20}$, $R^{22}$, $R^{23}$ and $R^{25}$ are H. In some embodiments, $R^{20}$, $R^{22}$, $R^{23}$ and $R^{25}$ are methyl. In some embodiments, $R^{20}$ and $R^{25}$ are the same. In some embodiments, $R^{22}$ and $R^{23}$ are the same. In some embodiments, $R^{20}$ and $R^{25}$ are methyl and $R^{22}$ and $R^{23}$ are H. In some embodiments, $R^{20}$ and $R^{25}$ are H and $R^{22}$ and $R^{23}$ are methyl. In some embodiments, $R^{20}$ and $R^{25}$ are F and $R^{22}$ and $R^{23}$ are H. In some embodiments, $R^{20}$ and $R^{25}$ are H and $R^{22}$ and $R^{23}$ are F.

In some embodiments, $R^1$ is chosen according to any embodiment of any compound herein. In other words, any $R^1$ that is suitable for a compound of Formula 1 is also suitable for a compound of Formula 2.

In one aspect, the invention provides a compound having the structure:

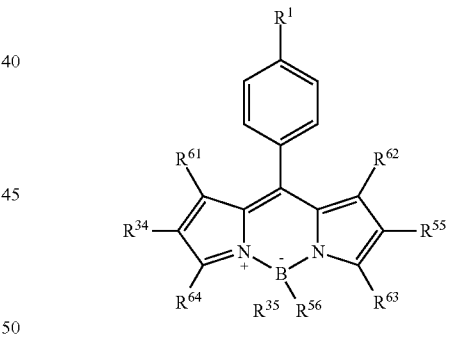

Formula 3 wherein $R^{34}$ is selected from H, substituted or unsubstituted alkyl, substituted or unsubstituted heteroalkyl, $-CN$, halogen and

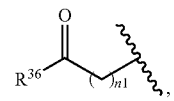

wherein $R^{36}$ is selected from H, substituted or unsubstituted alkyl, substituted or unsubstituted heteroalkyl, $-OR^{46}$, and $-N(R^{47})R^{48}$, wherein $R^{46}$, $R^{47}$ and $R^{48}$ are independently selected from H, substituted or unsubstituted alkyl, and substituted or unsubstituted heteroalkyl; and n1 is an integer selected from 1, 2, 3, 4, 5, 6, 7, 8, 9, 10, 11, and 12. $R^{55}$ is selected from H, substituted or unsubstituted alkyl substituted or unsubstituted heteroalkyl, —CN, halogen and

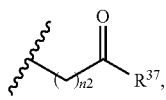

wherein $R^{37}$ is selected from H, substituted or unsubstituted alkyl, substituted or unsubstituted heteroalkyl, —$OR^{52}$, and —$N(R^{53})R^{54}$, wherein $R^{52}$, $R^{53}$ and $R^{54}$ are independently selected from H, substituted or unsubstituted alkyl, and substituted or unsubstituted heteroalkyl; and n2 is an integer selected from 1, 2, 3, 4, 5, 6, 7, 8, 9, 10, 11, and 12. $R^{35}$ is selected from halogen, substituted or unsubstituted alkyl, and substituted or unsubstituted heteroalkyl. $R^{56}$ is selected from halogen, substituted or unsubstituted alkyl, and substituted or unsubstituted heteroalkyl. $R^{61}$, $R^{62}$, $R^{63}$ and $R^{64}$ are independently selected from H, substituted or unsubstituted alkyl, substituted or unsubstituted alkenyl, substituted or unsubstituted aryl, and halogen. $R^{63}$ and $R^{55}$ are optionally joined to form, along with the atoms to which they are attached, a ring selected from substituted or unsubstituted cycloalkyl, substituted or unsubstituted heterocycloalkyl, substituted or unsubstituted aryl, and substituted or unsubstituted heteroaryl. $R^{64}$ and $R^{34}$ are optionally joined to form, along with the atoms to which they are attached, a ring selected from substituted or unsubstituted cycloalkyl, substituted or unsubstituted heterocycloalkyl, substituted or unsubstituted aryl, and substituted or unsubstituted heteroaryl. $R^1$ is as defined herein.

In some embodiments, $R^{34}$ is H. In some embodiments, $R^{34}$ is unsubstituted alkyl. In some embodiments, $R^{34}$ is $C_1$, $C_2$, $C_3$, $C_4$, $C_5$ or $C_6$ alkyl. In some embodiments, $R^{34}$ is ethyl. In some embodiments, $R^{34}$ is substituted alkyl. In some embodiments, $R^{34}$ is substituted $C_1$, $C_2$, $C_3$, $C_4$, $C_5$, $C_6$, $C_7$, $C_8$, $C_9$, $C_{10}$, $C_{11}$, or $C_{12}$ alkyl. In some embodiments, $R^{34}$ is substituted or unsubstituted heteroalkyl. In some embodiments, $R^{34}$ is substituted or unsubstituted alkoxy. In some embodiments, $R^{34}$ is —CN. In some embodiments, $R^{34}$ is selected from F, Cl, Br, and I.

In some embodiments, $R^{34}$ is

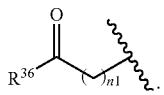

$R^{36}$ is selected from H, substituted or unsubstituted alkyl, substituted or unsubstituted heteroalkyl, —$OR^{46}$, and —$N(R^{47})^{R48}$, wherein $R^{46}$, $R^{47}$ and $R^{48}$ are independently selected from H, substituted or unsubstituted alkyl, and substituted or unsubstituted heteroalkyl. n1 is an integer selected from 1, 2, 3, 4, 5, 6, 7, 8, 9, 10, 11, and 12.

In some embodiments, $R^{36}$ is H. In some embodiments, $R^{36}$ is substituted or unsubstituted alkyl. In some embodiments, $R^{36}$ is substituted or unsubstituted heteroalkyl. In some embodiments, $R^{36}$ is substituted or unsubstituted poly (ethylene glycol). In some embodiments, $R^{36}$ is —OH. In some embodiments, $R^{36}$ is —$OR^{46}$ wherein $R^{46}$ is substituted or unsubstituted alkyl. In some embodiments, $R^{36}$ is —$N(R^{47})R^{48}$ wherein $R^{47}$ and $R^{48}$ are H. In some embodiments, $R^{36}$ is —$N(R^{47})R^{48}$ wherein $R^{47}$ is H; and $R^{48}$ is substituted or unsubstituted alkyl. In some embodiments, $R^{36}$ is —$N(R^{47})R^{48}$ wherein $R^{47}$ is H; and $R^{48}$ is substituted or unsubstituted heteroalkyl. In some embodiments, $R^{36}$ is —$N(R^{47})R^{48}$ wherein $R^{47}$ and $R^{48}$ are independently selected from substituted or unsubstituted alkyl, and substituted or unsubstituted heteroalkyl.

In some embodiments, $R^{55}$ is H. In some embodiments, $R^{55}$ is unsubstituted alkyl. In some embodiments, $R^{55}$ is $C_1$, $C_2$, $C_3$, $C_4$, $C_5$ or $C_6$ alkyl. In some embodiments, $R^{55}$ is ethyl. In some embodiments, $R^{55}$ is substituted alkyl. In some embodiments, $R^{55}$ is substituted $C_1$, $C_2$, $C_3$, $C_4$, $C_5$, $C_6$, $C_7$, $C_8$, $C_9$, $C_{10}$, $C_{11}$, or $C_{12}$ alkyl. In some embodiments, $R^{55}$ is substituted or unsubstituted heteroalkyl. In some embodiments, $R^{55}$ is substituted or unsubstituted alkoxy. In some embodiments, $R^{55}$ is —CN. In some embodiments, $R^{55}$ is selected from F, Cl, Br, and I.

In some embodiments, $R^{55}$ is

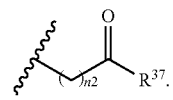

$R^{37}$ is selected from H, substituted or unsubstituted alkyl, substituted or unsubstituted heteroalkyl, —$OR^{52}$, and —$N(R^{53})R^{54}$, wherein $R^{52}$, $R^{53}$ and $R^{54}$ are independently selected from H, substituted or unsubstituted alkyl, and substituted or unsubstituted heteroalkyl. n2 is an integer selected from 1, 2, 3, 4, 5, 6, 7, 8, 9, 10, 11, and 12.

In some embodiments, $R^{37}$ is H. In some embodiments, $R^{37}$ is substituted or unsubstituted alkyl. In some embodiments, $R^{37}$ is substituted or unsubstituted heteroalkyl. In some embodiments, $R^{37}$ is substituted or unsubstituted poly (ethylene glycol). In some embodiments, $R^{37}$ is —OH. In some embodiments, $R^{37}$ is —$OR^{52}$ wherein $R^{52}$ is substituted or unsubstituted alkyl. In some embodiments, $R^{37}$ is —$N(R^{53})R^{54}$ wherein $R^{53}$ and $R^{54}$ are H. In some embodiments, $R^{37}$ is —$N(R^{53})R^{54}$ wherein $R^{53}$ is H; and $R^{54}$ is substituted or unsubstituted alkyl. In some embodiments, $R^{37}$ is —$N(R^{53})R^{54}$ wherein $R^{53}$ is H; and $R^{54}$ is substituted or unsubstituted arylalkyl. In some embodiments, $R^{37}$ is —$N(R^{53})R^{54}$ wherein $R^{53}$ is H; and $R^{54}$ is substituted or unsubstituted heteroalkyl. In some embodiments, $R^{37}$ is —$N(R^{53})R^{54}$ wherein $R^{53}$ and $R^{54}$ are independently selected from substituted or unsubstituted alkyl, and substituted or unsubstituted heteroalkyl. In some embodiments, $R^{37}$ is —$N(R^{53})R^{54}$ wherein $R^{53}$ is selected from substituted or unsubstituted alkyl, and substituted or unsubstituted heteroalkyl; and $R^{54}$ is substituted or unsubstituted arylalkyl. In some embodiments, $R^{37}$ is —$N(R^{53})R^{54}$ wherein $R^{53}$ is substituted alkyl; and $R^{54}$ is selected from H, substituted or unsubstituted alkyl, and substituted or unsubstituted heteroalkyl. In some embodiments, $R^{37}$ is —$N(R^{53})R^{54}$ wherein $R^{53}$ is substituted $C_1$, $C_2$, $C_3$, $C_4$, $C_5$, or $C_6$ alkyl; and $R^{54}$ is selected from H, substituted or unsubstituted alkyl, and substituted or unsubstituted heteroalkyl. In some embodiments, $R^{37}$ is —$N(R^{53})R^{54}$ wherein $R^{53}$ is —$CH_2COOH$; and $R^{54}$ is selected from H, substituted or unsubstituted alkyl, and substituted or unsubstituted heteroalkyl. In some embodiments, $R^{37}$ is —$N(R^{53})R^{54}$ wherein $R^{53}$ is —$CH_2COOH$ and $R^{54}$ is substituted or unsubstituted alkyl. In some embodiments, $R^{37}$ is —$N(R^{53})R^{54}$ wherein $R^{53}$ is —$CH_2COOH$ and $R^{54}$ is substituted or unsubstituted heteroalkyl.

In some embodiments, $R^{37}$ is
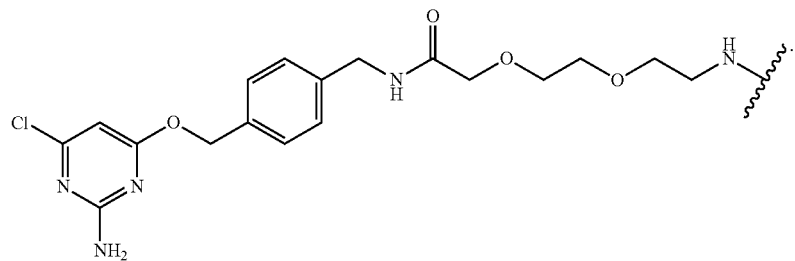 [SMILES: *NCCOCCOCC(=O)NCc1ccc(COc2cc(Cl)nc(N)n2)cc1]
In some embodiments, $R^{37}$ is
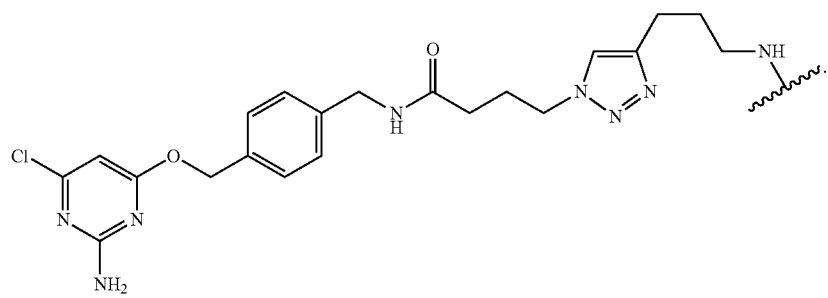 [SMILES: *NCCCc1cn(CCCC(=O)NCc2ccc(COc3cc(Cl)nc(N)n3)cc2)nn1]
In some embodiments, $R^{37}$ is
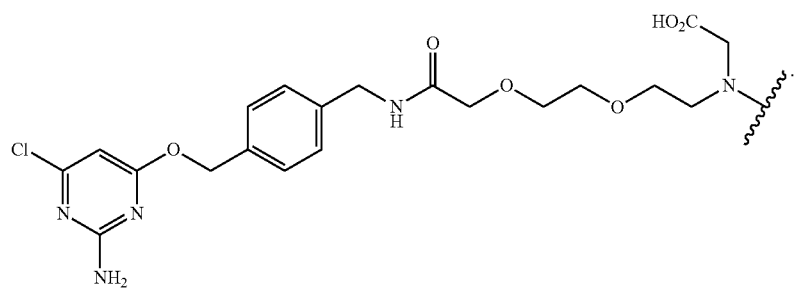 [SMILES: *N(CCOCCOCC(=O)NCc1ccc(COc2cc(Cl)nc(N)n2)cc1)CC(=O)O]
In some embodiments, $R^{37}$ is
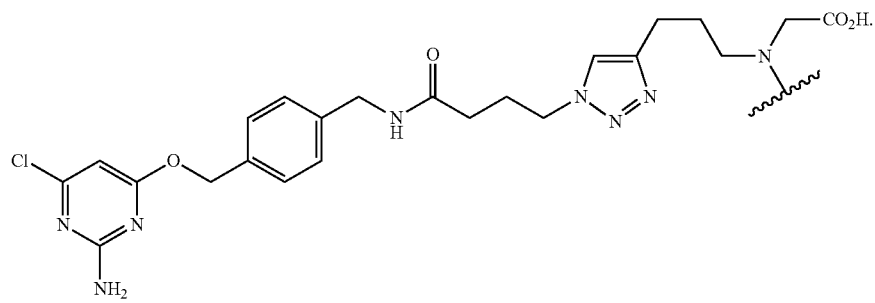 [SMILES: *N(CCCc1cn(CCCC(=O)NCc2ccc(COc3cc(Cl)nc(N)n3)cc2)nn1)CC(=O)O]

In some embodiments, $R^{35}$ is selected from F, Cl, Br, and I. In some embodiments, $R^{35}$ is F. In some embodiments, $R^{35}$ is unsubstituted heteroalkyl. In some embodiments, $R^{35}$ is $C_1$, $C_2$, $C_3$, $C_4$, $C_5$ or $C_6$ alkoxy. In some embodiments, $R^{35}$ is methoxy.

In some embodiments, $R^{56}$ is selected from F, Cl, Br, and I. In some embodiments, $R^{56}$ is F. In some embodiments, $R^{56}$ is unsubstituted heteroalkyl. In some embodiments, $R^{56}$ is $C_1$, $C_2$, $C_3$, $C_4$, $C_5$ or $C_6$ alkoxy. In some embodiments, $R^{56}$ is methoxy.

In some embodiments, $R^{61}$, $R^{62}$, $R^{63}$ and $R^{64}$ are unsubstituted alkyl. In some embodiments, $R^{61}$, $R^{62}$, $R^{63}$ and $R^{64}$ are independently selected from $C_1$, $C_2$, $C_3$, $C_4$, $C_5$ and $C_6$ alkyl. In some embodiments, $R^{61}$, $R^{62}$, $R^{63}$ and $R^{64}$ are methyl. In some embodiments, $R^{61}$, $R^{62}$, $R^{63}$ and $R^{64}$ are independently selected from H, methyl, ethyl, F, Cl, Br, and I. In some embodiments, $R^{64}$ and $R^{62}$ are the same. In some embodiments, $R^{63}$ and $R^{64}$ are the same.

In an exemplary embodiment, the invention provides a compound having the structure:

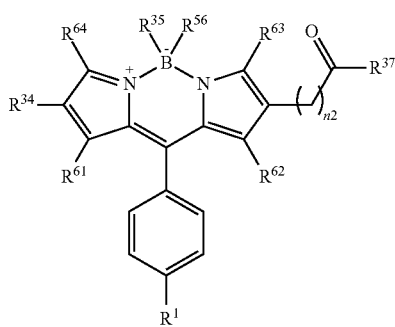

In some embodiments, $R^{55}$ is

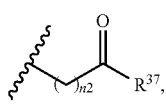

providing a compound having the structure:

Formula 3a

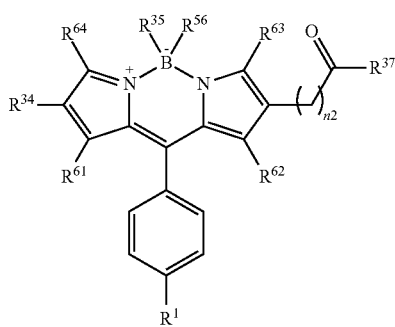

wherein $R^1$, $R^{34}$, $R^{35}$, $R^{37}$, $R^{56}$, $R^{61}$, $R^{62}$, $R^{63}$, $R^{64}$ and n2 are as defined herein.

In some embodiments, $R^{34}$ is

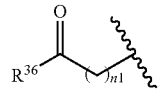

and $R^{55}$ is

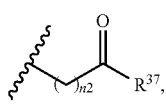

providing a compound having the structure:

Formula 3b

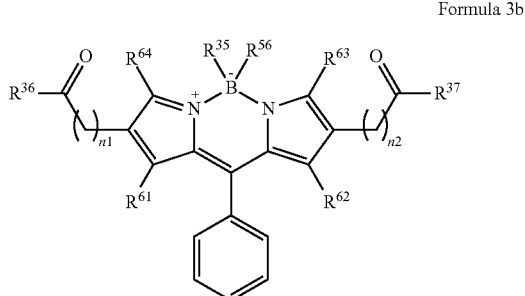

wherein $R^1$, $R^{35}$, $R^{36}$, $R^{37}$, $R^{56}$, $R^{61}$, $R^{62}$, $R^{63}$, $R^{64}$, n1 and n2 are as defined herein.

In some embodiments, the present invention provides a compound having a structure according to the formula:

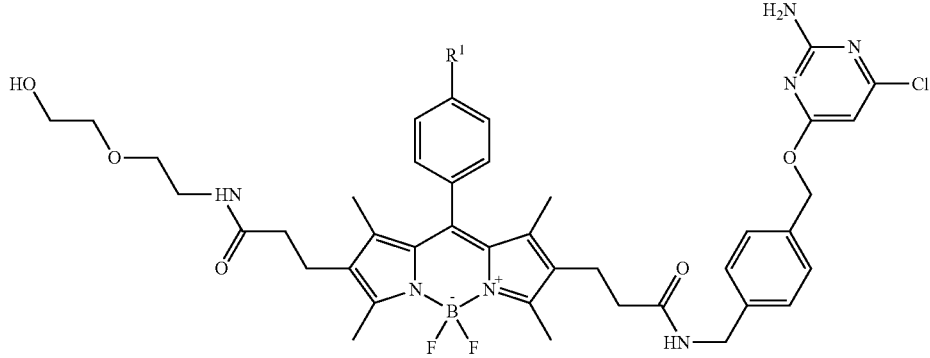

wherein R¹ is as defined herein.

In some embodiments, the present invention provides a compound having a structure according to the formula:

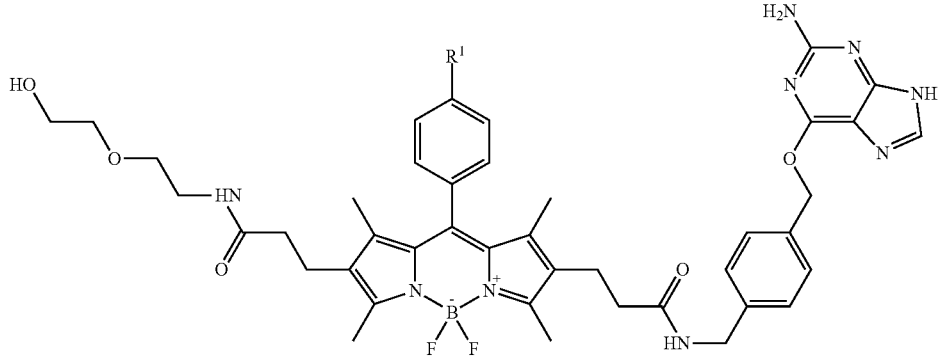

wherein R¹ is as defined herein.

In one aspect, the invention provides a compound having the structure:

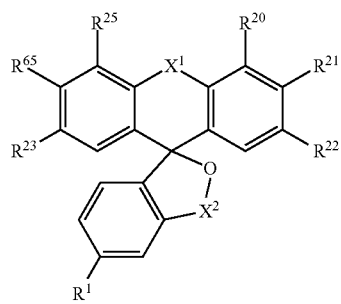

Formula 7 wherein $X^1$, $X^2$, $R^1$, $R^{20}$, $R^{21}$, $R^{22}$, $R^{23}$, $R^{25}$, and $R^{65}$ are as defined herein.

Reaction-Based Probes

Provided herein are compounds that are capable of forming a chelate with a metal ion and that can subsequently undergo a bond cleavage reaction. The bond cleavage alters the fluorescent properties of the compound, and thus provides a useful means for detecting the metal ion.

In one aspect, the invention provides a compound having the structure:

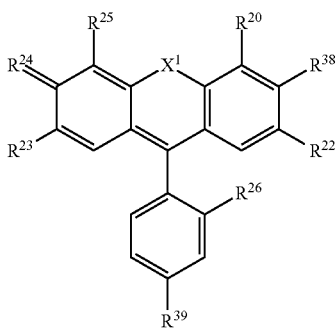

Formula 4 wherein $X^1$ is selected from O, $Si(R^{32})(R^{33})$, $C(R^{32})(R^{33})$, $Sn(R^{32})(R^{33})$, $B(R^{32})(R^{33})$, S, Se, and Te, wherein $R^{32}$ and $R^{33}$ are independently selected from H, substituted or unsubstituted alkyl, and substituted or unsubstituted heteroalkyl. $R^{20}$, $R^{22}$, $R^{23}$ and $R^{25}$ are independently selected from H, halogen, —SO₃H, substituted or unsubstituted alkyl and substituted or unsubstituted heteroalkyl. $R^{38}$ is selected from —OR⁴⁰, —NR⁴⁰R⁴¹, —OC(O)OR⁴⁰, —N(R⁶⁰)C(O)OR⁴⁰,

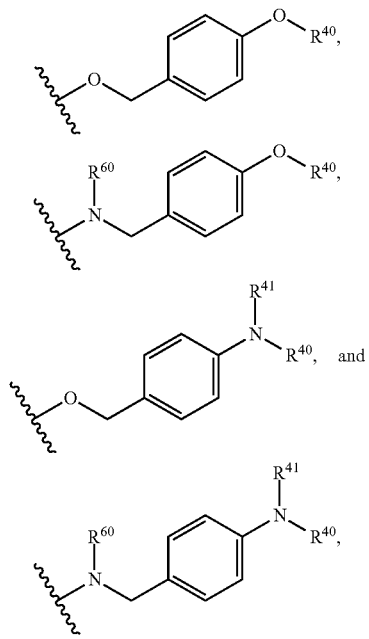

wherein $R^{40}$ and $R^{44}$ are independently selected from H, substituted or unsubstituted alkyl, substituted or unsubstituted heteroalkyl, substituted or unsubstituted arylalkyl, and substituted or unsubstituted heteroarylalkyl; and $R^{60}$ is selected from H, substituted or unsubstituted alkyl and substituted or unsubstituted heteroalkyl. $R^{24}$ is selected from O and $NR^{30}R^{31}$, wherein $R^{30}$ and $R^{31}$ are independently selected from H, substituted or unsubstituted alkyl, substituted or unsubstituted heteroalkyl, substituted or unsubstituted aryl and substituted or unsubstituted heteroaryl. $R^{30}$ and $R^{31}$ are optionally joined to form, along with the atoms to which they are attached, a substituted or unsubstituted heterocycloalkyl. $R^{31}$ is optionally present. $R^{30}$ and $R^{25}$ or $R^{30}$ and $R^{23}$ are optionally joined to form, along with the atoms to which they are attached, a substituted or unsubstituted heterocycloalkyl. $R^{31}$ and $R^{23}$ are optionally joined to form, along with the atoms to which they are attached, a substituted or unsubstituted heterocycloalkyl. $R^{26}$ is selected from H, —COOH, substituted or unsubstituted alkyl and substituted or unsubstituted heteroalkyl. $R^{39}$ is selected from H, substituted or unsubstituted alkyl, substituted or unsubstituted heteroalkyl, —$OR^{42}$, —$C(O)OR^{42}$, —$OC(O)OR^{42}$, —$C(O)N(R^{43})R^{44}$, —$OC(O)N(R^{43})R^{44}$, —$N(R^{43})C(O)R^{45}$ and —$SO_3H$, wherein $R^{42}$, $R^{43}$, $R^{44}$ and $R^{45}$ are independently selected from H, substituted or unsubstituted alkyl, substituted or unsubstituted heteroalkyl, substituted or unsubstituted aryl and substituted or unsubstituted heteroaryl.

In some embodiments, $X^1$ is O. In some embodiments, $X^1$ is $Si(R^{32})(R^{33})$. In some embodiments, $X^1$ is $C(R^{32})(R^{33})$. In some embodiments, $X^1$ is $Sn(R^{32})(R^{33})$. In some embodiments, $X^1$ is $B(R^{32})(R^{33})$. In some embodiments, $X^1$ is S. In some embodiments, $X^1$ is Se. In some embodiments, $X^1$ is Te. In some embodiments, $R^{32}$, $R^{33}$ or both are unsubstituted alkyl. In some embodiments, $R^{32}$, $R^{33}$ or both are independently selected from $C_1$, $C_2$, $C_3$, $C_4$, $C_5$ and $C_6$ alkyl. In some embodiments, $R^{32}$, $R^{33}$ or both are methyl. In some embodiments, $R^{32}$ and $R^{33}$ are methyl.

In some embodiments, $R^{38}$ is —$OR^{40}$ wherein $R^{40}$ is substituted alkyl. In some embodiments, $R^{40}$ is substituted $C_1$, $C_2$, $C_3$, $C_4$, $C_5$, or $C_6$ alkyl. In some embodiments, $R^{40}$ is substituted methyl. In some embodiments, $R^{40}$ is substituted heteroarylalkyl. In some embodiments, $R^{40}$ is substituted heteroarylmethyl. In some embodiments, $R^{40}$ is substituted pyridinylmethyl.

In some embodiments, $R^{38}$ is $NR^{40}R^{41}$ wherein $R^{40}$ is as defined herein and $R^{41}$ is unsubstituted alkyl. In some embodiments, $R^{41}$ is $C_1$, $C_2$, $C_3$, $C_4$, $C_5$ or $C_6$ alkyl. In some embodiments, $R^{41}$ is methyl. In some embodiments, $R^{38}$ is $NR^{40}R^{41}$ wherein $R^{40}$ is as defined herein and $R^{41}$ is H.

In some embodiments, $R^{38}$ is selected from —$N(R^{60})C(O)OR^{40}$,

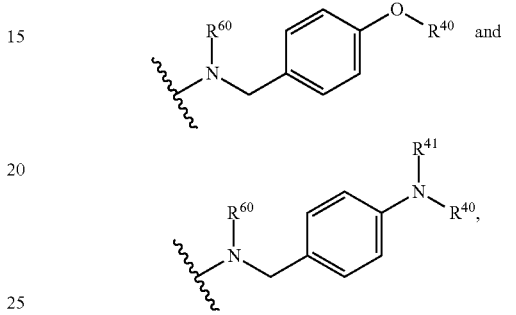

wherein $R^{40}$ and $R^{41}$ are as defined herein; and $R^{60}$ is H. In some embodiments, $R^{38}$ is selected from —$N(R^{60})C(O)OR^{40}$,

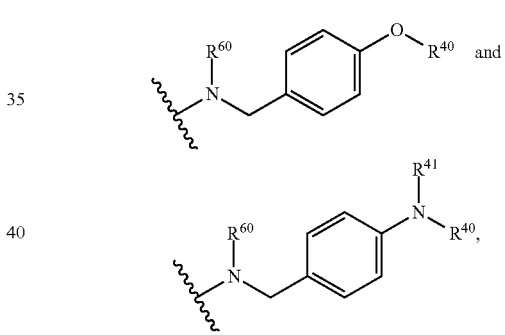

wherein $R^{40}$ and $R^{41}$ are as defined herein; and $R^{60}$ is unsubstituted alkyl. In some embodiments, $R^{60}$ is $C_1$, $C_2$, $C_3$, $C_4$, $C_5$ or $C_6$ alkyl. In some embodiments, $R^{60}$ is methyl.

In some embodiments, $R^{40}$ is —$CH_2$—$R^{57}$—$(CH_2)_{n3}$—$N(R^{58})R^{59}$, wherein $R^{57}$ is selected from substituted or unsubstituted aryl and substituted or unsubstituted heteroaryl; $R^{58}$ and $R^{59}$ are independently selected from substituted or unsubstituted alkyl, substituted or unsubstituted heteroalkyl, substituted or unsubstituted arylalkyl, substituted or unsubstituted heteroarylalkyl; and n3 is an integer selected from 0, 1, 2, 3, 4, 5, and 6.

In some embodiments, $R^{57}$ is unsubstituted heteroaryl. In some embodiments, $R^{57}$ is pyridinyl. In some embodiments, $R^{57}$ is pyridin-2,6-diyl. In some embodiments, $R^{57}$ is unsubstituted aryl.

In some embodiments, $R^{58}$ and $R^{59}$ are independently selected from
pyridin-2-ylmethyl,
2-(dimethylamino)ethyl,
di(pyridin-2-yl)methyl,
(4-methoxy-3,5-dimethylpyridin-2-yl)methyl,
(6-(hydroxymethyl)pyridin-2-yl)methyl, (6-(methoxymethyl)pyridin-2-yl)methyl,
(6-(ethoxymethyl)pyridin-2-yl)methyl,
benzyl,
2-hydroxyethyl,
hydroxymethyl,
methoxymethyl,
ethoxymethyl,
2-hydroxybenzyl,
2-methoxybenzyl,
2-ethoxybenzyl,
2-methoxy-2-oxoethyl,
carboxymethyl,
2-ethoxy-2-oxoethyl,
2-(ethylthio)ethyl,
2-(methylthio)ethyl,
2-mercaptoethyl,
thiazol-2-ylmethyl,
2-ethoxyethyl,
[2,2'-bipyridin]-6-ylmethyl,
2-(pyridin-2-yl)ethyl,
(1H-imidazol-2-yl)methyl, and
(1H-pyrazol-3-yl)methyl.

In some embodiments, n3 is an integer selected from 0, 1, 2, and 3. In some embodiments, n3 is 1. In some embodiments n3 is 2.

In some embodiments, $R^{40}$ is

In some embodiments, $R^{40}$ is

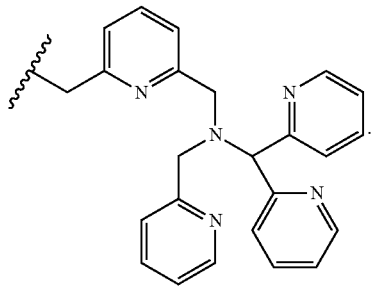 [SMILES: *Cc1cccc(CN(Cc2ccccn2)C(c2ccccn2)c2ccccn2)n1]

In some embodiments, $R^{40}$ is

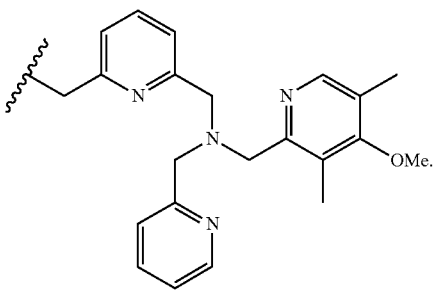 [SMILES: *Cc1cccc(CN(Cc2ccccn2)Cc2ncc(C)c(OC)c2C)n1]

In some embodiments, $R^{40}$ is

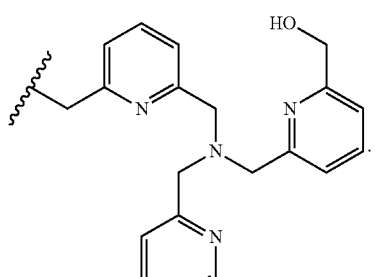

In some embodiments, $R^{40}$ is

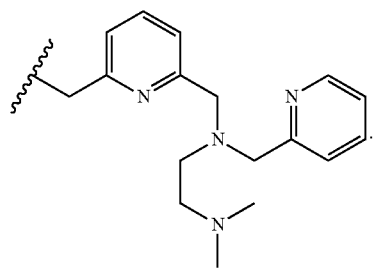

In some embodiments, $R^{40}$ is

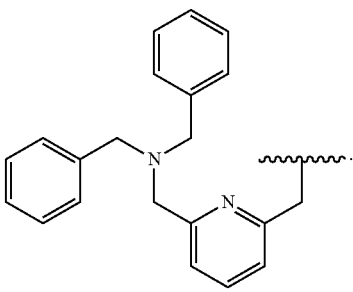 [SMILES: *Cc1cccc(CN(Cc2ccccc2)Cc2ccccc2)n1]

In some embodiments, $R^{40}$ is
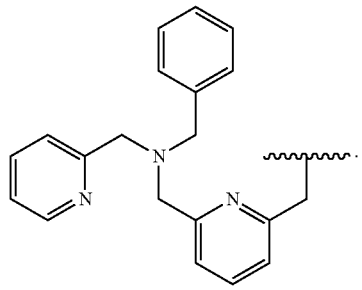 [SMILES: *Cc1cccc(CN(Cc2ccccc2)Cc2ccccn2)n1]
In some embodiments, $R^{40}$ is
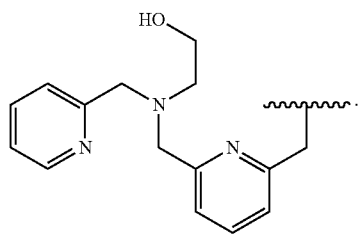 [SMILES: *Cc1cccc(CN(CCO)Cc2ccccn2)n1]
In some embodiments, $R^{40}$ is
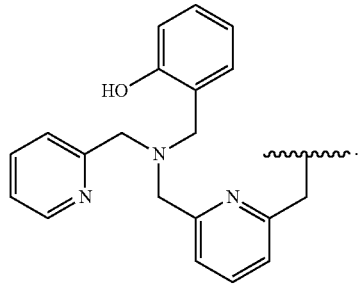 [SMILES: *Cc1cccc(CN(Cc2ccccn2)Cc2ccccc2O)n1]
In some embodiments, $R^{40}$ is
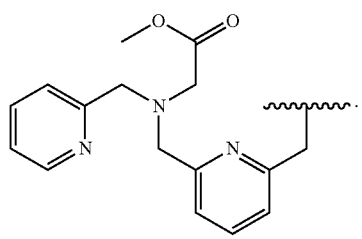 [SMILES: *Cc1cccc(CN(CC(=O)OC)Cc2ccccn2)n1]
In some embodiments, $R^{40}$ is
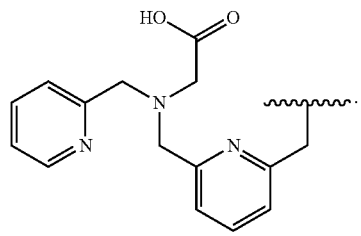 [SMILES: *Cc1cccc(CN(CC(=O)O)Cc2ccccn2)n1]
In some embodiments, $R^{40}$ is
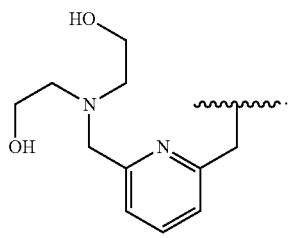 [SMILES: *Cc1cccc(CN(CCO)CCO)n1]
In some embodiments, $R^{40}$ is
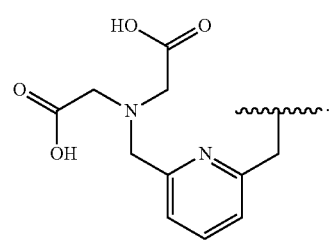 [SMILES: *Cc1cccc(CN(CC(=O)O)CC(=O)O)n1]
In some embodiments, $R^{40}$ is
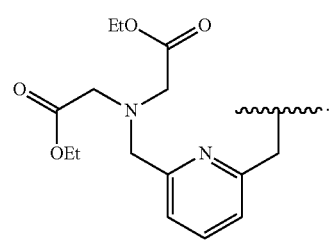 [SMILES: *Cc1cccc(CN(CC(=O)OCC)CC(=O)OCC)n1]
In some embodiments, $R^{40}$ is
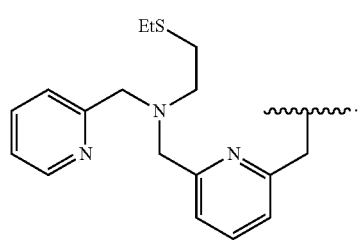

In some embodiments, $R^{40}$ is
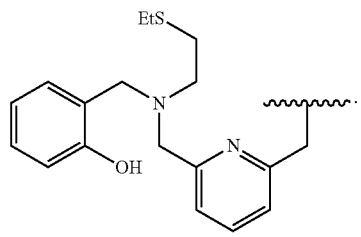
In some embodiments, $R^{40}$ is
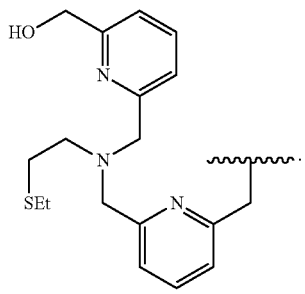
In some embodiments, $R^{40}$ is
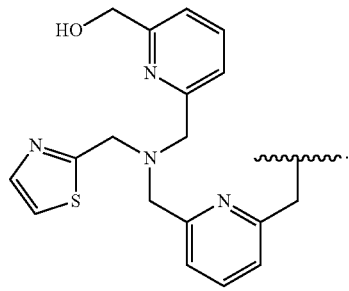 [SMILES: *Cc1cccc(CN(Cc2cccc(CO)n2)Cc2nccs2)n1]
In some embodiments, $R^{40}$ is
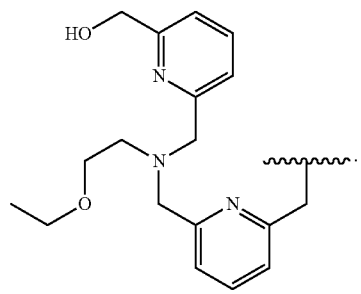 [SMILES: *Cc1cccc(CN(CCOCC)Cc2cccc(CO)n2)n1]
In some embodiments, $R^{40}$ is
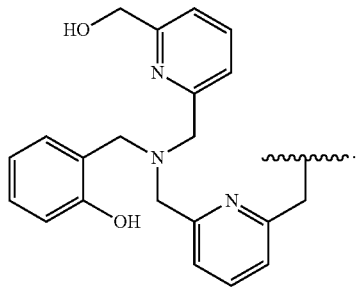 [SMILES: *Cc1cccc(CN(Cc2cccc(CO)n2)Cc2ccccc2O)n1]
In some embodiments, $R^{40}$ is
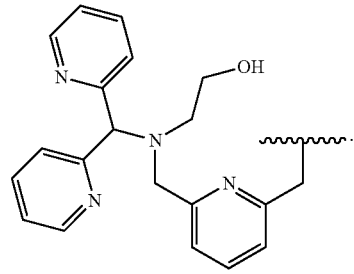 [SMILES: *Cc1cccc(CN(CCO)C(c2ccccn2)c2ccccn2)n1]
In some embodiments, $R^{40}$ is
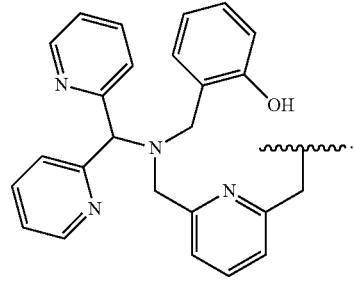 [SMILES: *Cc1cccc(CN(Cc2ccccc2O)C(c2ccccn2)c2ccccn2)n1]
In some embodiments, $R^{40}$ is
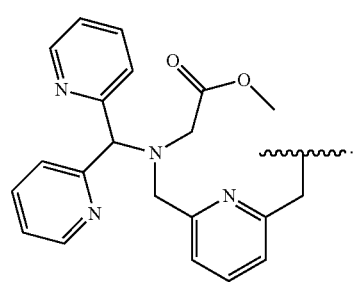 [SMILES: *Cc1cccc(CN(CC(=O)OC)C(c2ccccn2)c2ccccn2)n1]

In some embodiments, $R^{40}$ is

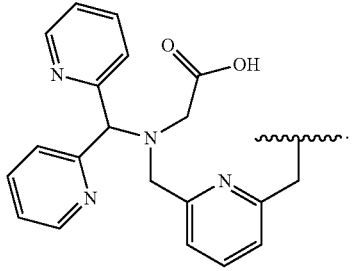 [SMILES: *Cc1cccc(CN(CC(=O)O)C(c2ccccn2)c2ccccn2)n1]

In some embodiments, $R^{40}$ is

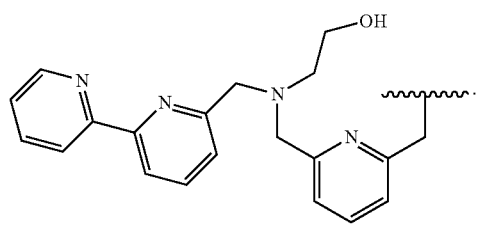 [SMILES: *Cc1cccc(CN(CCO)Cc2cccc(-c3ccccn3)n2)n1]

In some embodiments, $R^{40}$ is

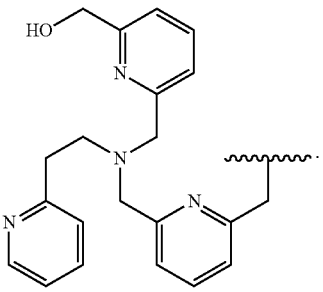

In some embodiments, $R^{40}$ is

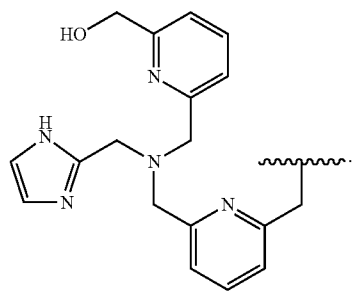 [SMILES: *Cc1cccc(CN(Cc2cccc(CO)n2)Cc2ncc[nH]2)n1]

In some embodiments, $R^{40}$ is

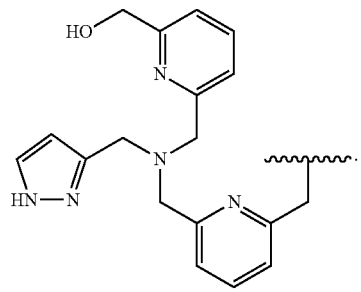 [SMILES: *Cc1cccc(CN(Cc2cc[nH]n2)Cc2cccc(CO)n2)n1]

In some embodiments, $R^{24}$ is O. In some embodiments, $R^{24}$ is $NR^{30}R^{31}$ wherein $R^{30}$, $R^{31}$ or both are unsubstituted alkyl. In some embodiments, $R^{30}$, $R^{31}$ or both are independently selected from $C_1$, $C_2$, $C_3$, $C_4$, $C_5$ and $C_6$ alkyl. In some embodiments, $R^{30}$, $R^{31}$ or both are methyl. In some embodiments, $R^{30}$ and $R^{31}$ are methyl. In some embodiments, $R^{30}$, $R^{31}$ or both are H. In some embodiments, $R^{30}$ is H and $R^{31}$ is not present. In some embodiments, $R^{30}$ is selected from substituted or unsubstituted alkyl and substituted or unsubstituted heteroalkyl; and $R^{31}$ is not present. In some embodiments, $R^{30}$ and $R^{25}$ are joined to form, along with the atoms to which they are attached, a substituted or unsubstituted heterocycloalkyl; and $R^{31}$ and $R^{23}$ are joined to form, along with the atoms to which they are attached, a substituted or unsubstituted heterocycloalkyl.

In some embodiments, $R^{26}$ is H. In some embodiments, $R^{26}$ is unsubstituted alkyl. In some embodiments, $R^{26}$ is selected from $C_1$, $C_2$, $C_3$, $C_4$, $C_5$ and $C_6$ alkyl. In some embodiments, $R^{26}$ is methyl. In some embodiments, $R^{26}$ is substituted alkyl. In some embodiments, $R^{26}$ is selected from substituted $C_1$, $C_2$, $C_3$, $C_4$, $C_5$ and $C_6$ alkyl. In some embodiments, $R^{26}$ is $-CH_2OH$. In some embodiments, $R^{26}$ is $-COOH$.

In some embodiments, $R^{20}$, $R^{22}$, $R^{23}$ and $R^{25}$ are independently selected from H and unsubstituted alkyl. In some embodiments, $R^{20}$, $R^{22}$, $R^{23}$ and $R^{25}$ are independently selected from H and $C_1$, $C_2$, $C_3$, $C_4$, $C_5$ and $C_6$ alkyl. In some embodiments, $R^{20}$, $R^{22}$, $R^{23}$ and $R^{25}$ are independently selected from H and methyl. In some embodiments, $R^{20}$, $R^{22}$, $R^{23}$ and $R^{25}$ are H. In some embodiments, $R^{20}$, $R^{22}$, $R^{23}$ and $R^{25}$ are methyl. In some embodiments, $R^{20}$ and $R^{25}$ are the same. In some embodiments, $R^{22}$ and $R^{23}$ are the same. In some embodiments, $R^{20}$ and $R^{25}$ are methyl and $R^{22}$ and $R^{23}$ are H. In some embodiments, $R^{20}$ and $R^{25}$ are H and $R^{22}$ and $R^{23}$ are methyl. In some embodiments, $R^{20}$ and $R^{25}$ are F and $R^{22}$ and $R^{23}$ are H. In some embodiments, $R^{20}$ and $R^{25}$ are H and $R^{22}$ and $R^{23}$ are F.

In some embodiments, $R^{39}$ is H. In some embodiments, $R^{39}$ is substituted or unsubstituted alkyl. In some embodiments, $R^{39}$ is unsubstituted alkyl. In some embodiments, $R^{39}$ is $C_1$, $C_2$, $C_3$, $C_4$, $C_5$ or $C_6$ alkyl. In some embodiments, $R^{39}$ is methyl. In some embodiments, $R^{39}$ is substituted alkyl. In some embodiments, $R^{39}$ is substituted $C_1$, $C_2$, $C_3$, $C_4$, $C_5$ or $C_6$ alkyl. In some embodiments, $R^{39}$ is $CH_2OH$. In some embodiments, $R^{39}$ is substituted or unsubstituted heteroalkyl. In some embodiments, $R^{39}$ is substituted or unsubstituted poly(ethylene glycol). In some embodiments, $R^{39}$ is $-OR^{42}$, wherein $R^{42}$ is H. In some embodiments, $R^{39}$ is $-OR^{42}$, wherein $R^{42}$ is unsubstituted alkyl. In some embodiments, $R^{39}$ is $-OR^{42}$, wherein $R^{42}$ is $C_1$, $C_2$, $C_3$, $C_4$, $C_5$ or $C_6$ alkyl. In some embodiments, $R^{39}$ is $-OR^{42}$, wherein $R^{42}$ is methyl.

In some embodiments, $R^{39}$ is —C(O)O$R^{42}$, wherein $R^{42}$ is H.
In some embodiments, $R^{39}$ is —SO$_3$H.
In some embodiments, $R^{39}$ is
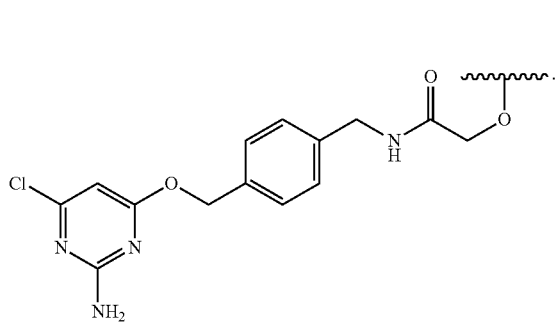 [SMILES: *OCC(=O)NCc1ccc(COc2cc(Cl)nc(N)n2)cc1]
In some embodiments, $R^{39}$ is
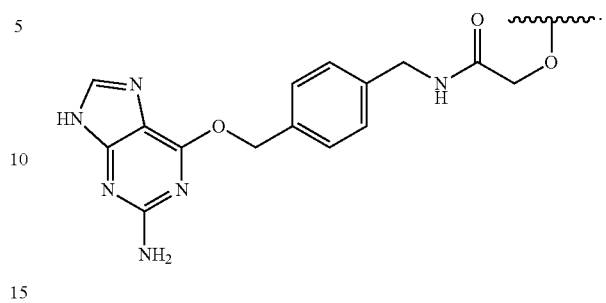
In some embodiments, $R^{39}$ is
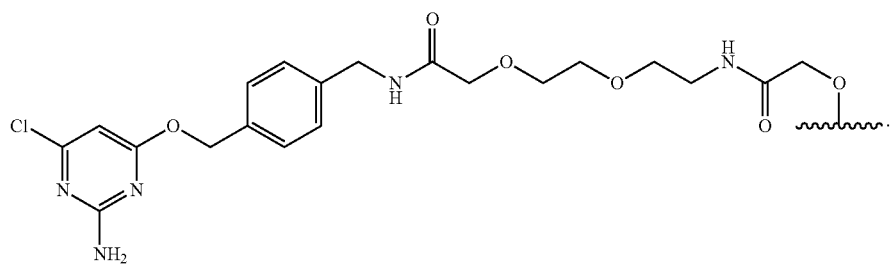 [SMILES: *OCC(=O)NCCOCCOCC(=O)NCc1ccc(COc2cc(Cl)nc(N)n2)cc1]
In some embodiments, $R^{39}$ is
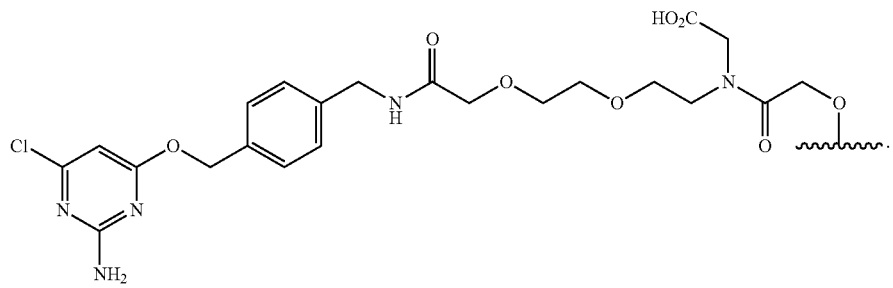 [SMILES: *OCC(=O)N(CCOCCOCC(=O)NCc1ccc(COc2cc(Cl)nc(N)n2)cc1)CC(=O)O]
In some embodiments, $R^{39}$ is
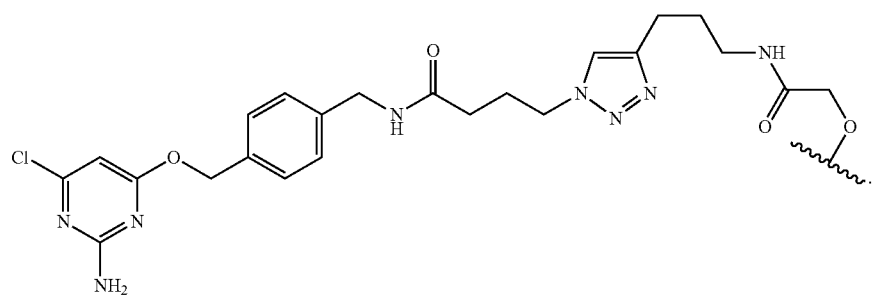 [SMILES: *OCC(=O)NCCCc1cn(CCCC(=O)NCc2ccc(COc3cc(Cl)nc(N)n3)cc2)nn1]

In some embodiments, $R^{39}$ is

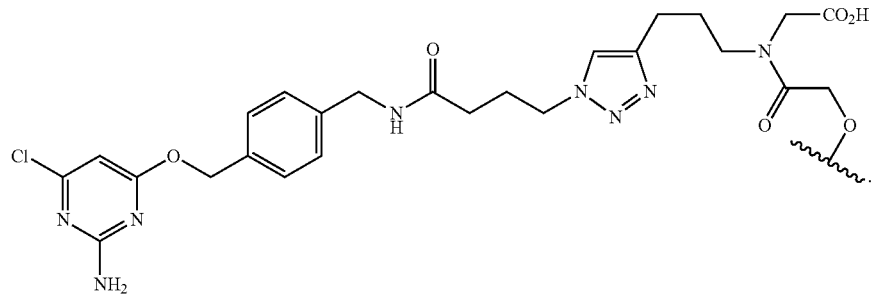 [SMILES: *OCC(=O)N(CCCc1cn(CCCC(=O)NCc2ccc(COc3cc(Cl)nc(N)n3)cc2)nn1)CC(=O)O]

In one aspect, the invention provides a compound having the structure:

Formula 5

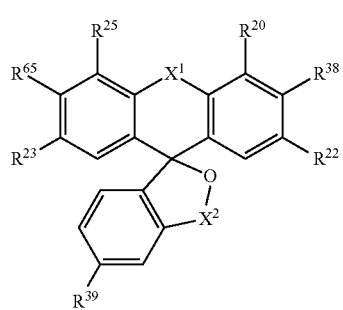

wherein $R^{65}$ is $OR^{68}$ or $NR^{66}R^{67}$, wherein $R^{66}$, $R^{67}$ and $R^{68}$ are independently selected from H, substituted or unsubstituted alkyl, substituted or unsubstituted heteroalkyl, substituted or unsubstituted aryl and substituted or unsubstituted heteroaryl. $R^{66}$ and $R^{67}$ are optionally joined to form, along with the atoms to which they are attached, a substituted or unsubstituted heterocycloalkyl. $X^2$ is —CH$_2$— or —C(O)—. $X^1$, $R^{20}$, $R^{22}$, $R^{23}$, $R^{25}$, $R^{38}$, and $R^{39}$ are as defined herein.

In some embodiments, $R^{65}$ is $OR^{68}$, wherein $R^{68}$ is H. In some embodiments, $R^{65}$ is $NR^{66}R^{67}$, wherein $R^{66}$, $R^{67}$ or both are unsubstituted alkyl. In some embodiments, $R^{66}$, $R^{67}$ or both are independently selected from $C_1$, $C_2$, $C_3$, $C_4$, $C_5$ and $C_6$ alkyl. In some embodiments, $R^{66}$, $R^{67}$ or both are methyl. In some embodiments, $R^{66}$ and $R^{67}$ are methyl. In some embodiments, $R^{66}$, $R^{67}$ or both are ethyl. In some embodiments, $R^{66}$ and $R^{67}$ are ethyl. In some embodiments, $R^{66}$, $R^{67}$ or both are H.

In some embodiments, the present invention provides a compound having a structure according to the formula:

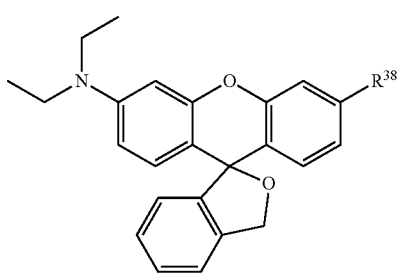

wherein $R^{38}$ is as defined herein.

In an exemplary embodiment, the invention provides a compound having the structure:

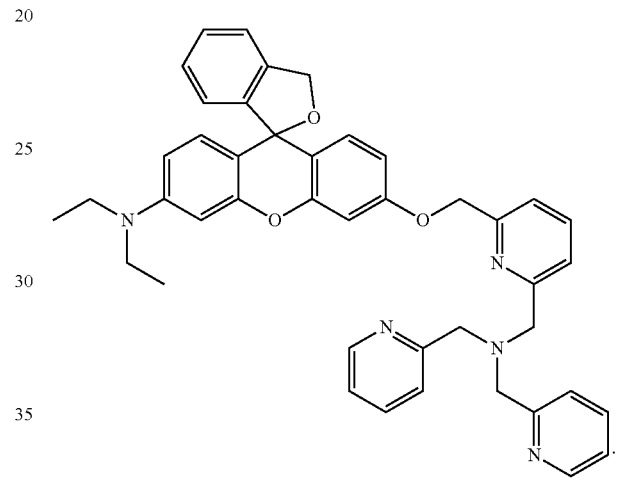

In one aspect, the invention provides a compound having the structure:

Formula 6

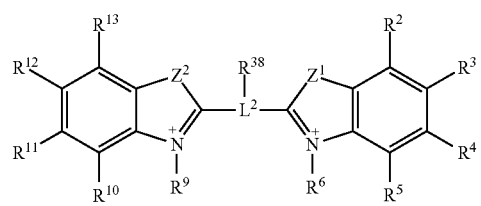

wherein $L^2$-$R^{38}$ has a structure selected from:

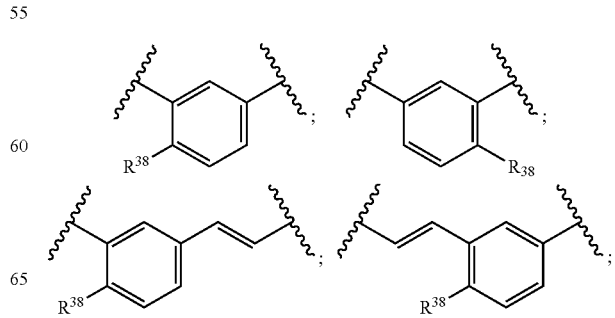

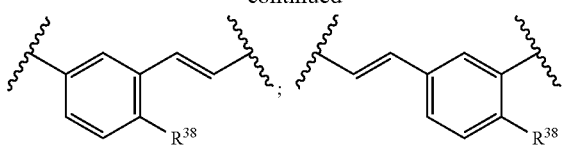

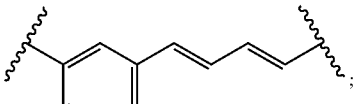

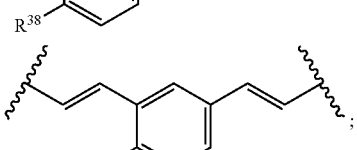

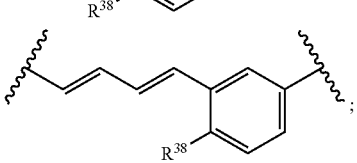

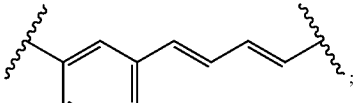

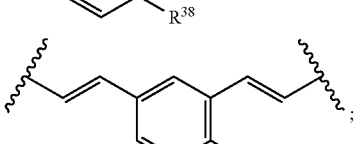

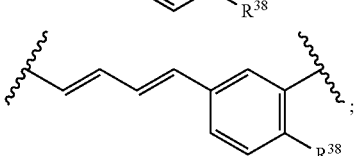

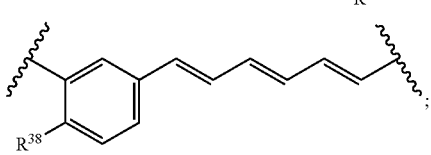

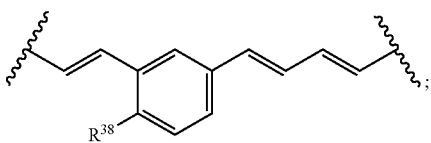

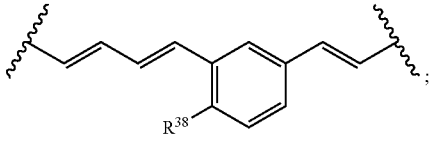

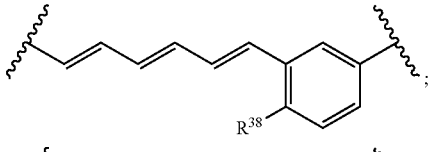

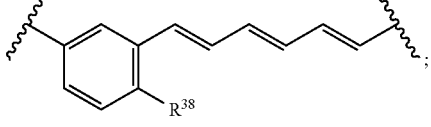

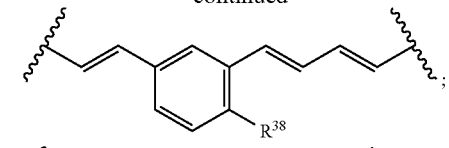

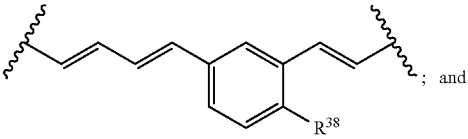

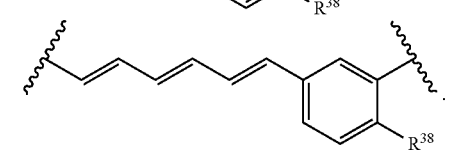

$Z^1$, $Z^2$, $R^2$, $R^3$, $R^4$, $R^5$, $R^6$, $R^9$, $R^{10}$, $R^{11}$, $R^{12}$, $R^{13}$ and $R^{38}$ are as defined herein.

In some embodiments, $L^2$-$R^{38}$ has the structure:

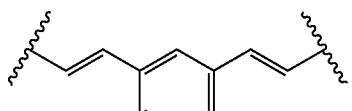

or

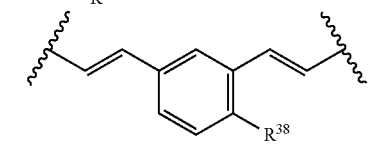

In some embodiments, the present invention provides a compound having a structure according to the formula:

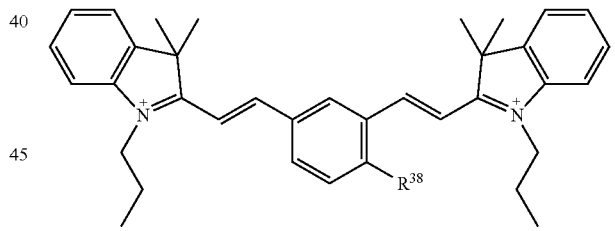

wherein $R^{38}$ is as defined herein.

In one aspect, the invention provides a complex between a metal ion and a compound disclosed herein. In some embodiments, the metal ion is a copper ion.

In one aspect, the invention provides a cleavage product formed through complexation of a reaction-based probe disclosed herein with a metal ion and subsequent (spontaneous) bond cleavage within the reaction-based probe.

In some embodiments, the bond cleavage occurs in the presence of oxygen.

In some embodiments with respect to reaction-based probes according to formulae 4-6, the $R^{40}$ moiety is cleaved off (for example, through cleavage of the bond between $R^{40}$ and the oxygen or nitrogen atom to which it is attached). In some embodiments, the linker moiety between $R^{40}$ and the oxygen or nitrogen atom that is directly attached to the core structure (i.e., the structure to which $R^{38}$ is attached) is cleaved (for example, through cleavage of the bond between the linker moiety and the oxygen or nitrogen atom that is directly attached to the core structure). In some embodiments, the $R^{40}$ moiety and any linker moiety between $R^{40}$ and the oxygen or nitrogen atom that is directly attached to the core structure (i.e., the structure to which $R^{38}$ is attached) is cleaved off. In some embodiments, the structure of the cleavage product thus formed is essentially equivalent to that of the original reaction-based probe with the exception that $R^{38}$ is —OH, —NHR$^{41}$ or —NHR$^{60}$, depending on the $R^{38}$ moiety of the original reaction-based probe.

Exemplary bond cleavage reactions of exemplary reaction-based probes according to formulae 5 and 6 are shown below.

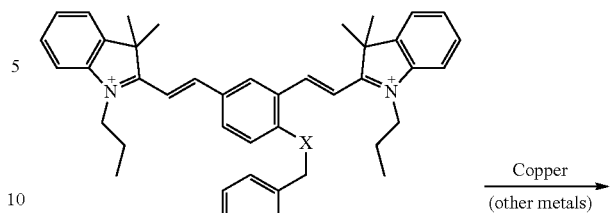

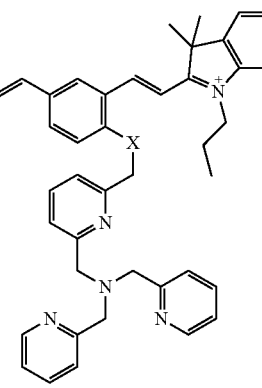

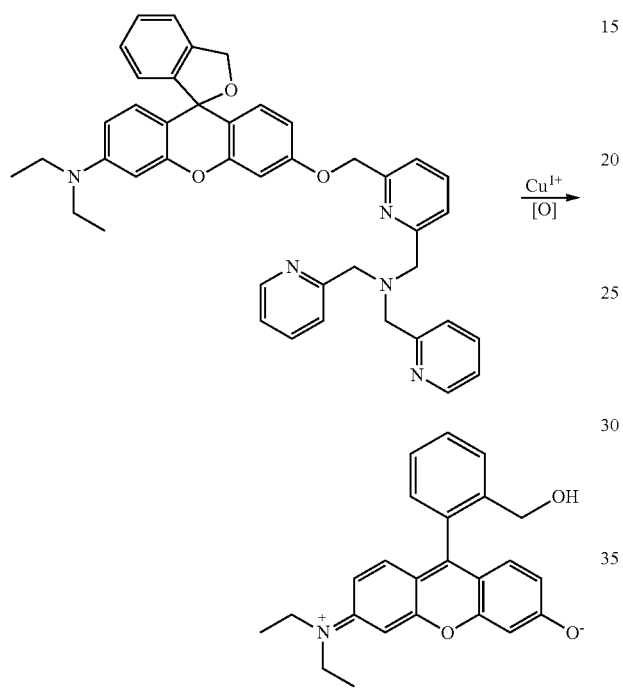

X: O, NR'R''

Additional embodiments of the compounds are shown below, wherein $R_1$ and $R_2$ refer to the various moieties that can be substituents of any of the cyanine and fluorescein cores. n in the figure is an integer selected from 1-6.

Receptors ($R_1$)

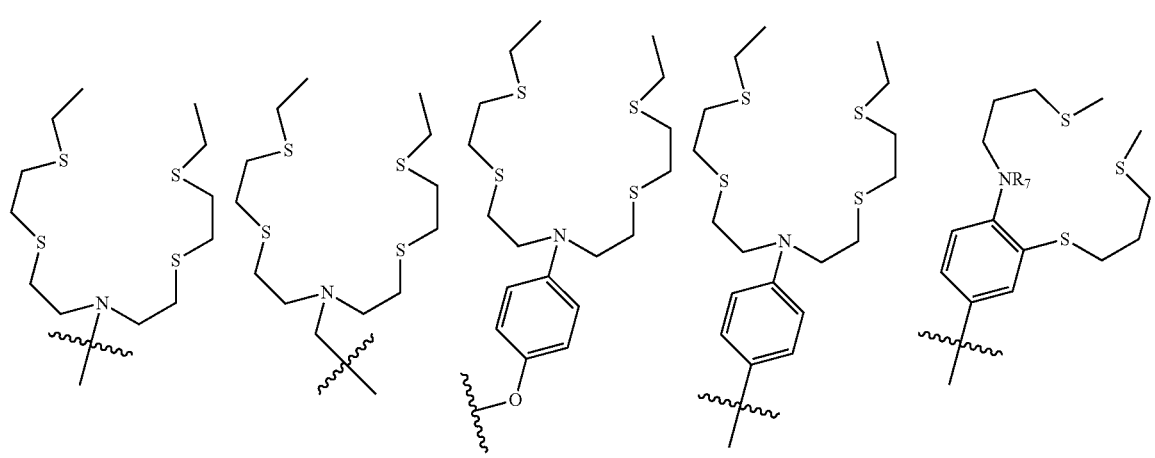

-continued
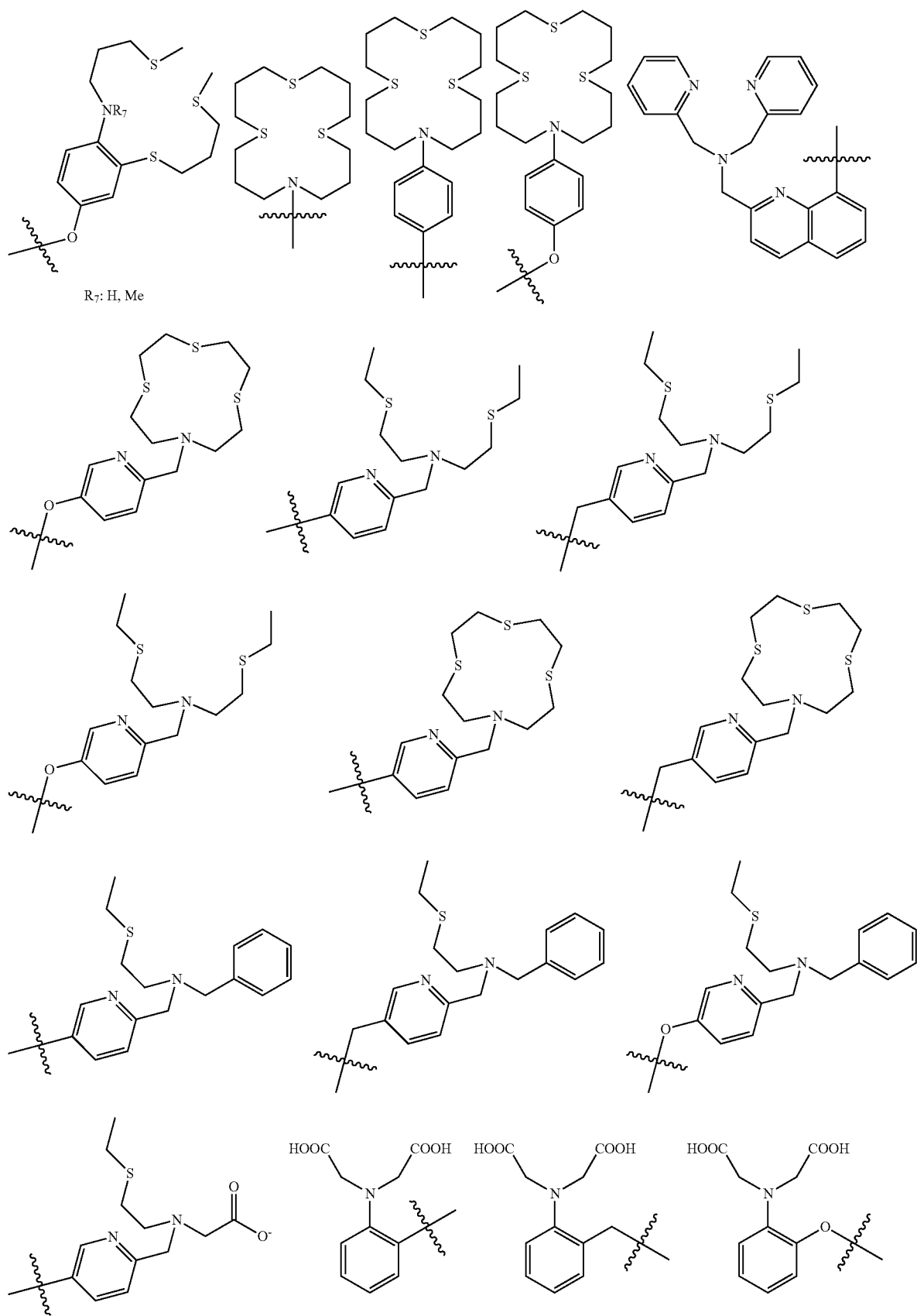

-continued
Tails ($R_2$)
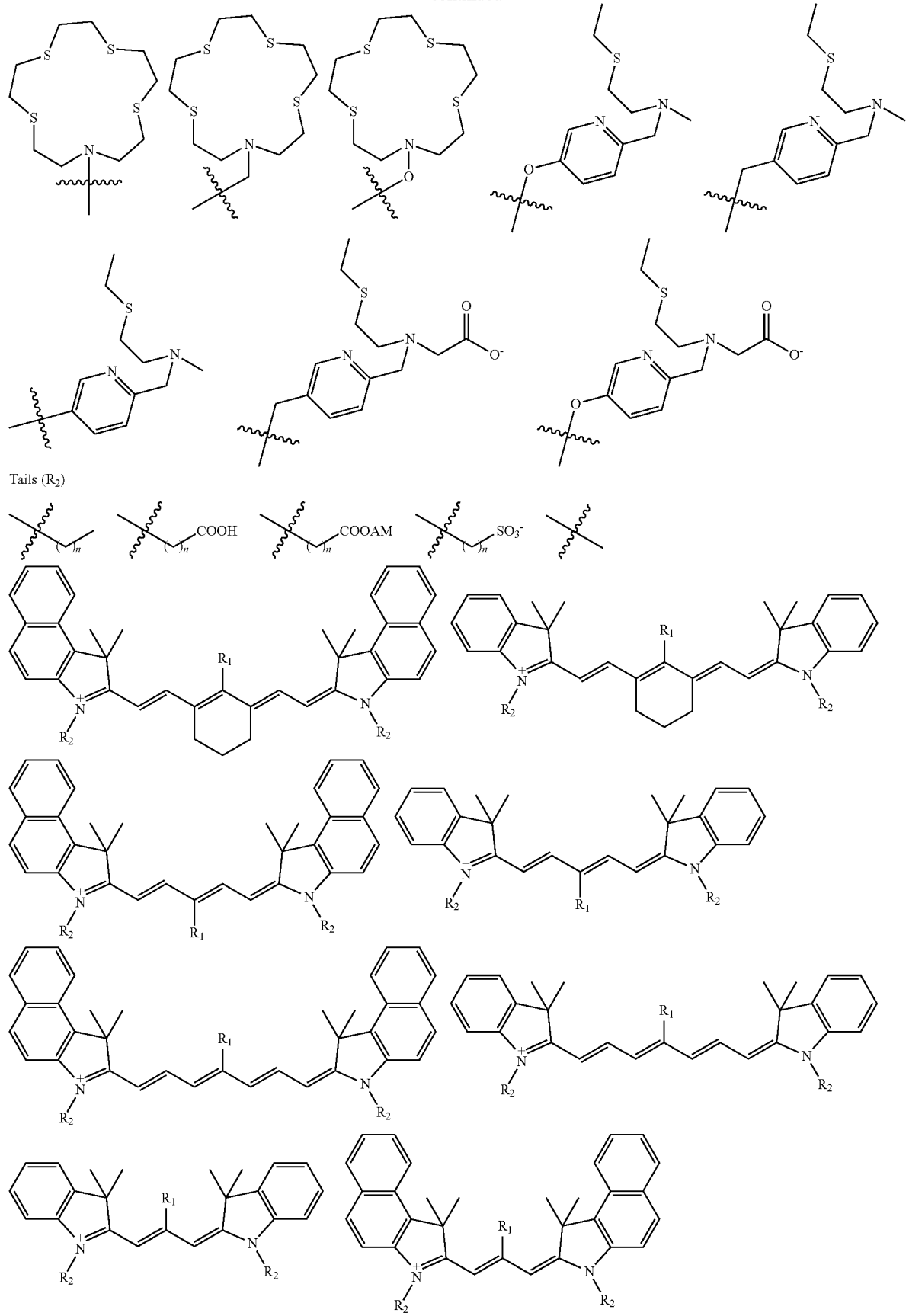

-continued
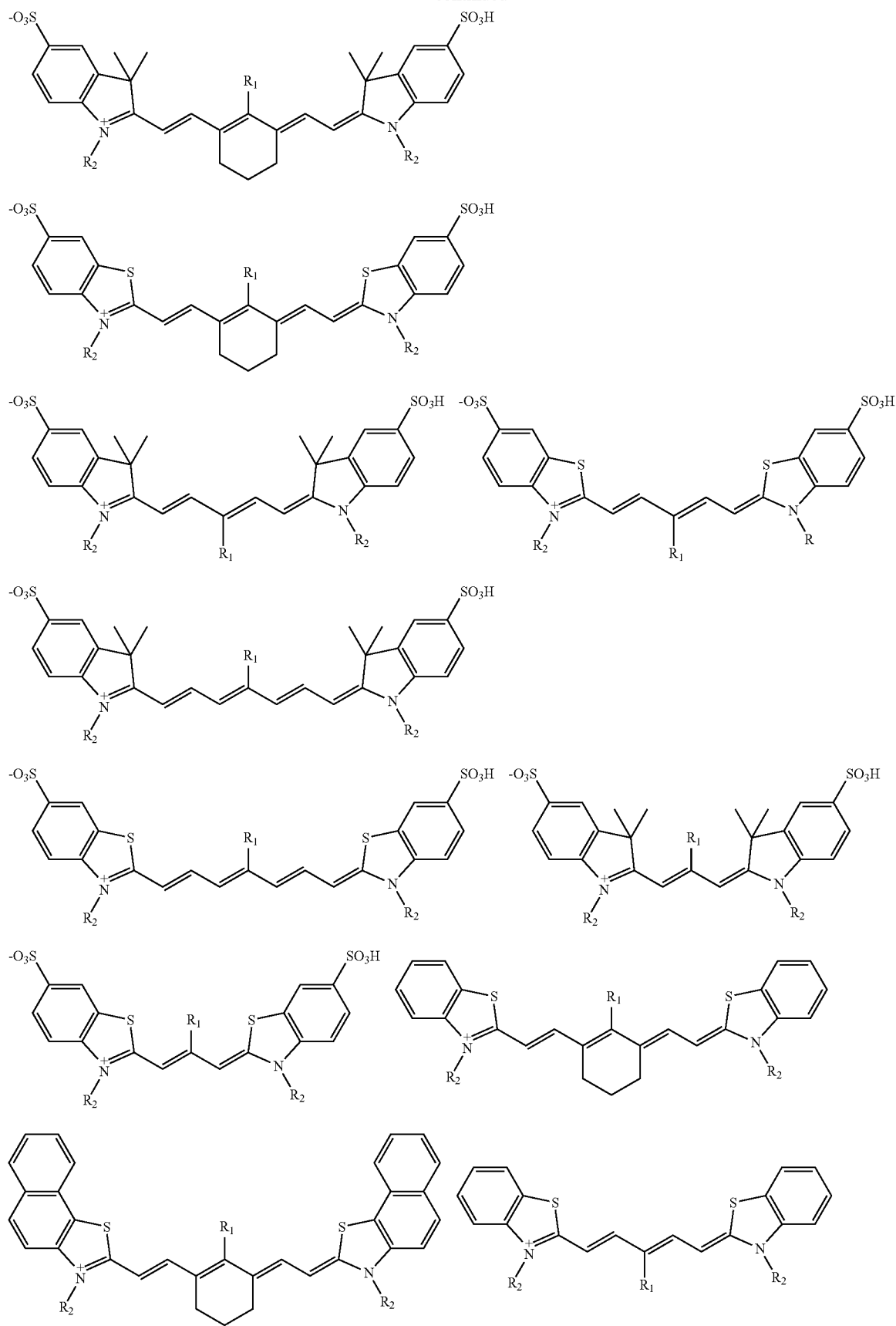

-continued
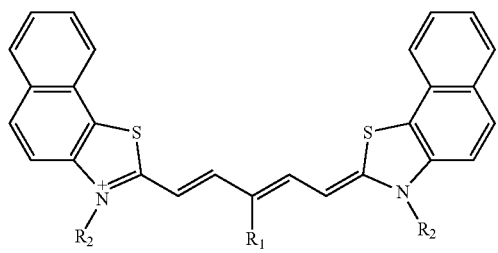
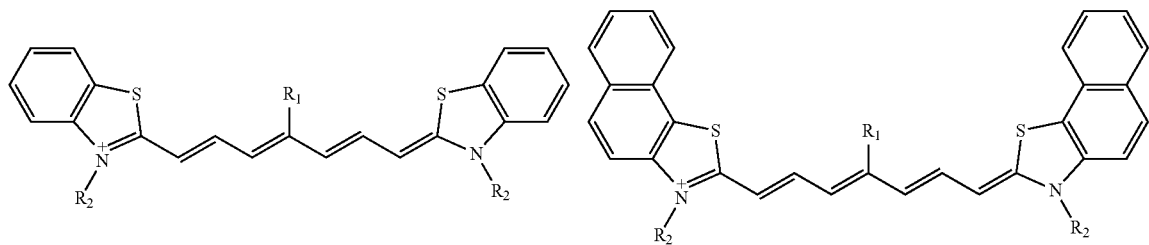
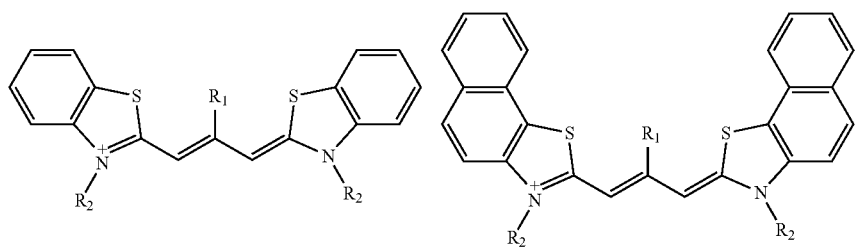
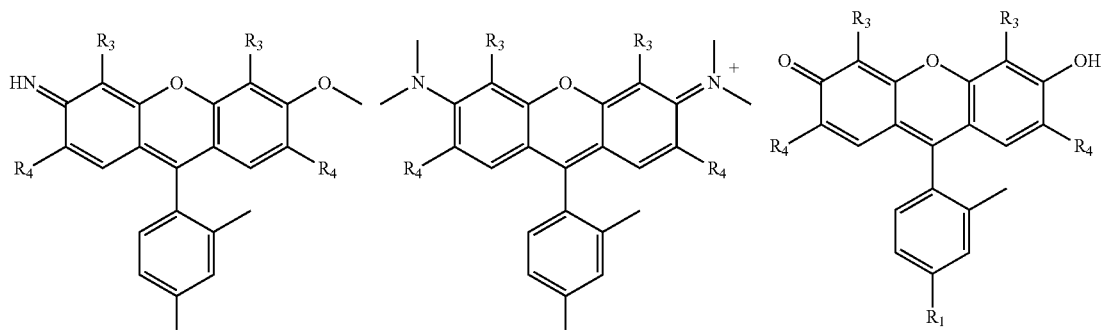
R₃: H, Me, F, Cl, Br
R₄: H, Me, F, Cl, Br
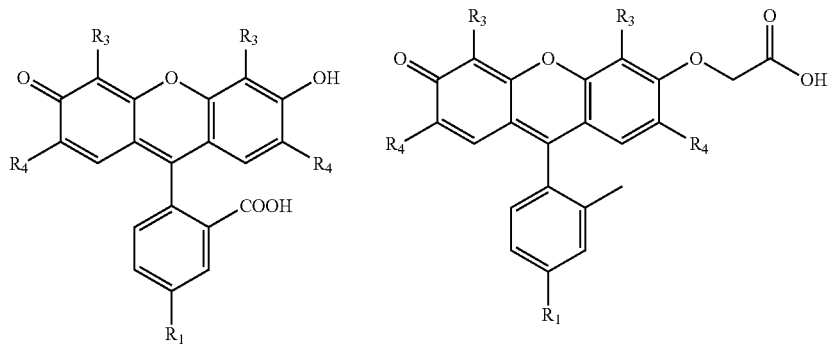

-continued
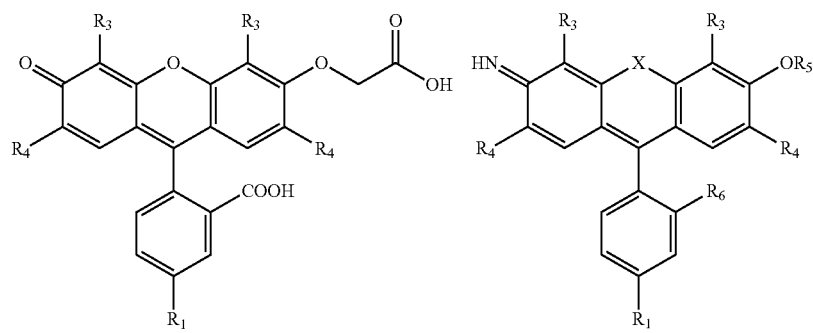
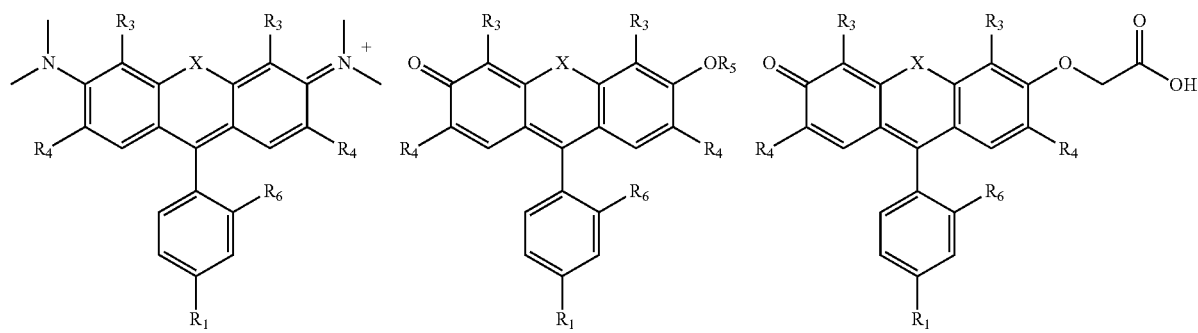
$R_3$: H, Me, F, Cl, Br
$R_4$: H, Me, F, Cl, Br
$R_5$: H, alkyl, alkoxy, carboxylate, ester, amide, carbamate, etc...
$R_6$: $CH_3$, $CO_2H$, $CH_2OH$
X: O, $SiMe_2$
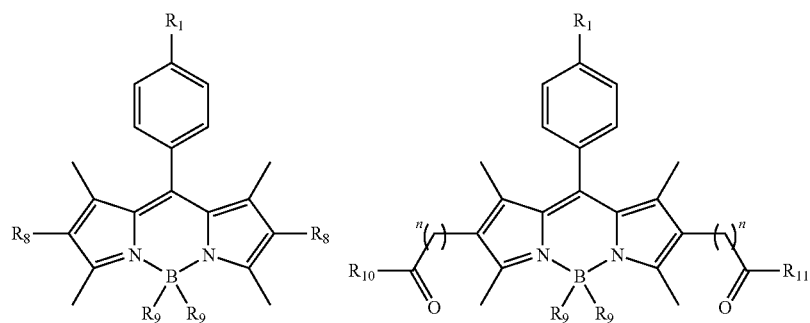
$R_8$ = H, alkyl, CN, Alkoxy
$R_9$ = F, OMe
$R_{10}$: H, alkyl, PEG, alkoxy, carboxylate etc . . .
$R_{11}$: H, alkyl, PEG, alkoxy, amide, carboxylate, SNAP tag, CLIP tag etc . . .
n = 1-12

Specific Examples:
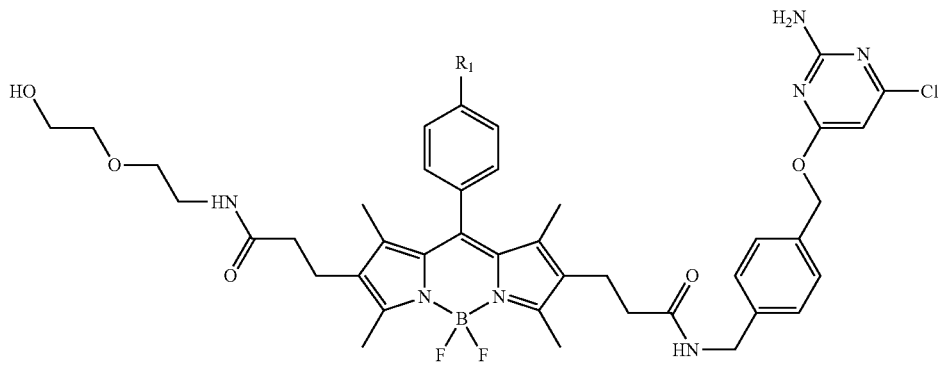
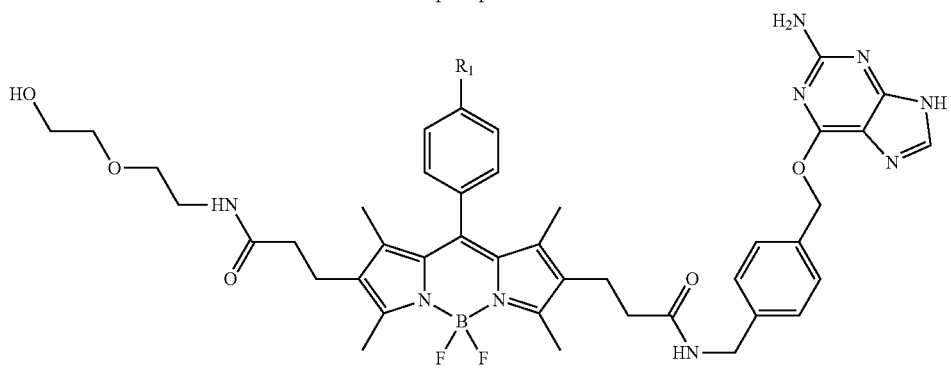
$R_{11}$: can also be the structures below
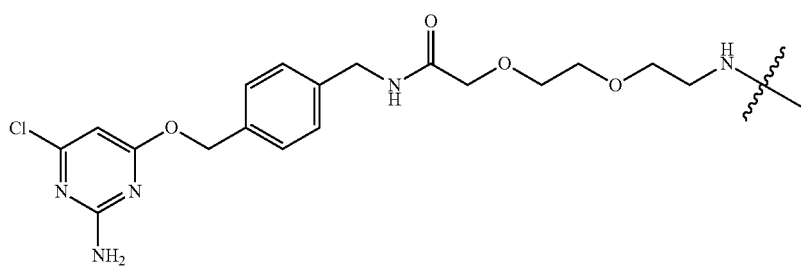
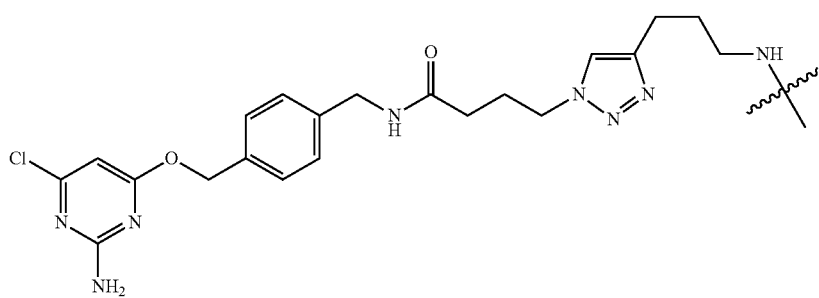
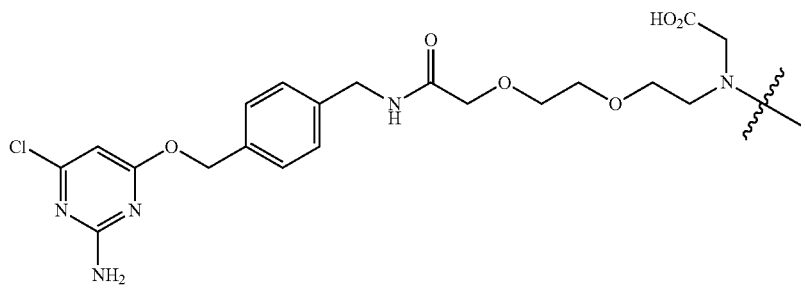

-continued
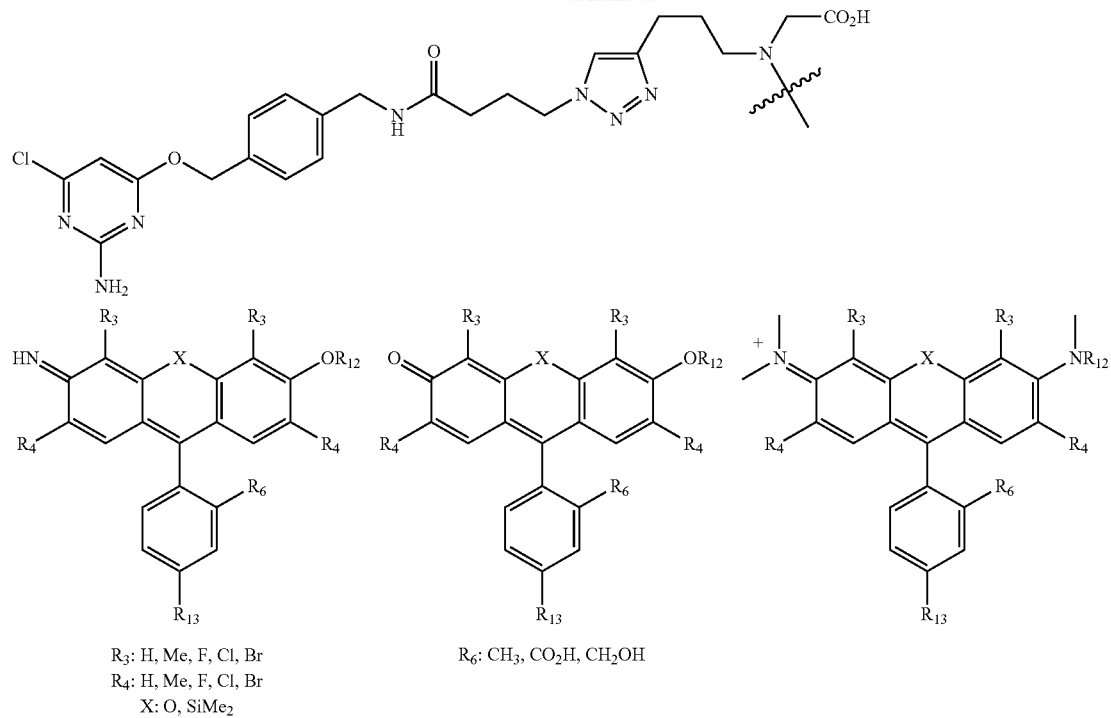
R$_3$: H, Me, F, Cl, Br
R$_4$: H, Me, F, Cl, Br
X: O, SiMe$_2$
R$_6$: CH$_3$, CO$_2$H, CH$_2$OH
R$_{12}$:
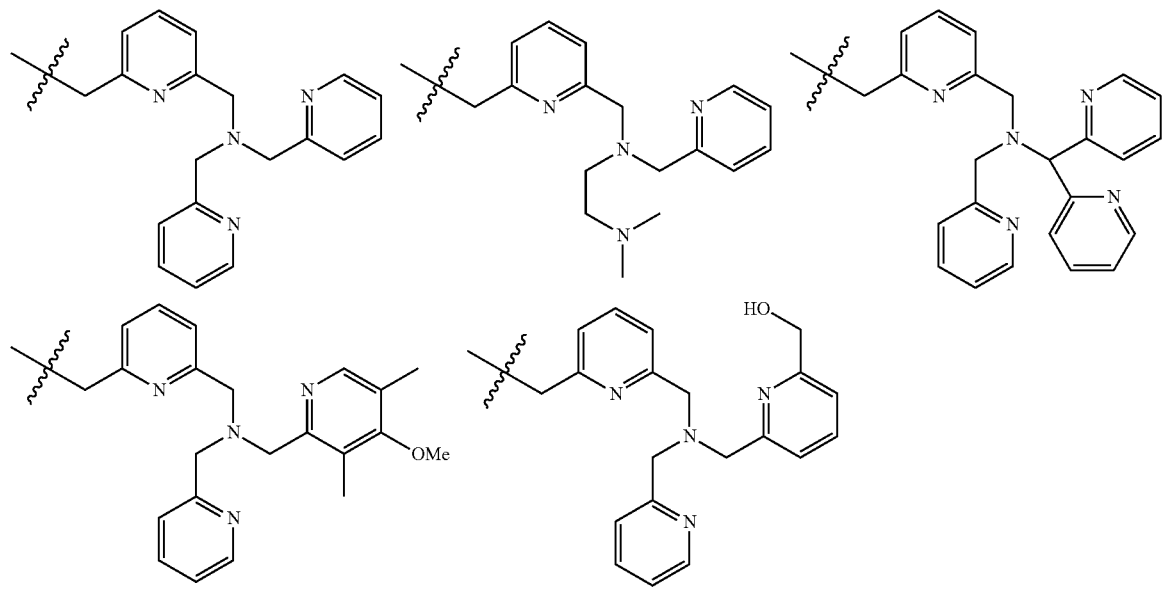
R$_{13}$: CH$_3$, CO$_2$H, CH$_2$OH, OH, OMe, H, PEG, alkyl, carboxyl, carbamyl, amide, and examples below
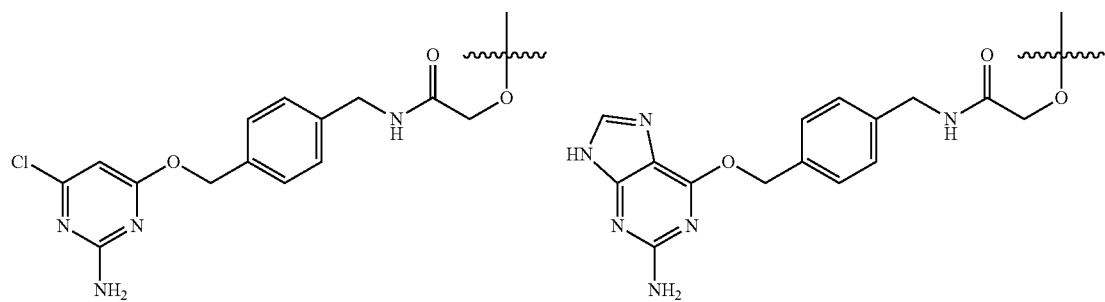

-continued
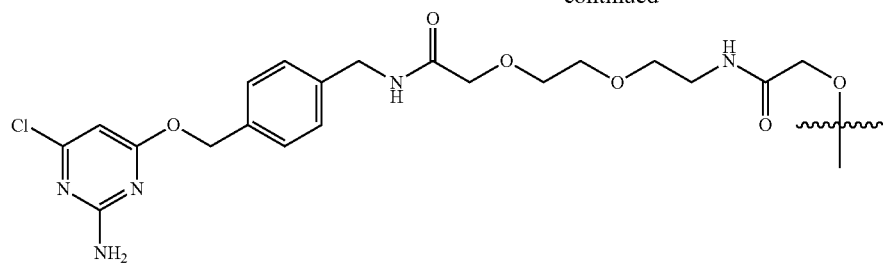
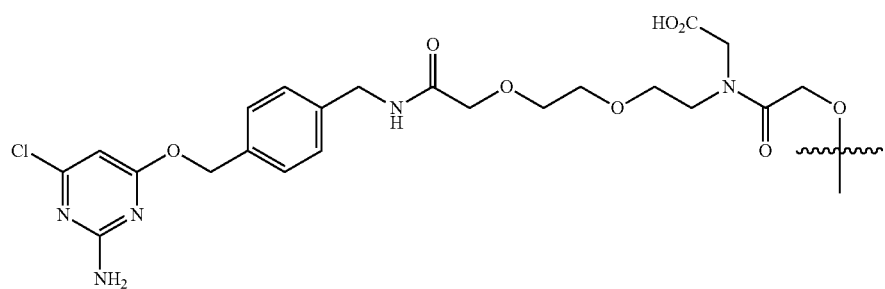
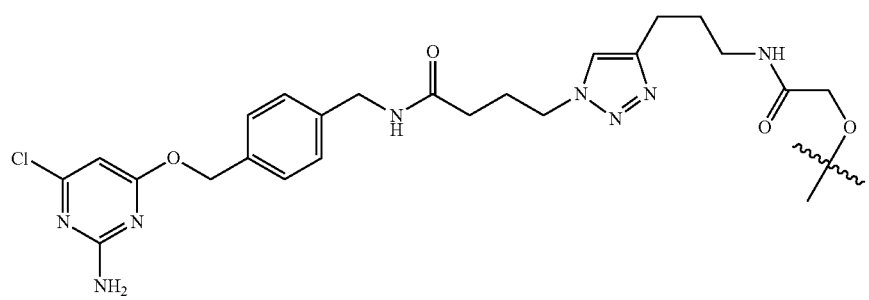
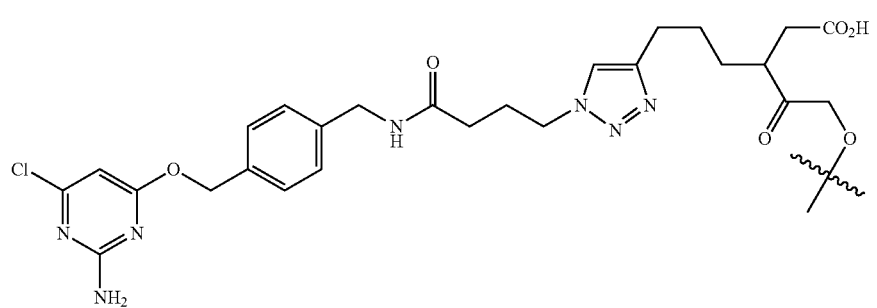
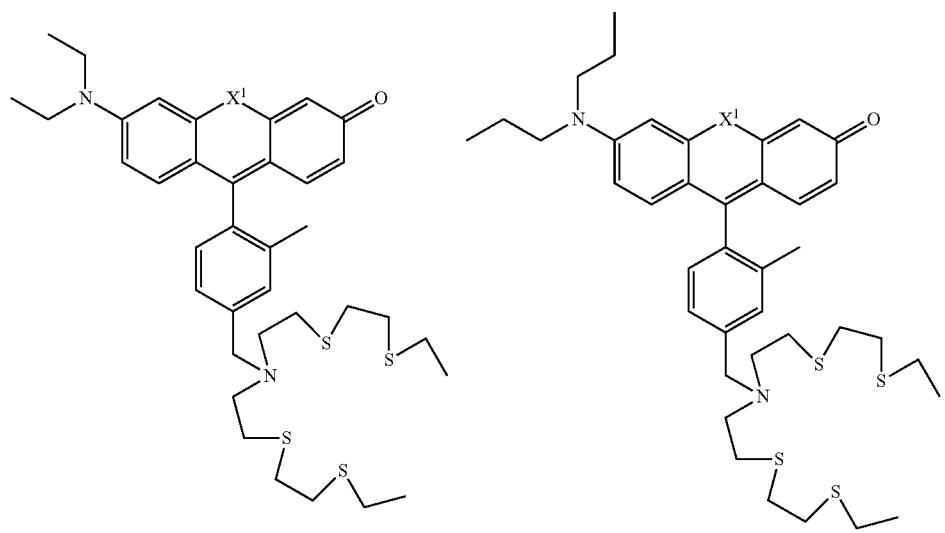

63
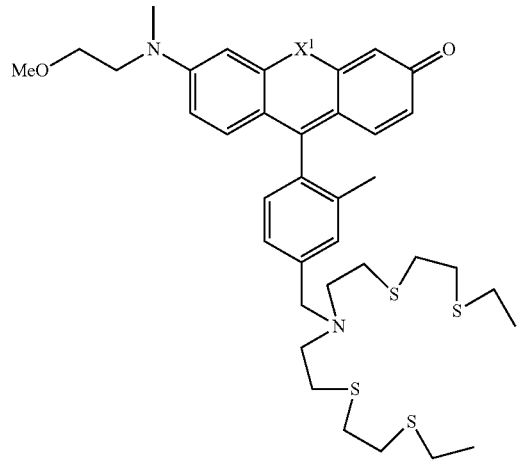
64
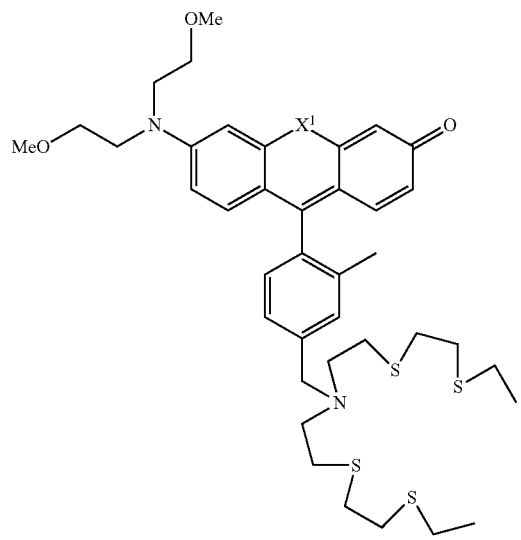
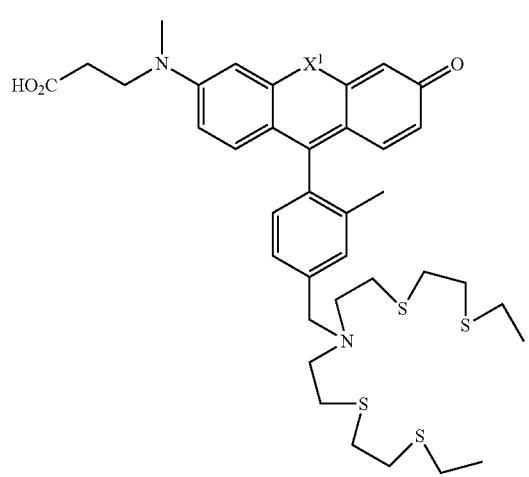
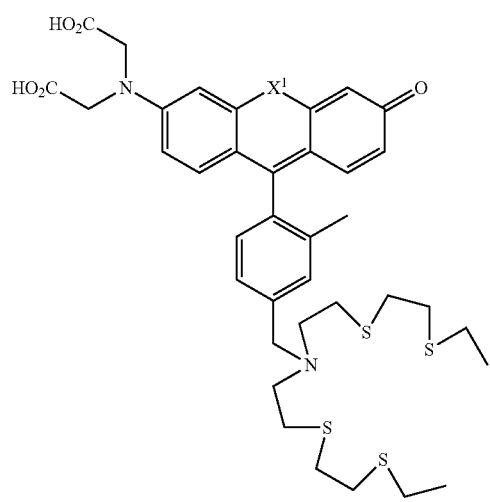
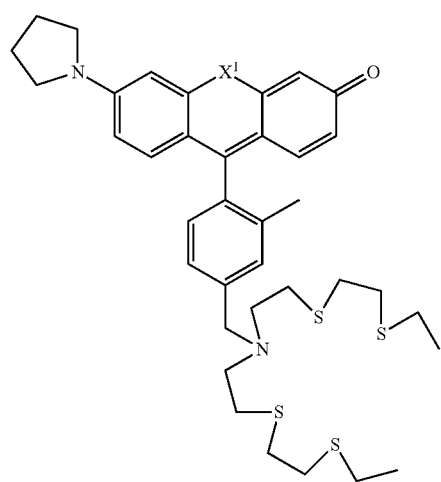
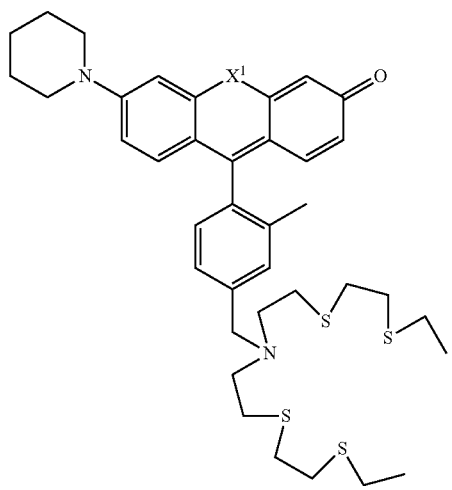

-continued

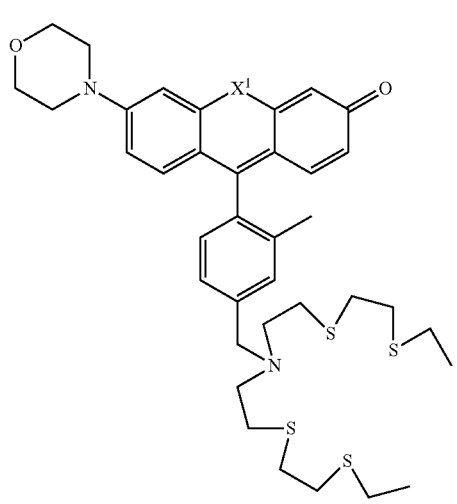

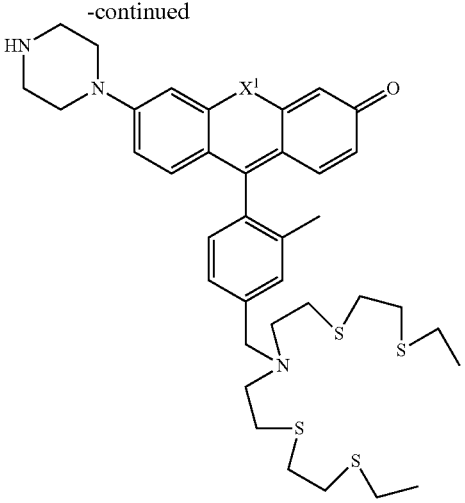

X = Si(CH$_3$)$_2$, C(CH$_3$)$_2$, O.

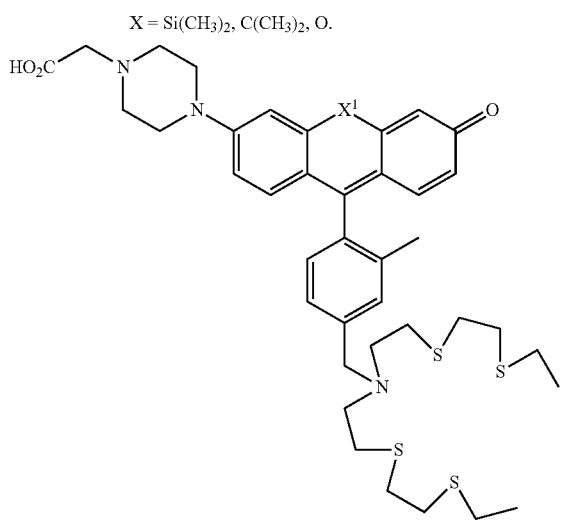

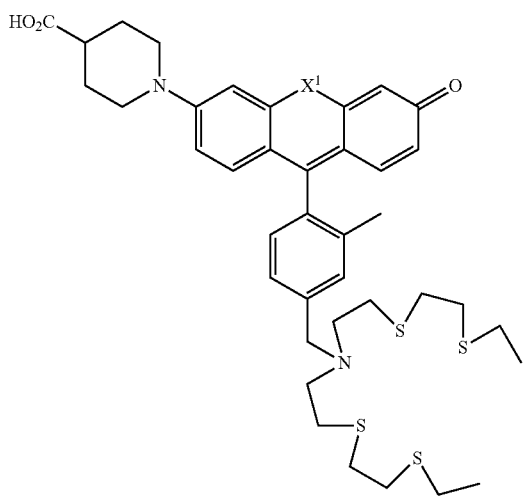

Methods (Binding-Based Probes)

The following methods pertain to binding-based probes, such as compounds according to formulae 1, 2, 3, and 7.

In one aspect, the invention provides a method of detecting a metal ion in a sample or in a subject comprising: (a) contacting the metal ion with a compound disclosed herein to form a complex in the sample or in the subject; (b) exciting the complex with light to cause the complex to undergo emission and (c) detecting the emission.

In some embodiments, the method is repeated to determine changes in a level of the metal ion in the sample or in the subject over time. In some embodiments, the method is repeated to determine changes in a level of the metal ion in the subject that result from administration of different drugs, a change in diet, or alterations in the environment that the subject is in.

In some embodiments, the emission is stronger than the emission from the compound excited in the absence of complexation with the metal ion.

In some embodiments, the method is performed in vivo. In some embodiments, the method is performed in vitro.

In some embodiments, the sample comprises a cell, and the complex is formed within the cell. In some embodiments, the sample comprises extracellular matrix. In some embodiments, the complex is formed within the extracellular matrix.

In some embodiments, the sample comprises blood. In some embodiments, the complex is formed within the blood.

In one aspect, the invention provides a method of diagnosing or staging a disease comprising: (a) administering a plurality of a compound disclosed herein to a subject, wherein the plurality of the compound forms a plurality of a complex with a metal ion; (b) exciting the plurality of the complex with light to cause the plurality of the complex to undergo emission; (c) detecting the emission; and (d) comparing the emission with a reference value. In some embodiments, the method further comprises repeating steps (a)-(c) with respect to a subject without or experiencing a lesser stage of the disease to provide the reference value.

In some embodiments, the disease is characterized by a change in level or localization of the metal ion in the subject as compared to a subject without or experiencing a lesser stage of the disease. In some embodiments, the disease is selected from Menkes disease, Wilson's disease, heart disease, anemia, cancer, and neurodegenerative disease.

In one aspect, the invention provides a method of determining efficacy of a treatment to a subject comprising: (a) administering a plurality of a compound disclosed herein to a subject, wherein the plurality of the compound forms a plurality of a complex with a metal ion; (b) exciting the plurality of the complex with light to cause the plurality of the complex to undergo a first emission; (c) detecting the first emission; (d) administering the treatment to the subject; (e) exciting the plurality of the complex with light to cause the plurality of the complex to undergo a second emission; (f) detecting the second emission; and (g) comparing the first emission and the second emission.

In some embodiments, the method is repeated to determine changes in a level of the metal ion in the subject over time.

In some embodiments, the metal ion is a copper ion.

In some embodiments, an emission is near infrared emission.

In some embodiments, the subject is an animal. In some embodiments, the subject is a mammal. In some embodiments, the subject is a human.

Methods (Reaction-Based Probes)

The following methods pertain to reaction-based probes, such as compounds according to formulae 4, 5 and 6.

In one aspect, the invention provides a method of detecting a metal ion in a sample or in a subject comprising: (a) contacting the metal ion with a compound disclosed herein to form a complex in the sample or in the subject, wherein after the complex is formed, a bond cleavage occurs within the compound, forming a cleavage product; (b) exciting the cleavage product with light to cause the cleavage product to undergo emission and (c) detecting the emission.

In some embodiments, the bond cleavage occurs in the presence of oxygen.

In some embodiments, the method is repeated to determine changes in a level of the metal ion in the sample or in the subject over time. In some embodiments, the method is repeated to determine changes in a level of the metal ion in the subject that result from administration of different drugs, a change in diet, or alterations in the environment that the subject is in.

In some embodiments, the emission of the cleavage product is stronger than the emission from the compound excited in the absence of complexation with the metal ion and subsequent bond cleavage.

In some embodiments, the method is performed in vivo. In some embodiments, the method is performed in vitro.

In some embodiments, the sample comprises a cell, and the complexation and bond cleavage occur within the cell. In some embodiments, the sample comprises extracellular matrix. In some embodiments, the complexation and bond cleavage occur within the extracellular matrix. In some embodiments, the sample comprises blood. In some embodiments, the complexation and bond cleavage occur within the blood.

In one aspect, the invention provides a method of diagnosing or staging a disease comprising: (a) administering a plurality of a compound disclosed herein to a subject, wherein the plurality of the compound forms a plurality of a complex with a metal ion, wherein after the plurality of the complex is formed, bond cleavage occurs within the plurality of the compound, forming a plurality of a cleavage product; (b) exciting the plurality of the cleavage product with light to cause the plurality of the cleavage product to undergo emission; (c) detecting the emission; and (d) comparing the emission with a reference value. In some embodiments, the method further comprises repeating steps (a)-(c) with respect to a subject without or experiencing a lesser stage of the disease to provide the reference value.

In some embodiments, the disease is characterized by a change in level or localization of the metal ion in the subject as compared to a subject without or experiencing a lesser stage of the disease. In some embodiments, the disease is selected from Menkes disease, Wilson's disease, heart disease, anemia, cancer, and neurodegenerative disease.

In one aspect, the invention provides a method of determining efficacy of a treatment to a subject comprising: (a) administering a first plurality of a compound disclosed herein to a subject, wherein the first plurality of the compound forms a first plurality of a complex with a metal ion, wherein after the first plurality of the complex is formed, bond cleavage occurs within the first plurality of the compound, forming a first plurality of a cleavage product; (b) exciting the first plurality of the cleavage product with light to cause the first plurality of the cleavage product to undergo a first emission; (c) detecting the first emission; (d) administering the treatment to the subject; (e) after clearance of the first plurality of the cleavage product from the subject, administering a second plurality of the compound disclosed herein to the subject, wherein the second plurality of the compound forms a second plurality of a complex with a metal ion, wherein after the second plurality of the complex is formed, bond cleavage occurs within the second plurality of the compound, forming a second plurality of a cleavage product; (f) exciting the second plurality of the cleavage product with light to cause the second plurality of the cleavage product to undergo a second emission; (g) detecting the second emission; and (h) comparing the first emission and the second emission.

In some embodiments, the method further comprises repeating steps (e) to (h) after clearance of the cleavage product from the subject. In some embodiments, steps (e) to (h) are repeated one, two, three, four, five, six, seven, eight, nine, or ten times.

In some embodiments, the method is repeated to determine changes in a level of the metal ion in the subject over time.

In some embodiments, the metal ion is a copper ion.

In some embodiments, an emission is near infrared emission.

In some embodiments, the subject is an animal. In some embodiments, the subject is a mammal. In some embodiments, the subject is a human.

General Synthesis Schemes

A general scheme is provided for synthesis of CS790AM:

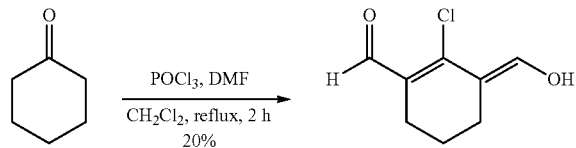

-continued
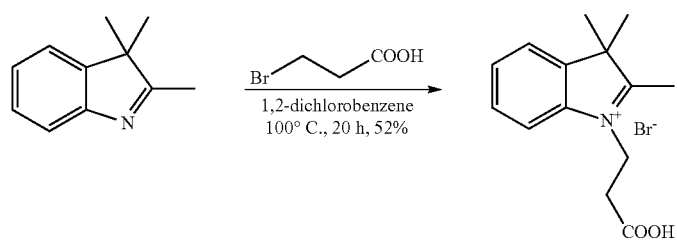
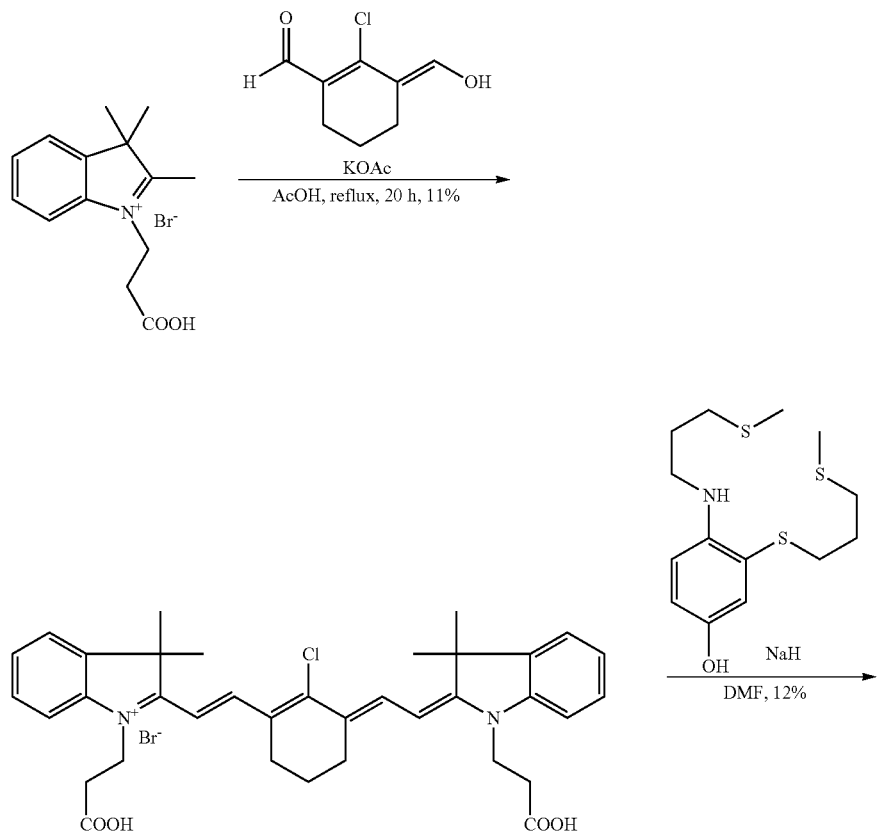
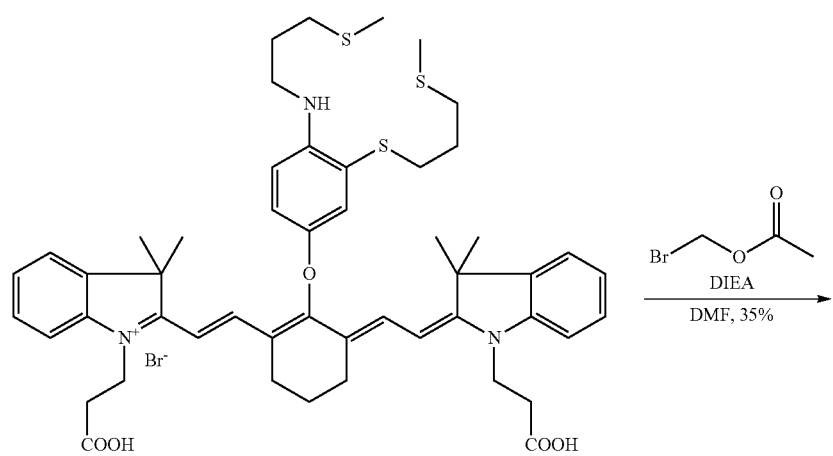

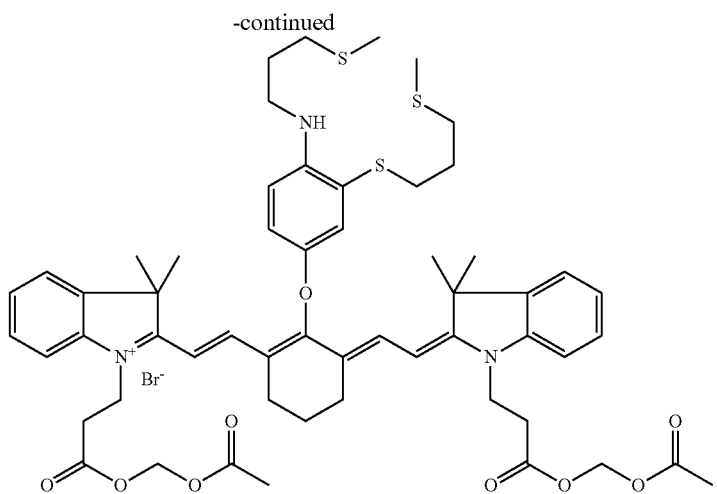
A general scheme is provided for synthesis of CS788
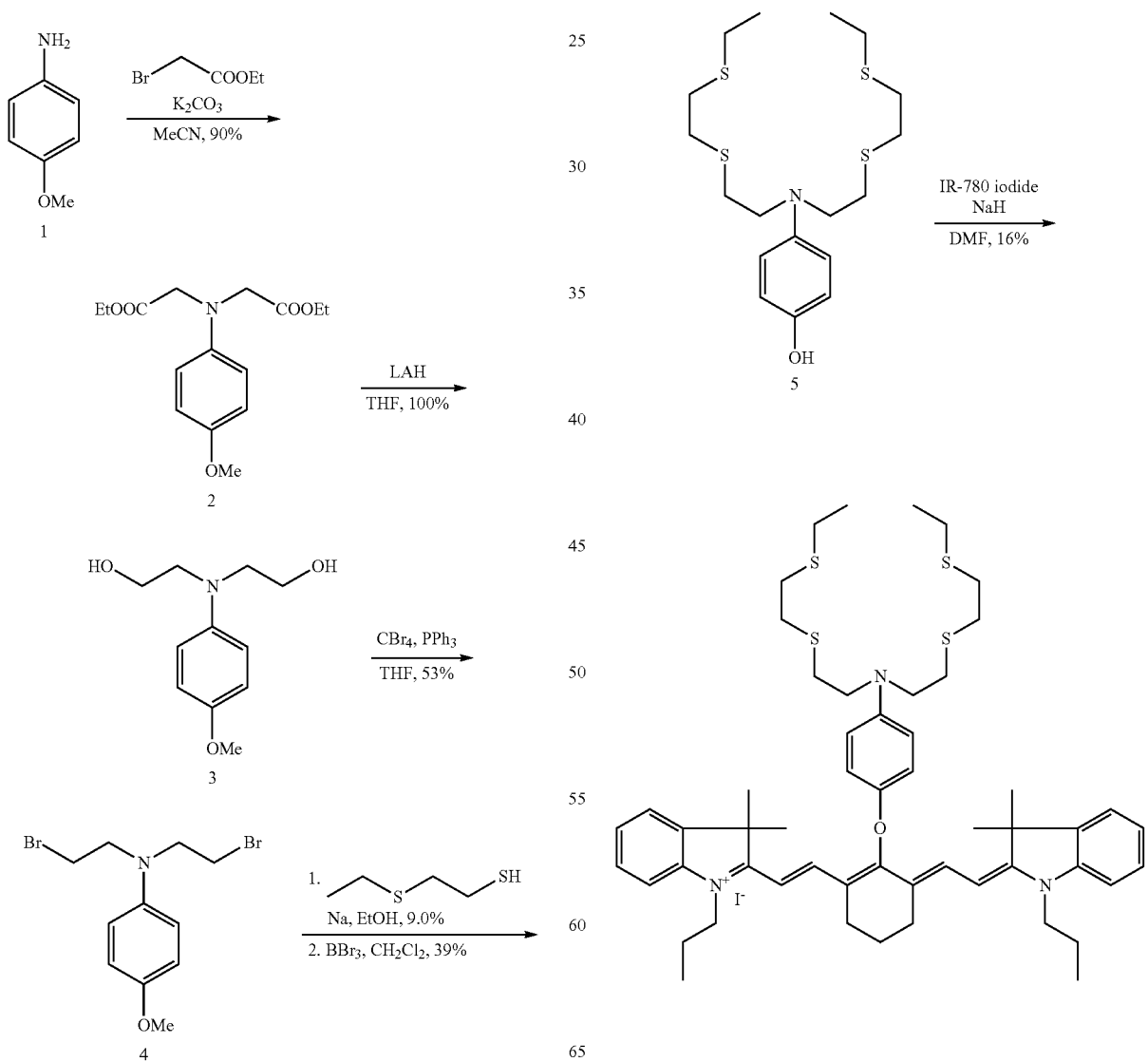
A general scheme is provided for synthesis of Tokyo Green-based compounds:

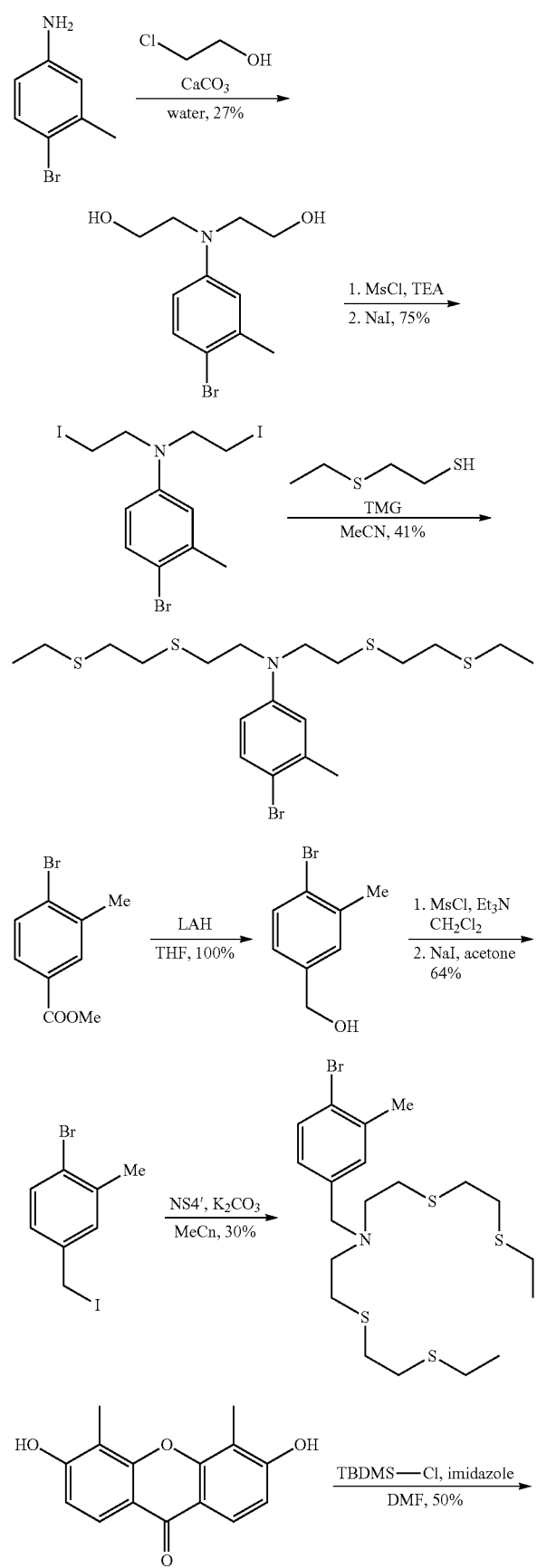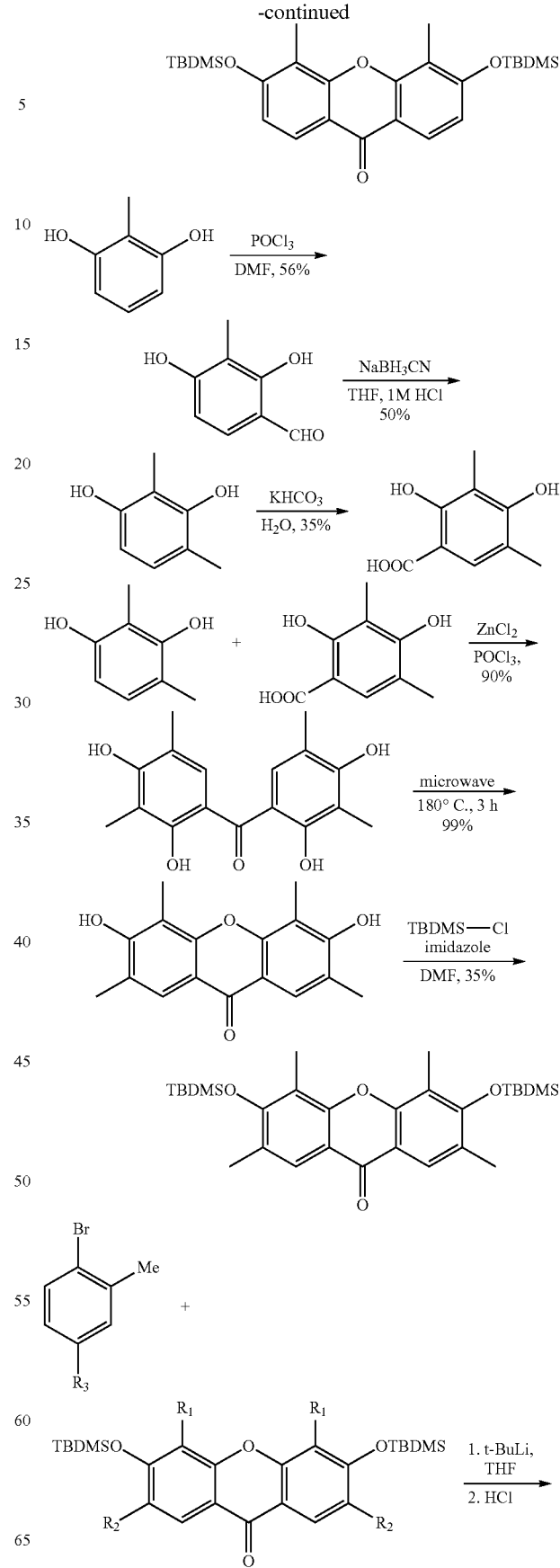

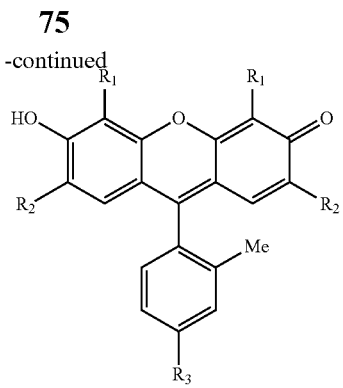
A general scheme is provided for synthesis of CS7:
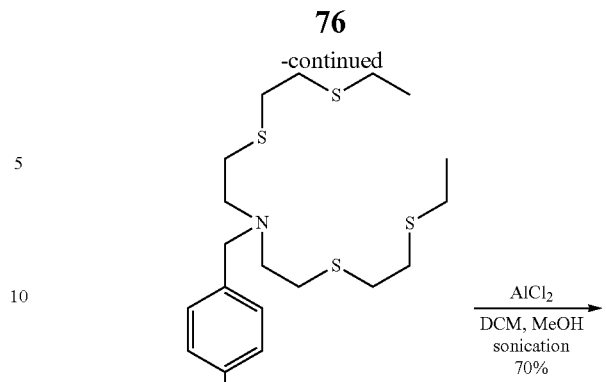
A general scheme is provided for the synthesis of an exemplary reaction-based probe according to Formula 5 and its cleavage reaction after complexation with Cu(I):
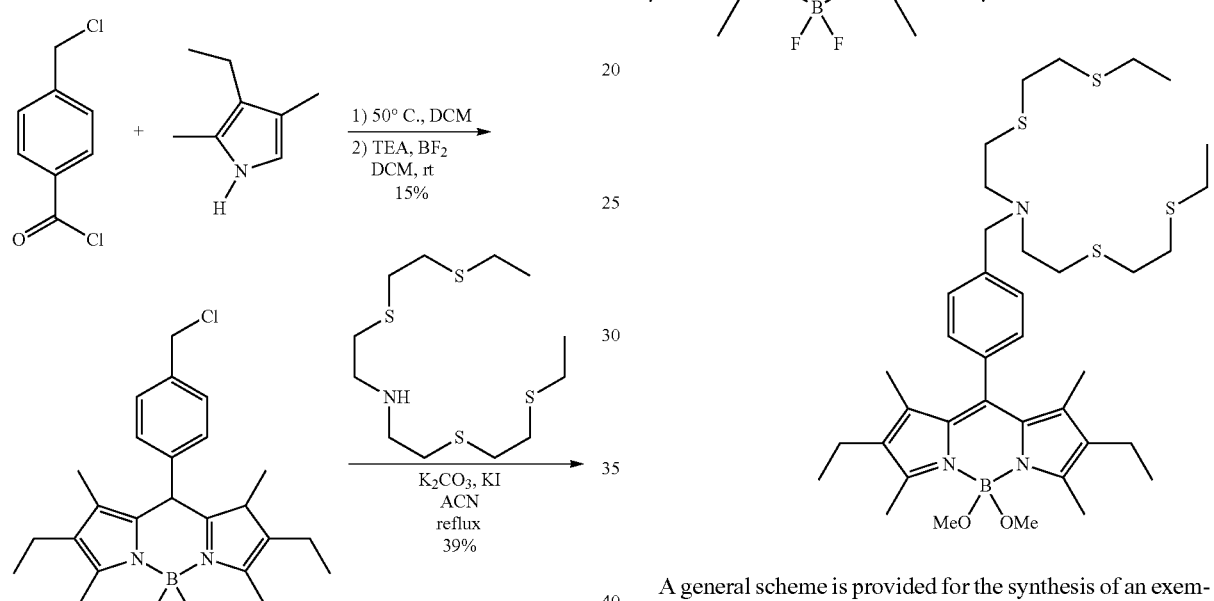
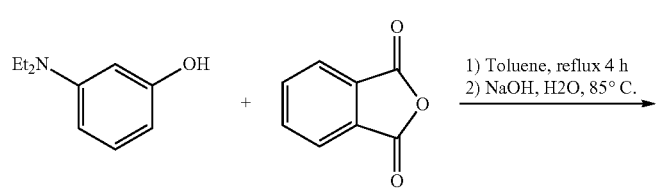
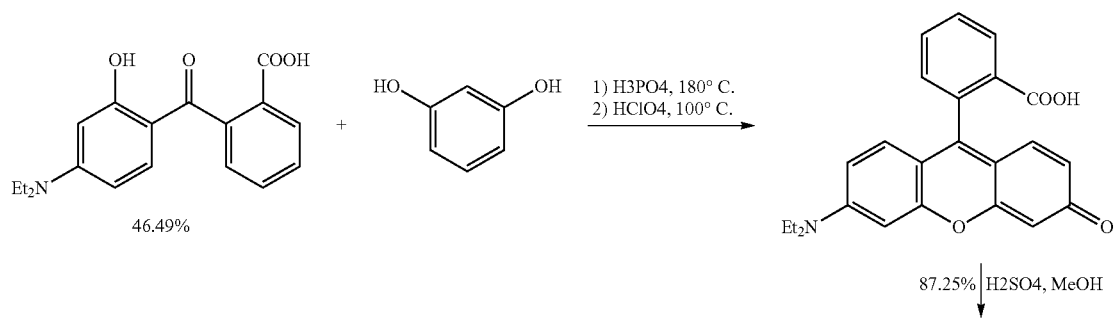

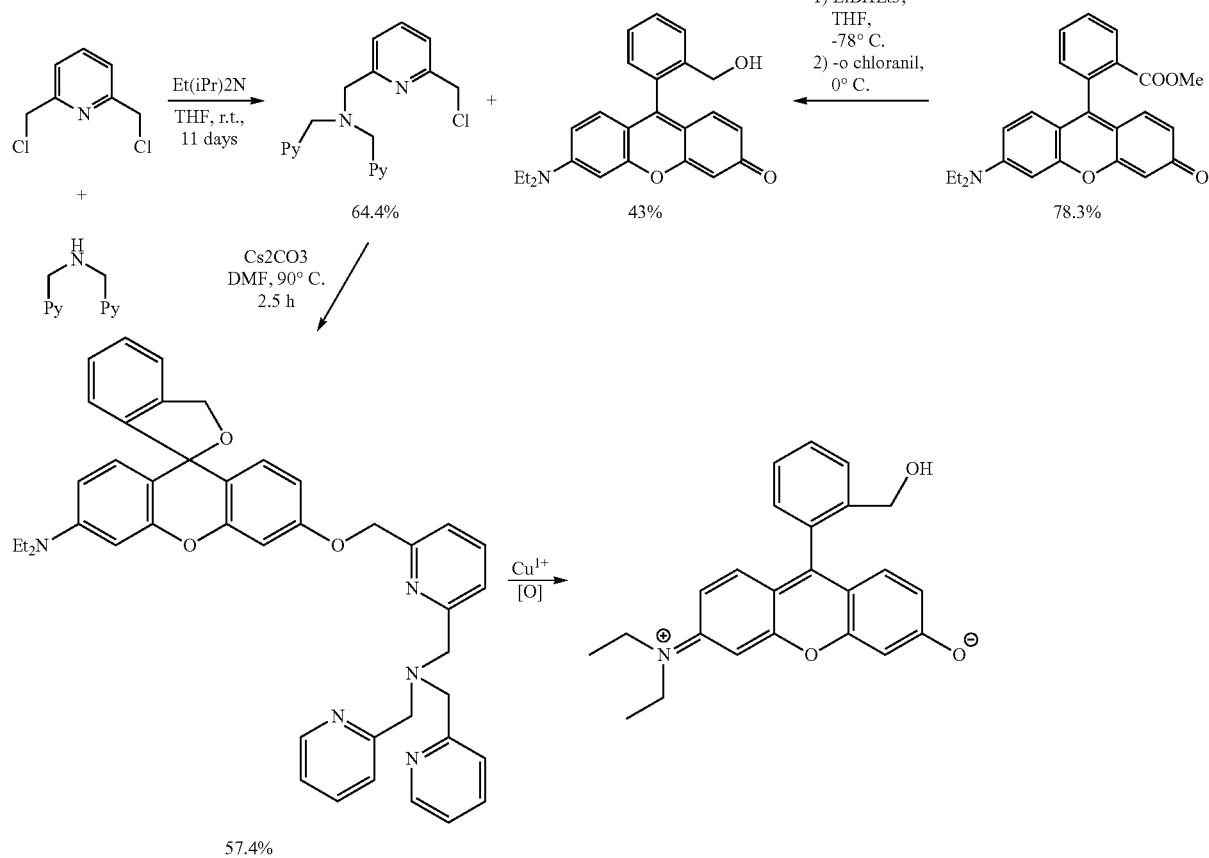
A general scheme is provided for the synthesis of an exemplary binding-based probe according to Formula 2 (wherein $X^1$ is $Si(R^{32})(R^{33})$):
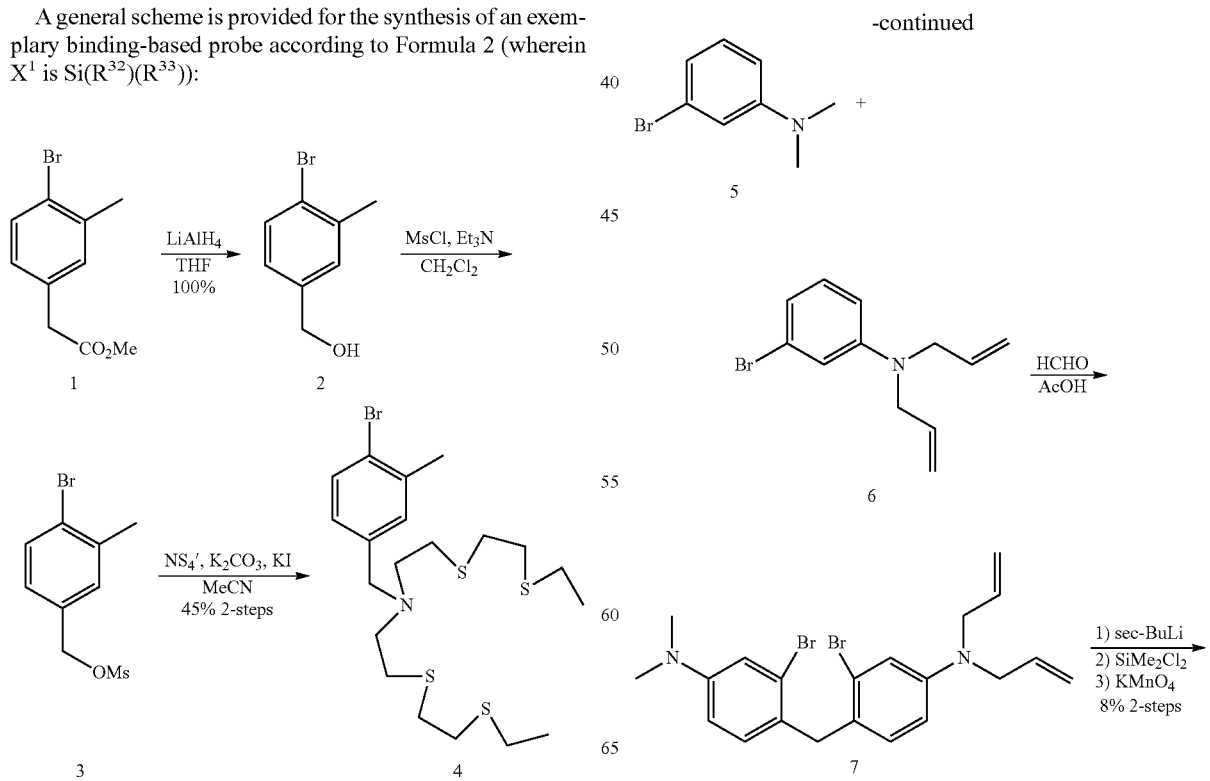

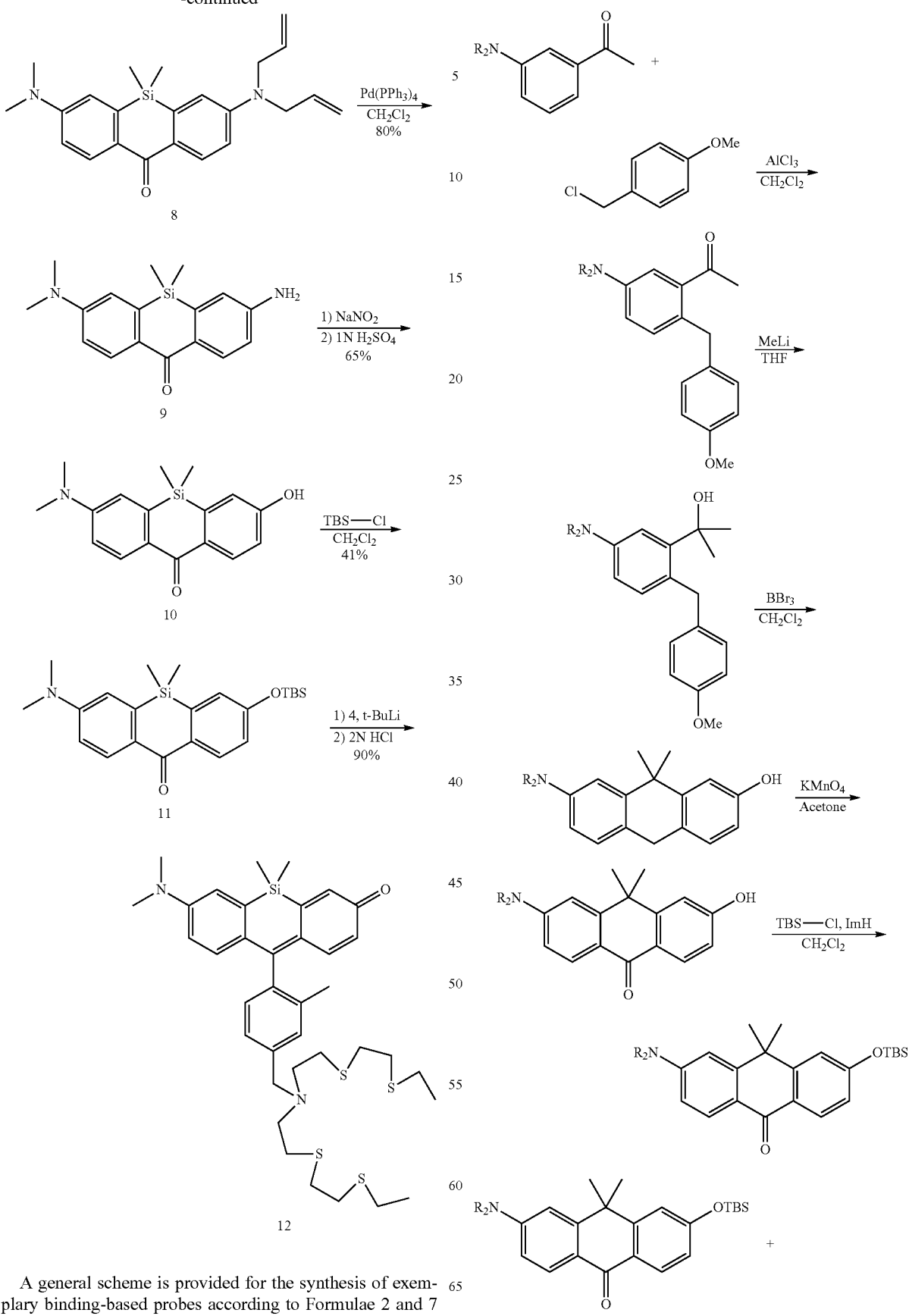
A general scheme is provided for the synthesis of exemplary binding-based probes according to Formulae 2 and 7 (wherein $X^1$ is $C(R^{32})(R^{33})$):

-continued
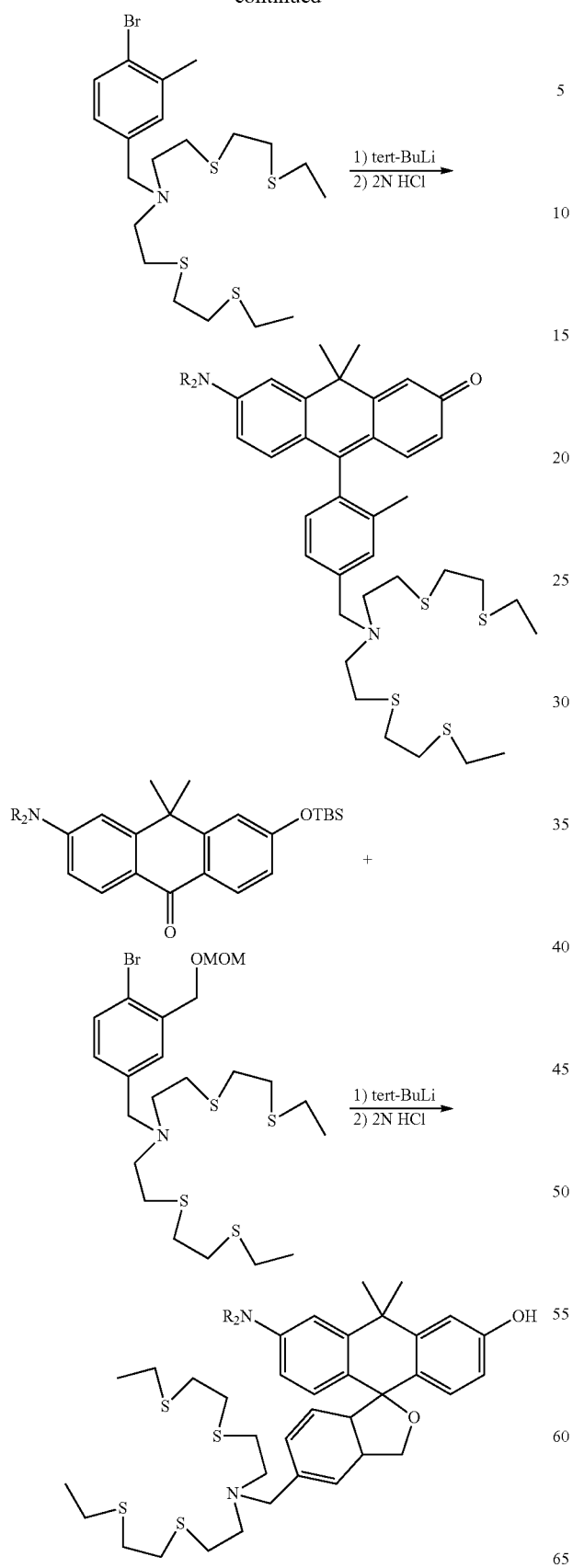
A general scheme is provided for the synthesis of an exemplary binding-based probe according to Formula 2 (wherein $X^1$ is $Sn(R^{32})(R^{33})$, $B(R^{32})(R^{33})$, S, Se, or Te):
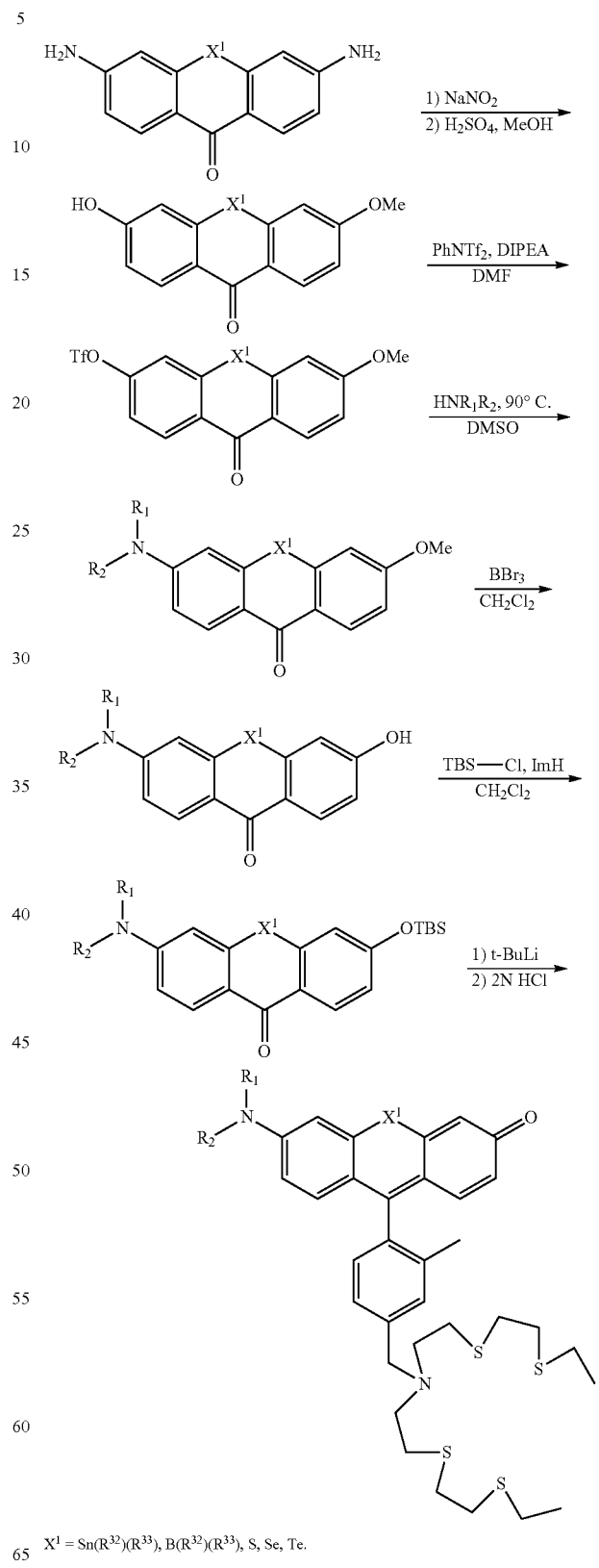
$X^1 = Sn(R^{32})(R^{33})$, $B(R^{32})(R^{33})$, S, Se, Te.

Detection in Cells and Animals

The copper sensing compounds can be used to look at changes in copper in cells, and especially in animals. In cells, the invention can be used to detect changes in the level of copper. For example, we have used these sensors to detect changes in copper levels in the presence of exogenous copper and the presence of chelators. Furthermore, with confocal microscopy, we should be able to use these sensors to look at copper relocation in cells. In animals, the best way to use the sensors is to use them to detect changes in copper levels or localization in the animals as a result of injection with compounds or as a result of the development of progression of a disease. In our experiments, we have demonstrated that addition of exogenous copper increases the signal that is seen from mice injected with the copper sensors and that injection with a copper chelator attenuates the signal increase seen with exogenous copper injection. Furthermore, mice injected with a copper chelator have a decreased signal from the copper sensors compared with mice that are not injected with the chelator. This indicates that we can detect endogenous levels of copper in mice, and suggests that the copper sensors can be used to detect relocation of copper or changes in basal levels of copper during experiments. For instance, the sensors could be used to look for changes in copper levels when animals are put on a calorie restricted or high fat diet. The sensors should also be useful for monitoring changes in the level of copper that result from injection of different drugs, a change in diet, or alterations in the environment that the animal is in. The sensors will also be useful for monitoring copper levels during disease progression in animals. There are many diseases that are linked to changes in copper, such as Menkes disease, Wilson's disease, heart disease, anemia, cancer, and neurodegenerative diseases. The sensors presented in this invention will be useful for studying all of these diseases, as well as various other diseases that are found to have alterations in copper levels or localization in the future. The copper sensors are especially useful for monitoring diseases because they are non-toxic and can be cleared from the body quickly, which means that the sensors can be used to monitor the development and/or progression of a particular disease(s) in one animal. This is a large benefit over many other methods for monitoring disease because other methods usually require sacrifice of the animals, followed by measurement of the analyte (which is copper in the case of the sensors in this invention). With the copper sensors, the analyte (copper) can be measured in the context of a whole, living organism.

EXAMPLES

In the examples that follow, it should be apparent that compound numbering refers to compounds within each particular example.

Example 1

Synthesis of CS790AM

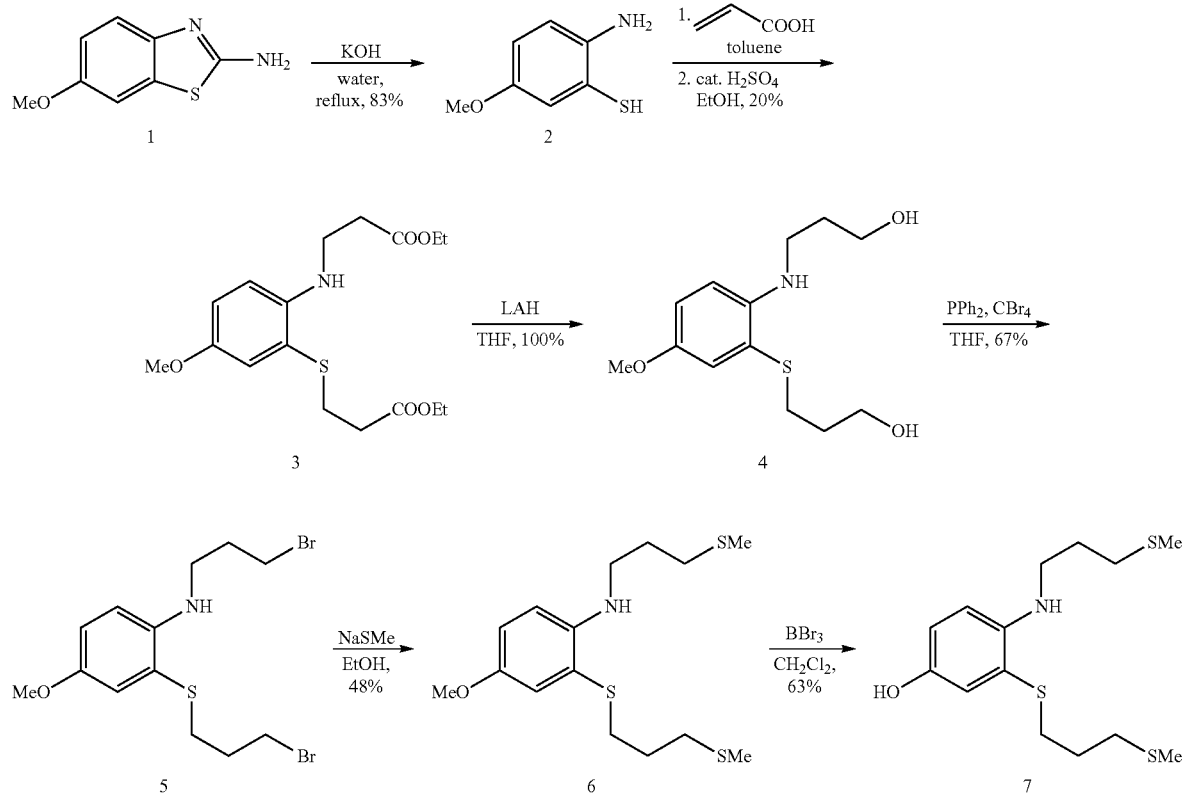

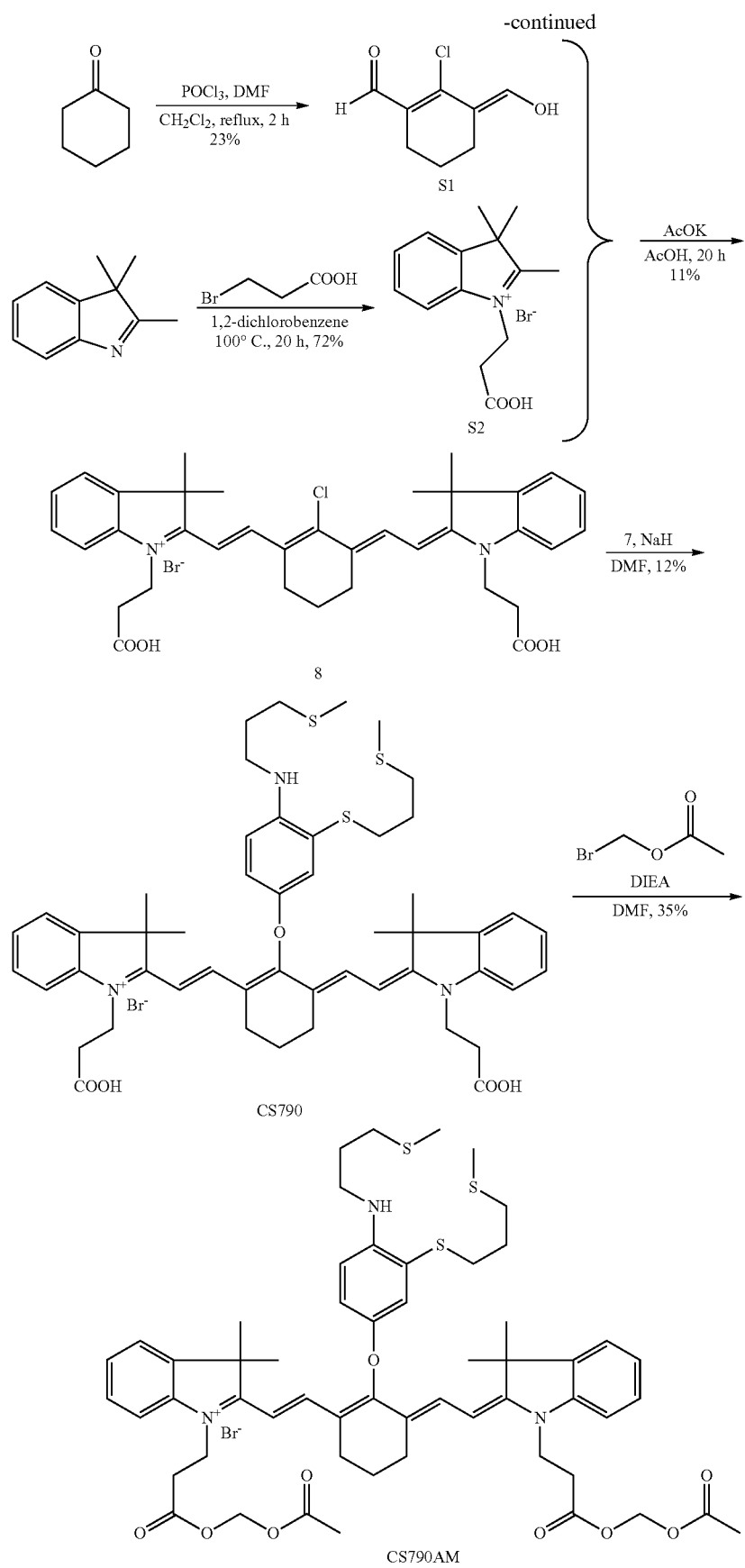

2-amino-5-methoxy-thophenol (2)

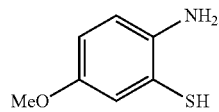

2-Amino-6-methoxy-benzothiazole (6.0 g, 33.3 mmol) was suspended in 50% KOH (30 g KOH dissolved in 30 mL water). The suspension was heated to reflux for 48 h. After cooling to room temperature, toluene (100 mL) was added and the reaction mixture was neutralized with acetic acid (30 mL). The organic layer was separated, and the aqueous layer was extracted with toluene (100 mL). The toluene layers were combined and washed with water and dried over $Na_2SO_4$. Evaporation of the solvent gave the title product (4.3 g, 83%) as yellow solid. $^1$H-NMR (acetone-$d_6$, 400 MHz): δ6.66 (1H, d, J=2.6 Hz), 6.57 (1H, d, J=8.5 Hz), 6.43 (1H, dd, J=8.5, 2.6 Hz), 3.70 (3H, s).

N,S-di-(2-ethoxycarbonylethyl)-2-amino-5-methoxy-thophenol (3)

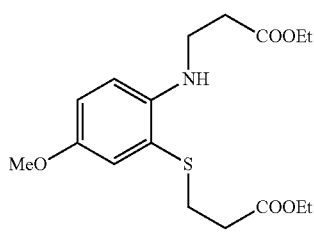 [SMILES: CCOC(=O)CCNc1ccc(OC)cc1SCCC(=O)OCC]

To a solution of 2 (2.5 g, 16.1 mmol) in toluene (15 mL) was added acrylic acid (3.3 g, 35.4 mmol). The mixture was refluxed for 3 h, and then the solvent was evaporated. The residue was washed with ether (30 mL) and then dried in vacuo. Ethanol (30 mL) and conc. $H_2SO_4$ (0.5 mL) was added to the residue, and the mixture was refluxed for 24 h. After concentrating to ~5 mL, the mixture was suspended with water (80 mL). Saturated sodium bicarbonate solution (20 mL) was added to the mixture, and then the mixture was extracted with AcOEt (50 mL×3). The combined organic layers were dried over $Na_2SO_4$ and then evaporated. Purification by silica gel column chromatography (AcOEt-hexane, 1:2) afforded the title compound (1.2 g, 20%). $^1$H-NMR (CDCl$_3$, 400 MHz): δ7.03 (1H, d, J=3.0 Hz), 6.85 (1H, dd, J=8.8, 3.0 Hz), 6.61 (1H, d, J=8.8 Hz), 4.20-4.11 (4H, m), 3.75 (3H, s), 3.46 (2H, t, J=6.6 Hz), 2.95 (2H, t, J=7.3 Hz), 2.64 (2H, t, J=6.6 Hz), 2.53 (1H, d, J=7.3 Hz), 1.29-1.24 (6H, m). $^{13}$C-NMR (CDCl$_3$, 100 MHz) δ 172.2, 171.8, 151.1, 143.3, 121.8, 117.7, 116.4, 111.4, 60.6, 55.9, 40.0, 34.5, 34.1, 29.5, 14.2, 14.1. LRMS (ESI): calculated for [(M+H)$^+$] 356.2. found 356.1.

N,S-di-(3-hydroxypropyl)-2-amino-5-methoxy-thophenol (4)

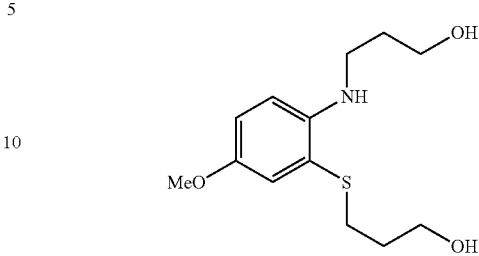

LiAlH4 (0.65 g, 17.1 mmol) was suspended in THF (30 mL) at 0° C. To the suspension was slowly added a solution of diester 3 (1.2 g, 3.4 mmol) in THF (5 mL). The mixture was refluxed for 20 h and then cooled to 0° C. Water (0.65 mL), 15% NaOH aqueous solution (0.65 mL), and water (20 mL) were successively added to the mixture to quench the excess LiAlH$_4$. The resulting insoluble material was removed by filtration with Celite, and the precipitation was washed by AcOEt (30 mL×5). The combined filtrate were washed with brine, and then dried over $Na_2SO_4$. After evaporation, the title compound 3 was obtained (0.93 g, 100%), and this was used to next step without further purification. $^1$H-NMR (CDCl$_3$, 400 MHz): δ7.06 (1H, d, J=3.0 Hz), 6.85 (1H, dd, J=8.8, 3.0 Hz), 6.66 (1H, d, J=8.8 Hz), 3.85 (2H, t, J=5.8 Hz), 3.78 (3H, s), 3.75 (2H, t, J=6.1 Hz), 3.30 (2H, t, J=6.4 Hz), 2.88 (2H, t, J=7.1 Hz), 1.96-1.92 (2H, m), 1.85-1.82 (2H, m). $^{13}$C-NMR (CDCl$_3$, 100 MHz) δ 151.3, 143.7, 121.0, 119.2, 115.7, 111.8, 61.6, 61.2, 56.0, 42.6, 32.1, 31.8, 31.4.

N,S-di-(3-bromopropyl)-2-amino-5-methoxy-thophenol (5)

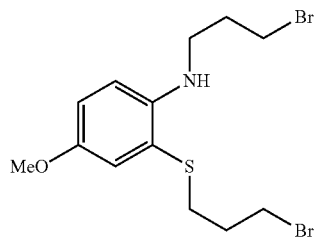 [SMILES: COc1ccc(NCCCBr)c(SCCCBr)c1]

To an ice-cooled solution of CBr$_4$ (3.5 g, 10.4 mmol) in THF (50 mL) was slowly added triphenylphosphine (2.7 g, 10.4 mmol). The mixture was stirred at room temperature for 10 min. After the color of the mixture turned to yellow, a solution of the diol 4 (0.95 g, 3.5 mmol) was slowly added to the mixture. After stirring under nitrogen atmosphere at room temperature for 6 h, the reaction mixture was filtered through Celite and the filtrate was evaporated. The residue was purified by column chromatography (AcOEt-hexane, 1:3) to give the title compound 5 (0.63 g, 53%) as yellow oil. $^1$H-NMR (CDCl$_3$, 400 MHz): δ7.05 (1H, d, J=3.0 Hz), 6.87 (1H, dd, J=8.8, 3.0 Hz), 6.66 (1H, d, J=8.8 Hz), 3.79 (3H, s), 3.58-3.54 (4H, m), 3.38 (2H, t, J=6.6 Hz), 2.93 (2H, t, J=6.9 Hz), 2.25-2.21 (2H, m), 2.14-2.07 (2H, m). $^{13}$C-NMR (CDCl$_3$, 100 MHz) δ 151.3, 143.1, 121.3, 118.2, 116.1, 111.7, 56.0, 42.8, 32.8, 32.1, 32.1, 31.2, 30.4.

N,S-di-(4-thiapentyl)-2-amino-5-methoxy-thophenol (6)

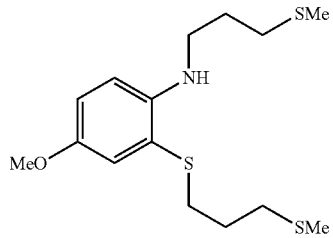 [SMILES: COc1ccc(NCCCSC)c(SCCCSC)c1]

Sodium thiomethoxide (0.85 g, 12.2 mmol) and compound 5 (1.2 g, 3.0 mmol) were dissolved in ethanol (100 mL). The mixture was refluxed for 17 h under nitrogen atmosphere. After concentration to ca. 10 mL, water (100 mL) was added. The mixture was extracted with $CH_2Cl_2$ (50 mL×3), and the combined organic layers were dried over $Na_2SO_4$ and then evaporated. Purification by column chromatography (AcOEt-hexane, 1:4) afforded the title compound 6 (0.48 g, 48%) as pale yellow oil. $^1$H-NMR (CDCl$_3$, 400 MHz): δ7.01 (1H, d, J=3.0 Hz), 6.82 (1H, dd, J=8.8, 3.0 Hz), 6.60 (1H, d, J=8.8 Hz), 3.74 (3H, s), 3.25 (2H, t, J=6.8 Hz), 2.85 (2H, t, J=7.1 Hz), 2.64-2.57 (4H, m), 2.13 (3H, s), 2.07 (3H, s), 1.95-1.92 (2H, m), 1.85-1.82 (2H, m). $^{13}$C-NMR (CDCl$_3$, 100 MHz) δ 151.0, 143.6, 121.2, 118.4, 115.8, 111.3, 56.0, 43.3, 33.4, 32.9, 31.9, 30.4, 28.7, 28.6, 15.7, 15.4. LRMS (ESI): calculated for [(M+H)$^+$] 332.1. found 332.1.

N,S-di-(4-thiapentyl)-2-amino-5-hydroxy-thophenol (7)

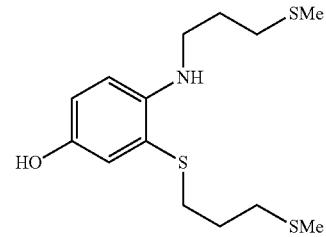 [SMILES: CSCCCNc1ccc(O)cc1SCCCSC]

To a solution of compound 6 (330 mg, 1.0 mmol) in dichloromethane (10 mL, nitrogen-bubbled) was added BBr$_3$ (100 μL, 3.0 mmol) at −78° C. The mixture was warmed to room temperature and stirred for 6 h. The reaction mixture was poured into crushed ice, and the organic layer was separated. The aqueous layer was extracted with dichloromethane (20 mL×2), and the combined organic layers were dried over $Na_2SO_4$. After evaporation, purification by silica gel column chromatography (AcOEt-hexane, 1:4) provided the title compound 7 (200 mg, 63%) as a pale yellow oil. $^1$H-NMR (CDCl$_3$, 400 MHz): δ6.96 (1H, d, J=2.5 Hz), 6.76 (1H, dd, J=8.7, 2.5 Hz), 6.58 (1H, d, J=8.7 Hz), 3.26 (2H, t, J=6.7 Hz), 2.84 (2H, t, J=7.1 Hz), 2.65-2.58 (4H, m), 2.15 (3H, s), 2.09 (3H, s), 1.99-1.94 (2H, m), 1.88-1.83 (2H, m). $^{13}$C-NMR (CDCl$_3$, 100 MHz) δ 146.9, 143.2, 122.2, 118.8, 117.0, 111.8, 56.0, 43.6, 33.3, 32.8, 31.9, 28.6, 28.5, 15.6, 15.4. LRMS (ESI): calculated for [(M+H)$^+$] 318.1. found 318.1.

2-Chloro-1-formyl-3-(hydroxymethylene)cyclohex-1-ene (S1)

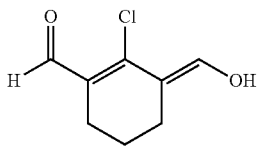

S1 was synthesized as reported procedure. Zhang, Z.; Achilefu, S. Org. Lett., 2004, 6, 2067-2070. A solution of POCl$_3$ (37 mL, 397 mmol) in $CH_2Cl_2$ (35 mL) was slowly added to an ice-cooled solution of DMF (40 mL, 516 mmol) in $CH_2Cl_2$ (40 mL). After the addition was finished, cyclohexanone (10 g, 100 mmol) was added dropwisely. The resulted reaction mixture was refluxed for 2 h. The mixture was then cooled in ice. Water (200 mL) was added slowly while the mixture was stirred. The mixture was stirred for 1 h. The organic layer was collected and the water layer was extracted with additional $CH_2Cl_2$ (40 mL×3). The combined organic layers were dried over $Na_2SO_4$ and then evaporated. The residue was taken up in a mixture of AcOEt-diethylether (3:1), and the mixture was washed with water (30 mL×5) to remove DMF. The combined organic layers were dried over $Na_2SO_4$ and then evaporated. The residue was treated with pentane (200 mL) to give 4.2 g (23%) of S1 as yellow crystalline solid. LRMS (ESI): calculated for [(M+H)$^+$] 173.1. found 173.1.

1-Hydroxycarbonylethyl-2,3,3-trimethylbenzoindoleninium bromide (S2)

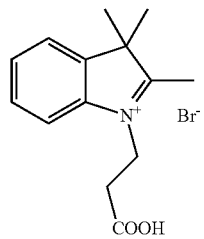 [SMILES: CC1=[N+](CCC(=O)O)c2ccccc2C1(C)C ; [Br-]]

A mixture of 2,3,3-Trimethylbenzoindolenine (19.8 g, 125 mmol) and 3-bromopropionic acid (18.9 g, 125 mmol) in 1,2-dichlorobenzene (200 mL) was stirred at 100° C. for 20 h. After cooling to room temperature, the resulting solid was collected, washed with ether (300 mL) and dried in vacuo for 2 days to give S2 (28 g, 72%) as a pink solid. $^1$H-NMR (DMSO-d$_6$, 400 MHz): δ7.98 (1H, m), 7.82 (1H, m), 7.57 (1H, m), 4.63 (2H, t, J=6.8 Hz), 2.95 (2H, t, J=6.8 Hz), 2.84 (3H, s), 2.15 (3H, s), 2.09 (3H, s), 1.50 (6H, s).

IR780 Dicarboxylic Acid Derivative (8)

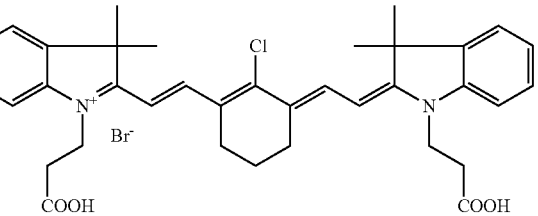

A mixture of S1 (1.6 g, 17.4 mmol), S2 (5.0 g, 32.8 mmol), and sodium acetate (2.6 g, 65.6 mmol) in acetic acid (100 mL) was refluxed for 20 h and the cooled to room temperature. The solvent was evaporated, and the resulting residue was washed with ether (50 mL×2). Purification by silica gel column chromatography (CH$_2$Cl$_2$-MeOH, 9:1 (0.1% acetic acid) to 7:1 (0.1% acetic acid)) provided the title compound 8 (670 mg, 12%) as a glossy red solid. $^1$H-NMR (CDCl$_3$, 400 MHz): δ8.40 (2H, d, J=13.9 Hz), 7.44-7.38 (4H, m), 7.38-7.25 (4H, m), 6.38 (2H, t, J=13.9 Hz), 4.47 (4H, t, J=7.0 Hz), 3.01 (4H, t, J=7.0 Hz), 2.75 (4H, br), 1.96 (2H, br), 1.74 (12H, s). $^{13}$C-NMR (CDCl$_3$, 100 MHz) δ. LRMS (ESI): calculated for [(M-Br$^-$)$^+$] 599.3. found 599.3.

CS790

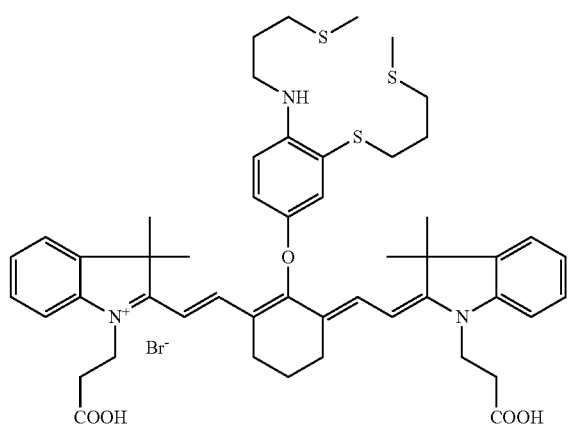 [SMILES: CSCCCNc1ccc(OC2=C(/C=C/C3=[N+](CCC(=O)O)c4ccccc4C3(C)C)CCC/C2=C\C=C2\N(CCC(=O)O)c3ccccc3C2(C)C)cc1SCCCSC ; [Br-]]

To a solution of the phenol 7 (200 mg, 0.63 mmol) in nitrogen-bubbled DMF (10 mL) was added NaH (60% oil dispersion, 64 mg, 2.7 mmol). After stirring at room temperature for 10 min, 8 (360 mg, 0.53 mmol) was added. The mixture was stirred at room temperature for 12 h, and then water (1.0 mL) and 1.0 M HCl (2.6 mL) were successively added. The solvent was removed in vacuo, and then the residue was purified by silica gel column chromatography (CH$_2$Cl$_2$-MeOH, 9:1 to 9:1 (0.1% acetic acid)) to give CS790 (60 mg, 12%) as a bluish green solid. $^1$H-NMR (CDCl$_3$, 400 MHz): δ7.98 (2H, d, J=14.0 Hz), 7.37 (2H, t, J=7.1 Hz), 7.32-7.18 (7H, m), 6.95 (1H, dd, J=9.0, 3.0 Hz), 6.65 (1H, d, J=9.0 Hz), 6.24 (2H, d, J=14.0 Hz), 4.39 (4H, t, J=6.9 Hz), 3.26 (4H, 6.8 Hz), 2.89 (4H, br), 2.86 (2H, t, J=7.1 Hz), 2.76 (4H, br), 2.66-2.59 (4H, m), 2.13 (3H, s), 2.12 (3H, s), 2.06 (2H, br), 1.95-1.91 (2H, m), 1.89-1.87 (2H, m), 1.41 (12H, s). $^{13}$C-NMR (CDCl$_3$, 100 MHz) δ175.0, 171.9, 164.6, 152.1, 146.0, 144.8, 142.2, 141.1, 128.3, 124.6, 122.5, 121.9, 119.5, 119.0, 115.0, 112.3, 110.6, 100.0, 48.8, 42.4, 41.0, 33.9, 32.8, 32.3, 31.1, 28.4, 28.0, 26.9, 23.9, 21.2, 14.1, 14.0. LRMS (ESI): calculated for [(M-Br$^-$)$^+$] 880.4. found 880.4. HRMS (ESI): calculated for C50H62N3O5S3 [(M-Br$^-$)$^+$] 880.3846. found 880.3849.

CS790-AM

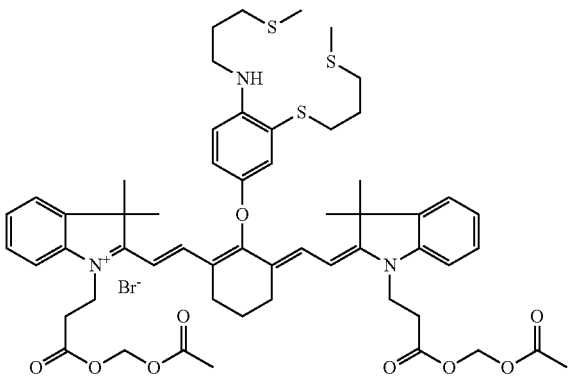 [SMILES: CSCCCNc1ccc(OC2=C(/C=C/C3=[N+](CCC(=O)OCOC(C)=O)c4ccccc4C3(C)C)CCC/C2=C\C=C2\N(CCC(=O)OCOC(C)=O)c3ccccc3C2(C)C)cc1SCCCSC ; [Br-]]

To a solution of CS790 (30 mg, 0.031 mmol) and ethyl diisopropylamine (50 µL, 0.25 mmol) in dry DMF (5 mL) was added bromomethyl acetate (19 mg, 0.12 mmol). The mixture was stirred at room temperature for 4 h, and then acetic acid (15 µL, 0.25 mmol) was added. After dilution with AcOEt (50 mL), the mixture was washed with water (20 mL×5). The organic layer was dried over Na$_2$SO$_4$, and then evaporated. Purification by silica gel column chromatography (CH$_2$Cl$_2$-MeOH, 10:1 to 8:1) provided CS790AM (12 mg, 35%) as a green solid. $^1$H-NMR (CDCl$_3$, 400 MHz): δ7.96 (2H, d, J=14.2 Hz), 7.38 (2H, t, J=7.1 Hz), 7.30-7.18 (7H, m), 6.94 (1H, dd, J=9.0, 3.0 Hz), 6.65 (1H, d, J=9.0 Hz), 6.30 (2H, d, J=14.2 Hz), 5.71 (4H, s), 4.60 (4H, t, J=6.5 Hz), 3.27 (4H, 6.8 Hz), 3.04 (4H, t, J=6.5 Hz), 2.87 (2H, t, J=7.1 Hz), 2.81 (4H, br), 2.66-2.60 (4H, m), 2.13 (3H, s), 2.11 (3H, s), 2.10 (6H, s), 2.06 (2H, br), 1.95-1.91 (2H, m), 1.88-1.85 (2H, m), 1.41 (12H, s). $^{13}$C-NMR (CDCl$_3$, 100 MHz) δ175.5, 172.4, 171.2, 164.4, 152.1, 146.5, 143.4, 141.8, 141.3, 128.0, 125.0, 123.5, 120.5, 119.2, 118.2, 115.0, 111.3, 110.2, 99.7, 79.5, 48.5, 42.0, 41.1, 34.5, 33.0, 32.1, 31.0, 28.0, 27.2, 26.2, 23.1, 21.2, 20.7, 14.1, 14.0. LRMS (ESI): calculated for [(M-Br$^-$)$^+$] 1024.4. found 1024.4. HRMS (ESI): calculated for C50H62N3O5S3 [(M-Br$^-$)$^+$] 1024.4269. found 1024.4256.

Example 2

Synthesis of CS788

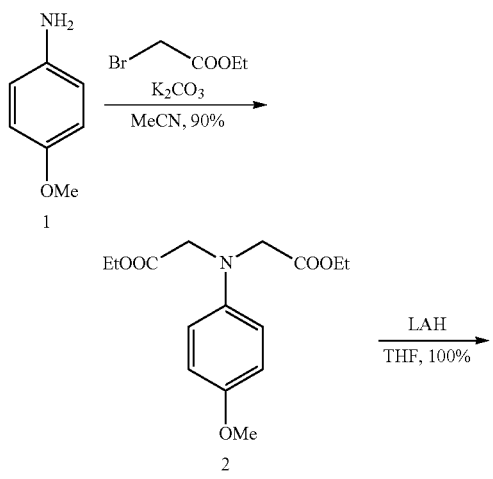

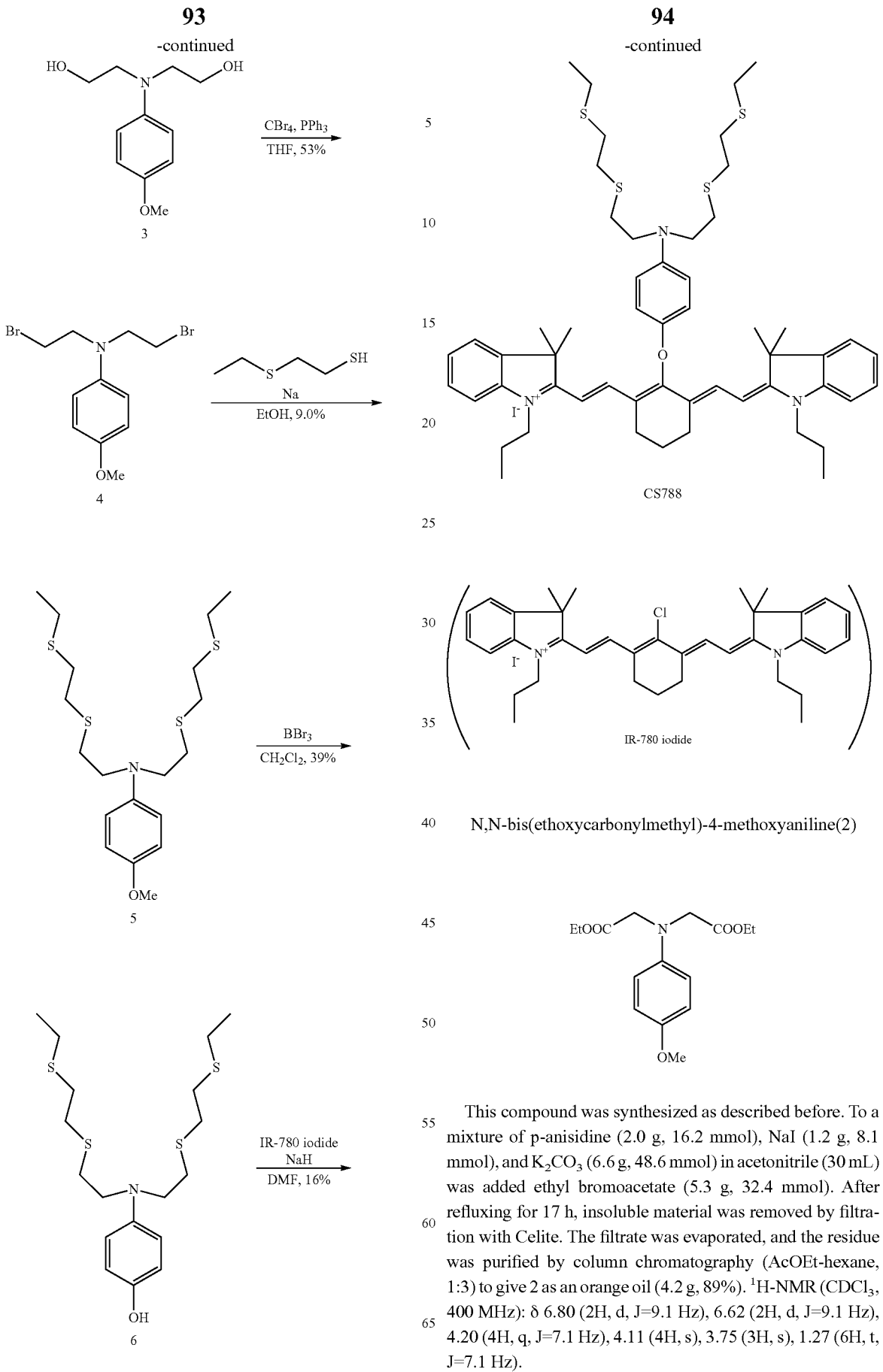

N,N-bis(ethoxycarbonylmethyl)-4-methoxyaniline(2)

This compound was synthesized as described before. To a mixture of p-anisidine (2.0 g, 16.2 mmol), NaI (1.2 g, 8.1 mmol), and $K_2CO_3$ (6.6 g, 48.6 mmol) in acetonitrile (30 mL) was added ethyl bromoacetate (5.3 g, 32.4 mmol). After refluxing for 17 h, insoluble material was removed by filtration with Celite. The filtrate was evaporated, and the residue was purified by column chromatography (AcOEt-hexane, 1:3) to give 2 as an orange oil (4.2 g, 89%). $^1$H-NMR (CDCl$_3$, 400 MHz): δ 6.80 (2H, d, J=9.1 Hz), 6.62 (2H, d, J=9.1 Hz), 4.20 (4H, q, J=7.1 Hz), 4.11 (4H, s), 3.75 (3H, s), 1.27 (6H, t, J=7.1 Hz).

N,N-bis(2-hydroxyethyl)-4-methoxyaniline(3)

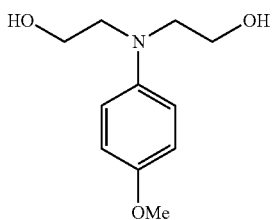 [SMILES: COc1ccc(N(CCO)CCO)cc1]

This compound was synthesized as described before. LiAlH$_4$ (2.5 g, 13.6 mmol) was suspended in THF (30 mL) at 0° C. To the suspension was slowly added a solution of ester 2 (4 g, 13.6 mmol) in THF (5 mL). The mixture was refluxed for 24 h and then cooled to 0° C. Water (2.5 mL), 15% NaOH aqueous solution (2.5 mL), and water (7.5 mL) were successively added to the mixture to quench the excess LiAlH$_4$. The resulting insoluble material was removed by filtration with Celite, and the precipitation was washed by AcOEt (20 mL×10). The combined filtrate were washed with brine, and then dried over Na$_2$SO$_4$. After evaporation, the title compound 3 was obtained (2.8 g, 100%), and this was used to next step without further purification. $^1$H-NMR (CDCl$_3$, 400 MHz): δ 6.83 (2H, d, J=9.1 Hz), 6.72 (2H, d, J=9.1 Hz), 4.20 (2H, q, J=7.1 Hz), 3.76 (3H, s), 3.74 (4H, t, J=4.9 Hz), 3.44 (3H, t, J=4.9 Hz).

N,N-bis(2-bromoethyl)-4-methoxyaniline(4)

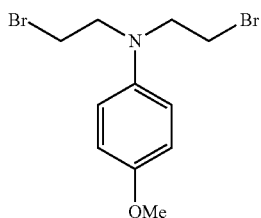 [SMILES: COc1ccc(N(CCBr)CCBr)cc1]

To an ice-cooled solution of triphenyl phosphine (10 g, 40 mmol) in THF (30 mL) was slowly added CBr$_4$ (13.2 g, 40 mmol). The mixture was stirred at room temperature for 10 min. After the color of the mixture turned to yellow, a solution of the compound 3 was slowly added to the mixture. After stirring under nitrogen atmosphere at room temperature for 6 h, the reaction mixture was filtered through Celite and the filtrate was evaporated. The residue was purified by column chromatography (AcOEt-hexane, 1:5) to give the title compound 4 (2.5 g, 54%) as a brown liquid. $^1$H-NMR (CDCl$_3$, 400 MHz): δ 6.83 (2H, d, J=9.1 Hz), 6.72 (2H, d, J=9.1 Hz), 4.20 (2H, q, J=7.1 Hz), 3.76 (3H, s), 3.74 (4H, t, J=4.9 Hz), 3.44 (3H, t, J=4.9 Hz). $^{13}$C-NMR (CDCl$_3$, 100 MHz): δ 152.6, 140.2, 115.2, 114.6, 55.7, 54.1, 28.8.

N,N-bis(3,6-dithiaoctyl)-4-methoxyaniline(5)

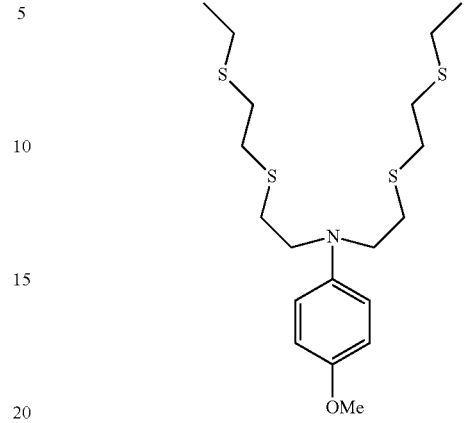

Sodium metal (1.6 g, 68.0 mmol) was dissolved in absolute ethanol (30 mL). To the solution, 3-thiapantane-1-thiol (4.1 g, 33.6 mmol), which was synthesized as described before, was added. After refluxing for 30 min under nitrogen atmosphere, the compound 3 (4.6 g, 13.6 mmol) in absolute ethanol (5 mL) was added. The mixture was refluxed under nitrogen atmosphere for 16 h, and then the solvent was evaporated. Water (20 mL) was added to the residue, and extracted with dichloromethane (30 mL×3). The combined organic layer was dried over Na$_2$SO$_4$, and then evaporated. Purification by column chromatography (AcOEt-hexane, 1:5) afforded the title compound 5 (512 mg, 9.0%) as a yellow oil. $^1$H-NMR (CDCl$_3$, 400 MHz): δ 6.87 (2H, d, J=9.1 Hz), 6.72 (2H, d, J=9.1 Hz), 3.80 (3H, s), 3.50 (4H, t, J=7.3 Hz), 2.80-2.72 (12H, m), 2.59 (4H, q, J=7.4 Hz), 1.30 (6H, t, J=7.4 Hz). $^{13}$C-NMR (CDCl$_3$, 100 MHz): δ 152.1, 141.2, 115.0, 114.1, 55.7, 52.6, 32.4, 31.8, 29.5, 26.0, 14.8.

N,N-bis(3,6-dithiaoctyl)-p-aminophenol (6)

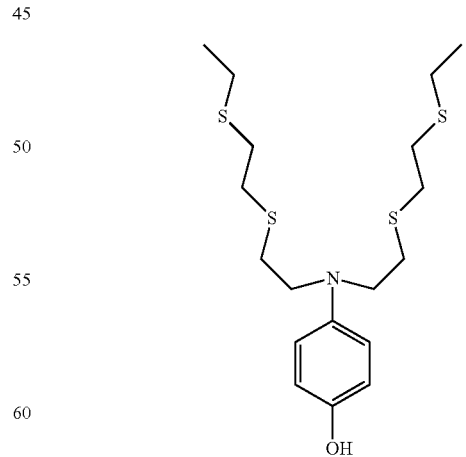

To a solution of compound 5 (100 mg, 0.24 mmol) in dichloromethane (5 mL) was added BBr$_3$ (70 μL) at 0° C. The mixture was warmed to room temperature and stirred for 16 h. The reaction mixture was poured into crushed ice, and the organic layer was separated. The aqueous layer was extracted with dichloromethane (20 mL×2), and the combined organic layer was dried over Na$_2$SO$_4$. After evaporation, purification by column chromatography (AcOEt-hexane, 1:4) provided the title compound 6 (38 mg, 39%) as a pale yellow gum. $^1$H-NMR (CDCl$_3$, 400 MHz): δ 6.76 (2H, d, J=8.8 Hz), 6.62 (2H, d, J=8.8 Hz), 3.45 (4H, t, J=7.3 Hz), 2.77-2.68 (12H, m), 2.56 (4H, q, J=7.4 Hz), 1.26 (6H, t, J=7.4 Hz). $^{13}$C-NMR (CDCl$_3$, 100 MHz): δ 147.9, 141.2, 116.4, 115.3, 52.6, 32.4, 31.8, 29.5, 26.0, 14.8.

CS788

To a mixture of NaH (60% oil dispersion, 4.0 mg, 94 mmol) and compound 6 (38 mg, 94 mmol) in DMF (5 mL) was added IR-780 iodide (52 mg, 78 mmol). After stirring at room temperature for 16 h, the reaction mixture was diluted with a mixture of AcOEt-toluene (3:1, 30 mL), and then washed with water (10 mL×5) and brine (10 mL). The organic layer was dried over Na$_2$SO$_4$ and then evaporated. Purification by column chromatography (MeOH-dichloromethane, 1:20) afforded CS-788 as a green film (13 mg, 16%). $^1$H-NMR (CDCl$_3$, 400 MHz): δ 7.93 (2H, d, J=14.2 Hz), 7.33 (2H, t, J=7.4 Hz), 7.27 (2H, d, J=6.2 Hz), 7.18 (2H, t, J=7.4 Hz), 7.09 (2H, d, J=8.0 Hz), 6.97 (2H, d, J=9.1 Hz), 6.68 (2H, d, J=9.1 Hz), 6.07 (2H, d, J=14.2 Hz), 4.07 (4H, t, J=7.2 Hz), 3.47 (4H, t, J=7.0 Hz), 2.75-2.65 (16H, m), 2.55 (4H, q, J=7.4 Hz), 2.04 (2H, m), 1.85 (4H, m), 1.38 (12H, s), 1.22 (6H, t, J=7.4 Hz), 1.05 (6H, t, J=7.5 Hz). $^{13}$C-NMR (CDCl$_3$, 100 MHz): δ 171.7, 165.0, 152.7, 142.3, 142.2, 142.1, 140.9, 128.6, 124.9, 122.8, 122.1, 115.6, 14.7, 110.6, 100.0, 52.3, 48.9, 46.1, 32.5, 31.8, 29.6, 27.9, 26.1, 24.6, 20.8, 14.8, 11.7. LRMS (ESI): calculated for [(M-I)$^+$] 908.5. found 908.5. HRMS (ESI): calculated for C54H74O1N3S4 [(M-I)$^+$] 908.4709. found 908.4740.

Example 3

Synthesis of Tokyo Green-Based Fluorescent Sensors

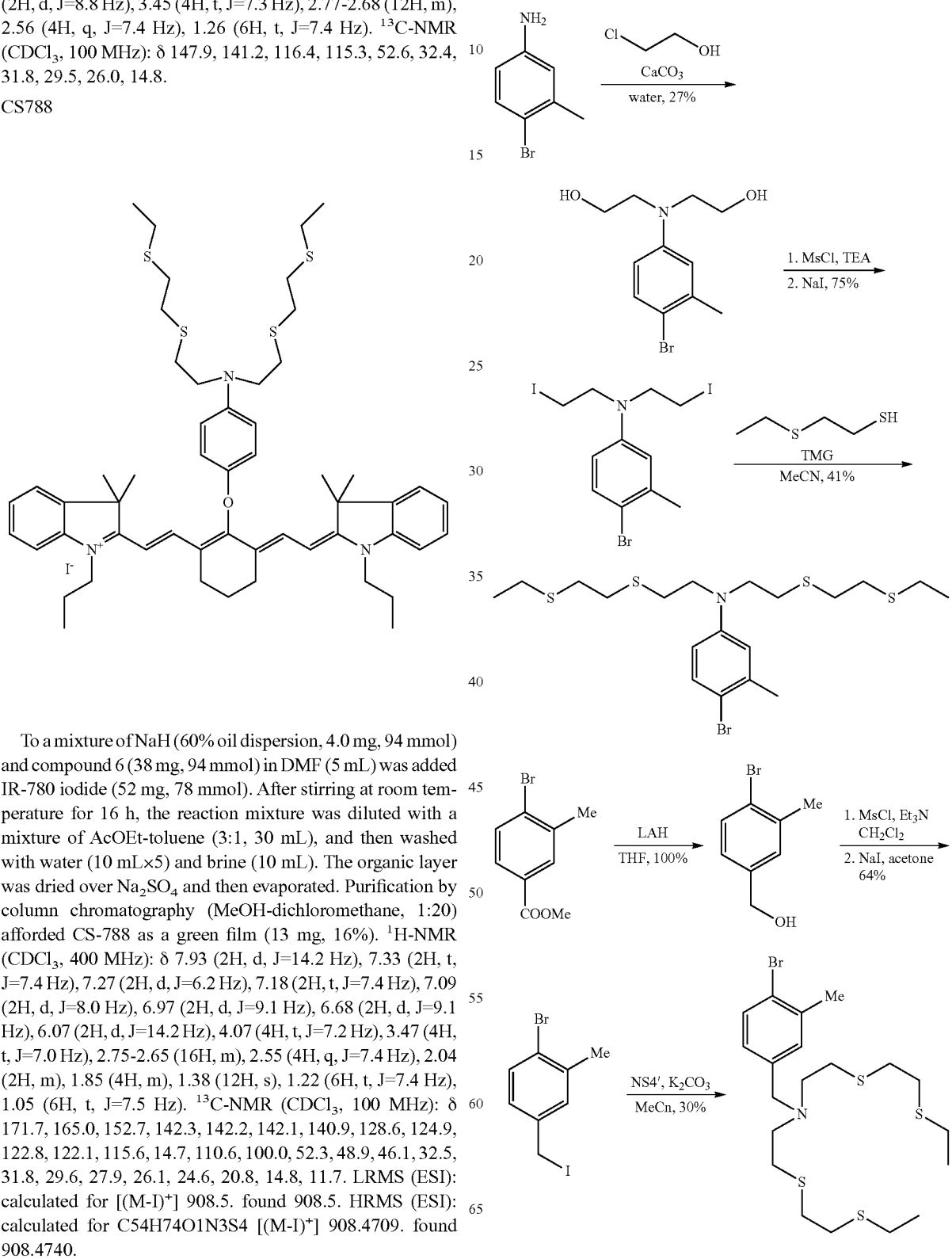

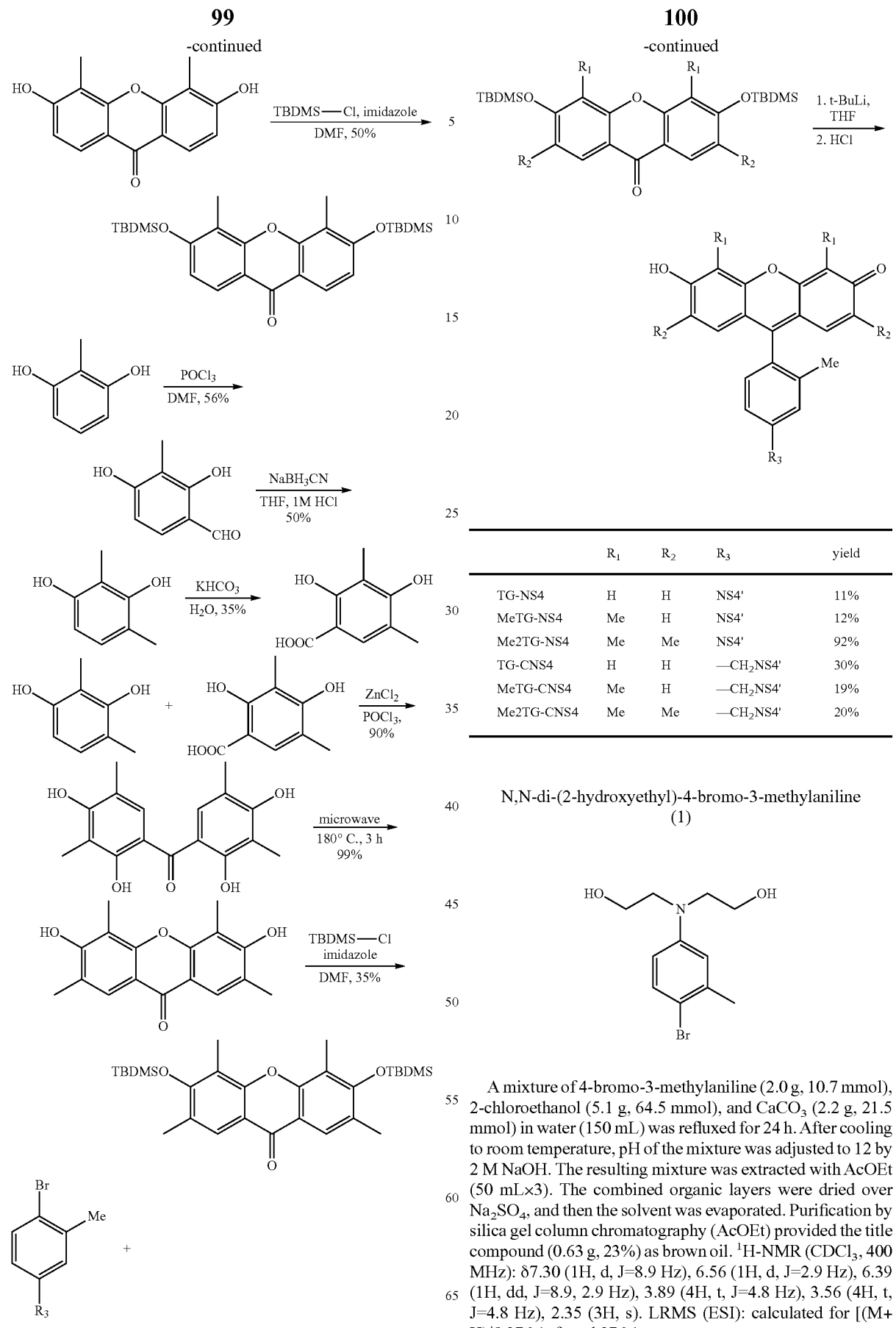

| | $R_1$ | $R_2$ | $R_3$ | yield |
|---|---|---|---|---|
| TG-NS4 | H | H | NS4' | 11% |
| MeTG-NS4 | Me | H | NS4' | 12% |
| Me2TG-NS4 | Me | Me | NS4' | 92% |
| TG-CNS4 | H | H | —CH$_2$NS4' | 30% |
| MeTG-CNS4 | Me | H | —CH$_2$NS4' | 19% |
| Me2TG-CNS4 | Me | Me | —CH$_2$NS4' | 20% |

N,N-di-(2-hydroxyethyl)-4-bromo-3-methylaniline (1)

A mixture of 4-bromo-3-methylaniline (2.0 g, 10.7 mmol), 2-chloroethanol (5.1 g, 64.5 mmol), and CaCO$_3$ (2.2 g, 21.5 mmol) in water (150 mL) was refluxed for 24 h. After cooling to room temperature, pH of the mixture was adjusted to 12 by 2 M NaOH. The resulting mixture was extracted with AcOEt (50 mL×3). The combined organic layers were dried over Na$_2$SO$_4$, and then the solvent was evaporated. Purification by silica gel column chromatography (AcOEt) provided the title compound (0.63 g, 23%) as brown oil. $^1$H-NMR (CDCl$_3$, 400 MHz): δ7.30 (1H, d, J=8.9 Hz), 6.56 (1H, d, J=2.9 Hz), 6.39 (1H, dd, J=8.9, 2.9 Hz), 3.89 (4H, t, J=4.8 Hz), 3.56 (4H, t, J=4.8 Hz), 2.35 (3H, s). LRMS (ESI): calculated for [(M+H)$^+$] 276.1. found 276.1.

N,N-di-(2-iodoethyl)-4-bromo-3-methylaniline (2)

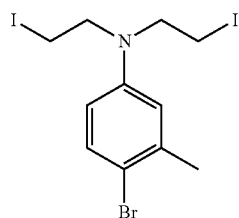

To an ice-cooled solution of compound 1 (1.8 g, 6.6 mmol) and triethylamine (2.6 g, 26.4 mmol) in CH$_2$Cl$_2$ (30 mL) was added methanesulfonyl chloride (2.3 g, 20.0 mmol) dropwisely. The mixture was stirred at room temperature for 1 h, and then saturated NH$_4$Claq (20 mL) was added to the mixture. The organic layer was separated and then washed with water (20 mL×2) and brine (20 mL) successively. After evaporation of the organic layer, the residue was taken up in acetone (30 mL). Sodium iodide (3.0 g, 20.0 mmol) was added to the mixture, and the resultant mixture was refluxed for 6 h. The reaction mixture was diluted with water (50 mL) and then extracted with CH$_2$Cl$_2$ (50 mL×2). The combined organic layers were dried over Na$_2$SO$_4$, and then the solvent was evaporated. Recrystallization from a mixture of AcOEt and hexane provided the title compound (2.5 g, 76%) as off-white solid. $^1$H-NMR (CDCl$_3$, 400 MHz): δ7.35 (1H, d, J=8.8 Hz), 6.51 (1H, d, J=2.9 Hz), 6.37 (1H, dd, J=8.8, 2.9 Hz), 3.71 (4H, t, J=8.2 Hz), 3.20 (4H, t, J=8.2 Hz), 2.37 (3H, s). $^{13}$C-NMR (CDCl$_3$, 100 MHz) δ 144.7, 138.9, 133.2, 144.2, 122.6, 111.2, 54.0, 23.5, 1.41.

N,N-di-(3,6-dithiaoctyl)-4-bromo-3-methylaniline (3)

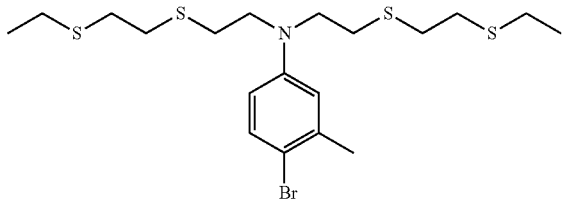 [SMILES: CCSCCSCCN(CCSCCSCC)c1ccc(Br)c(C)c1]

To a solution of 3-thiapantane-1-thiol (490 mg, 4.0 mmol) an tetramethylguanidine (920 mg, 8.0 mmol) in acetonitrile (20 mL) was added compound 2 (1.0 g, 2.0 mmol). Zeng, L.; Miller, E. W.; Pralle, A.; Isacoff, E. Y.; Chang, C. J. *J. Am. Chem. Soc.* 2006, 128, 10-11. The mixture was refluxed for 5 h, and then cooled to room temperature. The solvent was evaporated, and the residue was taken up in AcOEt (100 mL). The mixture was washed with water (50 mL×2) and then dried over Na$_2$SO$_4$. After evaporation, the residue was purified by silica gel column chromatography (AcOEt-hexane, 1:9) to give the title compound 3 (400 mg, 41%). $^1$H-NMR (CDCl$_3$, 400 MHz): δ7.35 (1H, d, J=8.8 Hz), 6.56 (1H, d, J=3.0 Hz), 6.40 (1H, dd, J=8.8, 3.0 Hz), 3.56 (4H, t, J=7.4 Hz), 2.87-2.74 (12H, m), 2.59 (4H, q, J=7.4 Hz), 2.38 (3H, s), 1.30 (6H, t, J=7.4 Hz). $^{13}$C-NMR (CDCl$_3$, 100 MHz) δ145.9, 138.6, 133.0, 114.4, 111.6, 111.4, 51.7, 32.5, 31.9, 29.4, 26.2, 23.5, 14.8. LRMS (ESI): calcd for [(M+H)$^+$] 481.1. found 481.1

4-Bromo-3-methylbenzylalcohol (4)

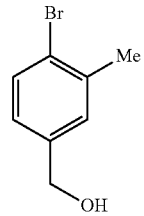

A solution of methyl 4-bromo-3-methylbenzoate (2.0 g, 8.7 mmol) in dry THF (10 mL) was added to an ice-cooled suspension of lithium aluminiumhydride (400 mg, 10.4 mmol) in dry THF (30 mL). After addition, the mixture was warmed to room temperature and then stirred for 3 h. The excess lithium aluminiumhydride was quenched by successive addition of water (0.4 mL), 15% NaOHaq (0.4 mL), and water (1.2 mL) under ice cooling. The insoluble material appeared was removed by filtration (celite), and the precipitate was washed by AcOEt (20 mL×5). The combined filtrates were washed with brine (50 mL) and then dried over Na$_2$SO$_4$. The solvent was evaporated, and the obtained product (1.6 g, 100%) was used for next step without further purification. $^1$H-NMR (CDCl$_3$, 400 MHz): δ7.53 (1H, d, J=8.1 Hz), 7.26 (1H, d, J=1.5 Hz), 6.40 (1H, dd, J=8.1, 1.5 Hz), 4.68 (2H, s), 2.44 (3H, s).

4-Bromo-3-methyliodomethylbenzene (5)

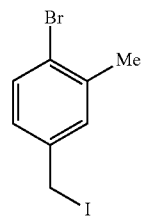

To an ice-cooled solution of compound 5 (1.6 g, 8.0 mmol) and triethylamine (1.6 g, 16.0 mmol) in CH$_2$Cl$_2$ (30 mL) was added methanesulfonyl chloride (1.4 g, 12.0 mmol) dropwisely. The mixture was stirred at room temperature for 3 h, and then saturated NH$_4$Claq (20 mL) was added to the mixture. The organic layer was separated and then washed with water (20 mL×2) and brine (20 mL) successively. After evaporation of the organic layer, the residue was taken up in acetone (30 mL). Sodium iodide (1.8 g, 12.0 mmol) was added to the mixture, and the resultant mixture was refluxed for 13 h. The reaction mixture was diluted with water (50 mL) and then extracted with CH$_2$Cl$_2$ (50 mL×2). The combined organic layers were dried over Na$_2$SO$_4$, and then the solvent was evaporated. Purification by silica gel column chromatography (AcOEt-hexane, 1:7) provided the title compound (1.6 g, 64%) as pale yellow oil. $^1$H-NMR (CDCl$_3$, 400 MHz): δ7.45 (1H, d, J=8.2 Hz), 7.26 (1H, d, J=1.7 Hz), 7.07 (1H, dd, J=8.2, 1.7 Hz), 4.39 (2H, s), 2.39 (3H, s). $^{13}$C-NMR (CDCl$_3$, 100 MHz) δ 138.5, 138.4, 132.7, 131.1, 127.7, 124.3, 23.0, 4.8.

N-(4-bromo-3-methylbenzyl)-3,6,12,15-tetrathia-9-monoazaheptadecane (6)

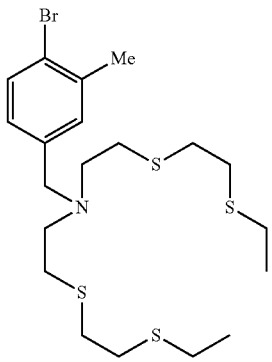 [SMILES: CCSCCSCCN(CCSCCSCC)Cc1ccc(Br)c(C)c1]

A mixture of compound 5 (300 mg, 0.97 mmol), potassium bicarbonate (160 mg, 1.2 mmol), and 3,6,12,15-tetrathia-9-monoazaheptadecane$^i$ (300 mg, 0.97 mmol) in acetonitrile (15 mL) was refluxed for 24 h. The solvent was evaporated, and then the residue was taken up in CH$_2$Cl$_2$ (50 mL). The mixture was washed with water (50 mL), and the organic layer was dried over Na$_2$SO$_4$ and then evaporated. Purification by silica gel column chromatography (AcOEt-hexane, 1:7) provided the title compound (120 mg, 25%) as pale brown liquid. $^1$H-NMR (CDCl$_3$, 400 MHz): δ7.45 (1H, d, J=8.1 Hz), 7.26 (1H, d, J=1.5 Hz), 7.07 (1H, dd, J=8.1, 1.5 Hz), 3.55 (2H, s), 2.75-2.62 (16H, m), 2.37 (4H, q, J=7.4 Hz), 2.38 (3H, s), 1.25 (3H, t, J=7.4 Hz). $^{13}$C-NMR (CDCl$_3$, 100 MHz) δ 138.4, 137.6, 132.1, 131.1, 127.6, 123.3, 57.9, 53.8, 32.3, 31.7, 30.0, 26.0, 22.9, 14.8. LRMS (ESI): calcd for [(M+H)$^+$] 498.1. found 498.1

3,6-Di-(t-butyldimethylsilyloxy)xanthone and 3,6-dihydroxy-4,5-dimethylxanthone were prepared by reported procedure. Grover, P. K.; Shah, G. D.; Shah, R. C. *J. Indian Chem. Soc.* 1955, 3982-3985; Da Re, P.; Sagramora, L.; Mancini, V.; Valanti, P.; Cima, L. *J. Med. Chem.* 1970, 13, 527-531.

3,6-Di-(tert-butyldimethylsilyloxy)-4,5-dimethylxanthone (7)

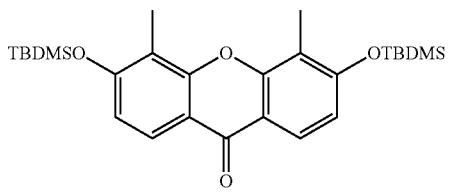 [SMILES: Cc1c(O[Si](C)(C)C(C)(C)C)ccc2c(=O)c3ccc(O[Si](C)(C)C(C)(C)C)c(C)c3oc12]

To a solution of 3,6-dihydroxy-4,5-dimethylxanthone (210 mg, 0.82 mmol) and imidazole (557 mg, 8.2 mmol) in dry DMF (10 mL) was added tert-butyldimethylsilyl chloride (735 mg, 4.9 mmol). The mixture was stirred at room temperature for 3 h and then diluted with toluene (70 mL). After washing with water (20 mL×5), the organic layer was dried over Na$_2$SO$_4$ and then evaporated. Purification by silica gel column chromatography (AcOEt-hexane, 1:7) provided the title compound (210 mg, 53%) as white powder. $^1$H-NMR (CDCl$_3$, 400 MHz): δ8.11 (2H, d, J=8.7 Hz), 6.87 (2H, d, J=8.7 Hz), 2.45 (6H, s), 1.10 (18H, s), 0.33 (12H, s).

2,4-Dihydroxy-3-methylbenzaldehyde (8)

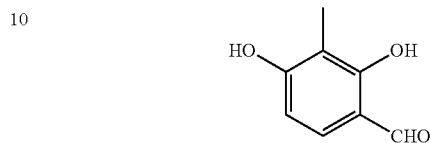

To an ice-cooled solution of POCl$_3$ (4.9 g, 32.2 mmol) in dry DMF (10.0 mL, 64.4 mmol) was slowly added a solution of 2-methylresorcinol (2.0 g, 16.1 mmol) in dry DMF (5.0 mL). After stirring at room temperature for 12 h, the mixture was cooled to 0° C. and then carefully treated with iced water (15 mL). 2 M sodium hydroxide was added to adjust pH to 10. The resulting mixture was heated to reflux for 10 min. Then, the mixture was acidified by 3 M HCl (pH=3). The resulting solid was collected by filtration, and the precipitate was washed with water (10 mL×3). The obtained orange solid (4.0 g, 46%) was dried in vacuo and used for the next reaction without further purification. $^1$H-NMR (DMSO-d$_6$, 400 MHz): δ9.71 (1H, s), 7.43 (1H, d, J=8.5 Hz), 6.55 (1H, d, J=8.5 Hz), 1.97 (3H, s).

2,4-Dimethylresorcinol (9)

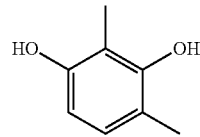

To a solution of compound 8 (0.90 g, 5.9 mmol) and NaBH$_3$CN (1.1 g, 17.7 mmol) in THF (36 mL) was slowly added 1 M HCl (17.7 mL) to keep pH of the mixture at 3. The mixture was stirred at room temperature for 3 h. Water (50 mL) was added, and then the mixture was extracted with diethyl ether (50 mL×3). The combined organic layers were dried over Na2SO4 and then evaporated. The obtained white powder (0.58 g, 70%) was used to next step without further purification. $^1$H-NMR (CDCl$_3$, 400 MHz): δ6.85 (1H, d, J=8.1 Hz), 6.37 (1H, d, J=8.1 Hz), 2.22 (3H, s), 2.19 (3H, s). $^{13}$C-NMR (CDCl$_3$, 100 MHz) δ152.8, 127.6, 115.1, 109.9, 107.0, 15.5, 8.2.

2,4-Dihydroxy-3,5-dimethylbenzoic acid (10)

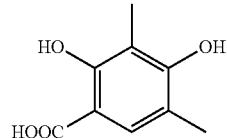

A mixture of compound 9 (0.5 g, 3.6 mmol) and KHCO$_3$ (1.8 g, 18.1 mol) in water (6 mL) was stirred at 80° C. for 8 h.

The insoluble material was removed by filtration (celite), and the filtrate was acidified by conc. HCl (pH=3). The resulting solid was collected by filtration, and the precipitate was dried in vacuo to afford the title compound as brown fine powder (160 mg, 24%). This material was used to next step without further purification. $^1$H-NMR (CD$_3$OD, 400 MHz): δ7.41 (1H, s), 2.11 (3H, s), 2.05 (3H, s). $^{13}$C-NMR (CD$_3$OD, 100 MHz) δ172.9, 159.7, 128.8, 115.7, 110.5, 107.5, 15.1, 7.1.

3,3'-Dihydroxy,2,4,5,7-tetramethylxanthon (11)

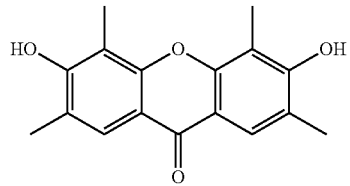

Zinc chloride (442 mg, 3.2 mmol) was fused in Schlenk flask before the reaction. Compound 9 (146 mg, 1.2 mmol) and 10 (160 mg, 0.88 mmol) were added to the flask, and POCl$_3$ (1.3 g, 8.8 mmol) was added under nitrogen flow. The mixture was stirred at 80° C. for 1 h and then cooled to room temperature. The mixture was poured into crushed ice, and the resulting solid was collected by filtration. The solid was dried in vacuo, and benzophenone derivative, a precursor of the title compound was obtained as brown solid (220 mg, 88%). This material was suspended in a solution of KHCO$_3$ (200 mg, 2.0 mmol) in water (2.2 mL). The mixture was heated at 180° C. for 3 h by microwave reactor (CEM Intelligent Explorer Discover (Matthews, N.C.)). After the reaction, the mixture was acidified by 1 M HCl (pH=1-2), and the resulting precipitate was collected by filtration and then washed with water (3 mL×3). The precipitate was dried in vacuo to afford the title compound (210 mg, 90%) as brown solid. $^1$H-NMR (CD$_3$OD, 400 MHz): δ7.56 (2H, s), 2.22 (6H, s), 2.18 (6H, s). $^{13}$C-NMR (CD$_3$OD, 100 MHz) δ176.9, 159.0, 154.2, 123.6, 121.7, 113.2, 110.4, 15.4, 7.3.

3,6-Di-(tert-butyldimethylsilyloxy)-2,4,5,7-tetramethylxanthon (12)

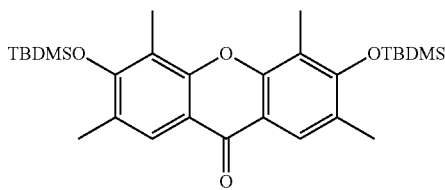 [SMILES: Cc1cc2c(=O)c3cc(C)c(O[Si](C)(C)C(C)(C)C)c(C)c3oc2c(C)c1O[Si](C)(C)C(C)(C)C]

To a solution of 3,6-dihydroxy-2,4,5,7-tetramethylxanthon (54 mg, 0.19 mmol) and imidazole (136 mg, 1.9 mmol) in dry DMF (4 mL) was added tert-butyldimethylsilyl chloride (165 mg, 1.1 mmol). The mixture was stirred at room temperature for 13 h and then diluted with toluene (50 mL). After washing with water (20 mL×5), the organic layer was dried over Na$_2$SO$_4$ and then evaporated. Purification by silica gel column chromatography (AcOEt-hexane, 1:7) provided orange solid. The resulting solid was washed with hexane (5 mL×3) to give the title compound (35 mg, 35%) as white powder. $^1$H-NMR (CDCl$_3$, 400 MHz): δ7.96 (2H, s), 2.40 (6H, s), 2.32 (6H, s), 1.08 (18H, s), 0.25 (12H, s). $^{13}$CNMR (CDCl$_3$, 100 MHz): δ176.8, 157.3, 154.4, 125.7, 125.0, 116.4, 115.9, 26.0, 18.8, 17.7, 10.6, −3.0.

General Procedure for TG-NS4 Derivatives.

Bromobenzene derivatives and xanthone derivatives were dried in vacuo for 1 h before use. To a dry schlenk flask, bromobenzene 3 or 6 (0.40 mmol) and dry THF (1 mL) was added. The mixture was cooled to −78° C. under a nitrogen atmosphere, and then t-BuLi (1.7 M pentane solution, 0.80 mmol) was slowly added by syringe. After stirring for 5 min at −78° C., a solution of xanthone derivative (0.20 mmol) in dry THF (1 mL) was added dropwisely. The mixture was slowly warmed to room temperature and then stirred for 10 min. To the mixture, 1 M HCl (3 mL) was added. After stirring for 30 min at room temperature, the mixture was alkalized by addition of 2 M NaOH (3 mL) and acidified with acetic acid (1 mL) successively. The mixture was diluted with water (10 mL), and the mixture was extracted with CH$_2$Cl$_2$ (10 mL×3). The combined organic layers were dried over Na$_2$SO$_4$ and then evaporated. Purification by silica gel column chromatography (chloroform-methanol, 30:1) provided the TG-NS4 derivatives.

TG-NS4

Red solid (8.7 mg, 11%). $^1$H-NMR (CDCl$_3$, 400 MHz): δ7.24 (2H, d, J=9.1 Hz), 7.05 (1H, d, J=8.8 Hz), 6.91 (2H, s), 6.88 (2H, d, J=9.1 Hz), 6.66 (2H, brs), 3.68 (4H, brs), 2.82-2.88 (12H, m), 2.62 (4H, q, J=7.4 Hz), 2.05 (3H, s), 1.30 (6H, t, J=7.4 Hz). $^{13}$CNMR (CDCl$_3$, 100 MHz): δ176.9, 158.1, 155.5, 141.9, 138.1, 132.2, 132.1, 130.0, 129.0, 127.2, 125.2, 114.9, 103.8, 53.9, 32.5, 31.8, 30.1, 26.1, 19.8, 14.9. LRMS (ESI): calculated for [(M+H)$^+$] 614.2. found 614.2. HRMS (ESI): calcd for C$_{32}$H$_{40}$O$_3$NS$_4$ [(M+H)$^+$] 614.1886. found 614.1869.

MeTG-NS4

Red solid (9.1 mg, 12%). $^1$H-NMR (CDCl$_3$, 400 MHz): δ7.10 (2H, d, J=9.2 Hz), 7.01 (1H, d, J=9.1 Hz), 6.97 (2H, d, J=9.2 Hz), 6.64 (2H, m), 3.66 (4H, t, J=7.6 Hz), 2.82-2.89 (12H, m), 2.62 (4H, q, J=7.4 Hz), 2.46 (6H, s), 2.02 (3H, s), 1.30 (6H, t, J=7.4 Hz). $^{13}$CNMR (CDCl$_3$, 100 MHz): δ171.2, 154.2, 149.7, 147.2, 138.7, 136.2, 130.9, 126.6, 121.7, 116.1, 113.1, 115.6, 108.1, 52.6, 32.3, 32.3, 29.7, 25.2, 21.0, 15.0, 8.6. LRMS (ESI): calcd for [(M+H)$^+$] 642.2. found 642.3. HRMS (ESI): calcd for C$_{34}$H$_{44}$O$_3$NS$_4$ [(M+H)$^+$] 642.2199. found 642.2182.

Me2TG-NS4

Red solid (92 mg, 92%). $^1$H-NMR (CDCl$_3$, 400 MHz): δ7.01 (2H, d, J=9.1 Hz), 6.88 (2H, s), 6.67 (1H, s), 6.65 (1H, d, J=9.1 Hz), 3.69 (4H, t, J=7.2 Hz), 2.82-2.89 (12H, m), 2.62 (4H, q, J=7.3 Hz), 2.45 (6H, s), 2.24 (6H, s), 2.04 (3H, s), 1.30 (6H, t, J=7.3 Hz). $^{13}$CNMR (CDCl$_3$, 100 MHz): δ171.2, 153.2, 149.5, 147.2, 137.7, 130.9, 129.2, 126.6, 121.7, 116.1, 113.1, 111.6, 109.1, 51.6, 32.6, 32.0, 29.7, 26.2, 20.6, 17.0, 14.9, 8.5. LRMS (ESI): calculated for [(M+H)$^+$] 670.2. found 670.3. HRMS (ESI): calcd for C$_{36}$H$_{43}$O$_3$NS$_4$ [(M+H)$^+$] 670.2512. found 670.2516.

TG-CNS4

Red solid (40 mg, 32%). $^1$H-NMR (CDCl$_3$, 400 MHz): δ7.42 (1H, s), 7.39 (1H, d, J=8.1 Hz), 7.15 (1H, d, J=8.1 Hz), 7.11 (2H, d, J=9.2 Hz), 6.94 (2H, s), 6.88 (2H, d, J=9.2 Hz), 3.77 (2H, s), 2.86-2.77 (16H, m), 2.58 (4H, q, J=7.4 Hz), 2.08 (3H, s), 1.27 (6H, t, J=7.4 Hz). $^{13}$CNMR (CDCl$_3$, 100 MHz): δ175.9, 158.1, 155.3, 141.1, 136.1, 131.2, 131.1, 130.7, 129.1, 126.2, 122.2, 114.9, 103.8, 58.2, 53.9, 32.5, 31.8, 30.1, 26.1, 19.8, 14.9. LRMS (ESI): calculated for [(M+H)$^+$] 628.1. found 628.0. HRMS (ESI): calcd for C$_{33}$H$_{42}$O$_3$NS$_4$ [(M+H)$^+$] 628.2042. found 628.2029.

MeTG-CNS4

Red solid (25 mg, 19%). $^1$H-NMR (CDCl$_3$, 400 MHz): δ7.40 (1H, s), 7.37 (1H, d, J=8.2 Hz), 7.11 (1H, d, J=8.2 Hz), 6.95 (2H, d, J=9.3 Hz), 6.92 (2H, d, J=9.3 Hz), 3.76 (2H, s), 2.82-2.74 (16H, m), 2.59 (4H, q, J=7.4 Hz), 2.46 (6H, s), 2.05 (3H, s), 1.28 (6H, t, J=7.4 Hz). $^{13}$CNMR (CDCl$_3$, 100 MHz): δ176.0, 173.4, 154.8, 141.0, 136.3, 132.0, 130.6, 129.3, 128.5, 126.1, 120.8, 115.0, 112.6, 53.9, 32.5, 31.8, 30.0, 26.1, 20.8, 19.7, 14.9, 8.2. LRMS (ESI): calculated for [(M+H)$^+$] 656.3. found 656.3. HRMS (ESI): calcd for C$_{35}$H$_{46}$O$_3$NS$_4$ [(M+H)$^+$] 656.2355. found 656.2359.

Me2TG-CNS4

Red solid (21 mg, 20%). $^1$H-NMR (CDCl$_3$, 400 MHz): δ7.40 (1H, s), 7.39 (1H, d, J=8.0 Hz), 7.11 (1H, d, J=8.0 Hz), 6.72 (2H, s), 3.80 (2H, s), 2.91-2.70 (16H, m), 2.60 (4H, q, J=7.3 Hz), 2.44 (6H, s), 2.19 (6H, s), 2.08 (3H, s), 1.29 (6H, t, J=7.3 Hz). $^{13}$CNMR (CDCl$_3$, 100 MHz): δ175.2, 158.9, 152.7, 149.5, 135.11, 131.5, 130.9, 129.5, 129.1, 126.13, 122.8, 115.9, 111.6, 58.3, 54.1, 32.5, 31.8, 30.1, 26.1, 16.8, 14.8, 8.4. LRMS (ESI): calculated for [(M+H)$^+$] 656.3. found 656.3. HRMS (ESI): calcd for C$_{35}$H$_{46}$O$_3$NS$_4$ [(M+H)$^+$] 656.2355. found 656.2359.

Example 4

Synthesis of CS7

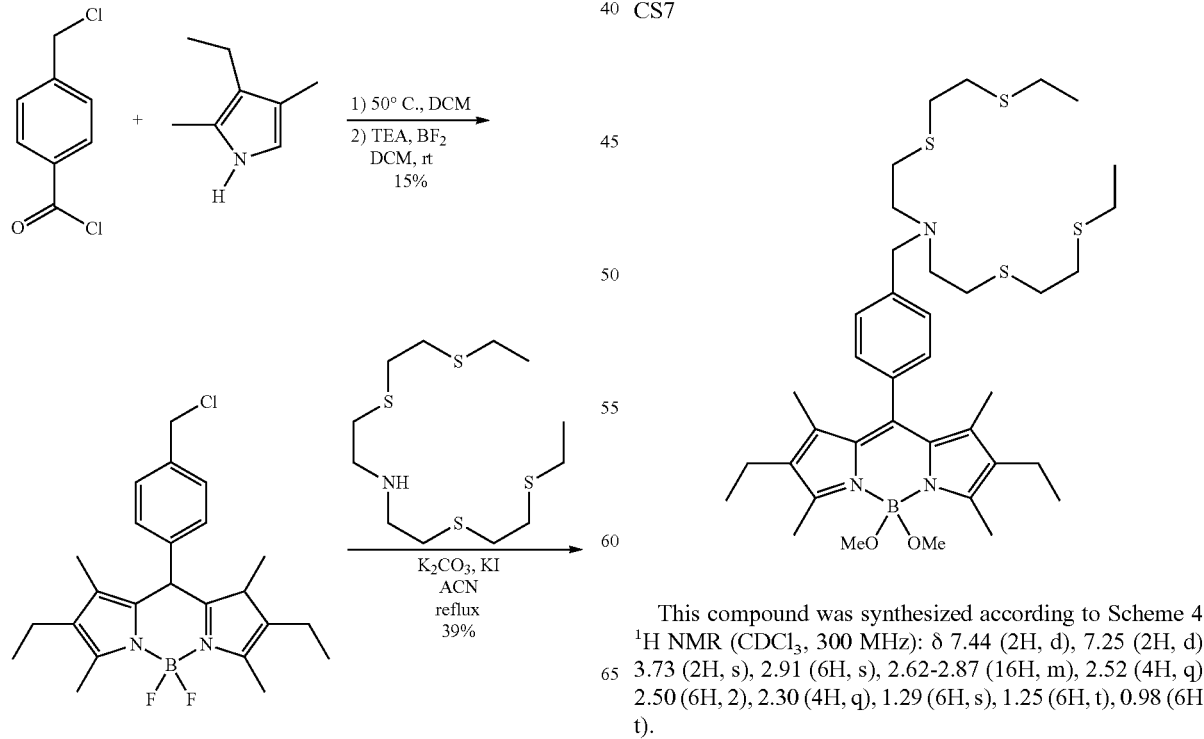

CS7

This compound was synthesized according to Scheme 4. $^1$H NMR (CDCl$_3$, 300 MHz): δ 7.44 (2H, d), 7.25 (2H, d), 3.73 (2H, s), 2.91 (6H, s), 2.62-2.87 (16H, m), 2.52 (4H, q), 2.50 (6H, 2), 2.30 (4H, q), 1.29 (6H, s), 1.25 (6H, t), 0.98 (6H, t).

Example 5

In Vitro and In Vivo Studies

General Spectroscopic, Flow Cytometry, Confocal Microscopy, and Animal Imaging Procedures Spectroscopic Materials and Methods.

Millipore water was used to prepare all aqueous solutions. All spectroscopic measurements were performed in 20 mM HEPES buffer, pH 7.0. Absorption spectra were recorded on a Varian Cary 50 spectrophotometer (Walnut Creek, Calif.) and fluorescence spectra were recorded on a Photo Technology International Quanta Master 4 L-format scan spectrofluorometer (Lawrenceville, N.J.) equipped with an LPS-220B 75-W xenon lamp and power supply, A-1010B lamp housing with integrated igniter, switchable 814 photocounting/analog photomultiplier detection unit, and MD5020 motor driver. Samples for absorption and emission measurements were contained in 1-cm×1-cm quartz cuvettes (1.4-mL volume, Starna, Atascadero, Calif.). Metals used in the selectivity assay were derived from their chloride salts or nitrate salts. The binding affinity of $Cu^+$ to the dyes was measured using thiourea as a competitive ligand to provide a buffered $Cu^+$ solution. Briefly, a 1-2 µM solution of dye was made in 20 mM HEPES, pH 7.0 and buffered with a known concentration of thiourea from a 500 mM stock in MilliQ $H_2O$. Cu(I) was delivered in the form of $[Cu(MeCN)_4][PF_6]$ from an acetonitrile stock solution (2 or 10 mM). The maximum acetonitrile concentration was 0.1%; this concentration of acetonitrile is not high enough to effectively compete with the dyes for $Cu^+$. Stability constants for thiourea binding were taken from the literature: $\beta_{12}=2.0\times10^{12}$, $\beta_{13}=2.0\times10^{14}$, $\beta_{14}=3.4\times10^{15}$. Martell, A. E.; Smith, R. M. *Critical Stability Constants*; Plenum Press: New York, 1989. The apparent dissociation constant ($K_d$) was determined using the following equation: $(F-F_{min})/(F_{max}-F_{min})=[Cu^+]/(K_d+[Cu^+])$, where F is the observed fluorescence; $F_{max}$ is the fluorescence for the $Cu^+$:dye complex; $F_{min}$ is the fluorescence for the dye; and $[Cu^+]$ is the 'free' $Cu^+$ available for complexation, which was calculated using the stability constants for thiourea and standard competition equilibrium expressions.

Preparation and Staining of Cell Cultures.

Cells were grown in the Tissue Culture Facility at the University of California, Berkeley with expert technical assistance from Ann Fischer and Michelle Yasukawa. HEK (Human Embryonic Kidney) 293T cells were cultured in Dulbecco's Modified Eagle Medium (DMEM, Invitrogen, Carlsbad, Calif.) supplemented with 10% Fetal Bovine Serum (FBS, Invitrogen, Carlsbad, Calif.) and glutamine (2 mM). Two days before imaging, cells were passed and plated on 12-mm glass coverslips coated with poly-L-lysine (50 mg/mL, Sigma, St. Louis, Mo.). For all experiments, solutions of dyes (from 5 mM stocks in DMSO) were made in Dulbecco's Phosphate buffered saline (DPBS, GIBCO) without calcium chloride, magnesium chloride, magnesium sulfate, sodium bicarbonate, or phenol red. For copper treatment, HEK 293T cells were cultured as described above. One day prior to imaging, 100 µM $CuCl_2$ was added to cells from a 100 mM aqueous stock solution. Cells were then incubated at 37° C., 5% $CO_2$. After 10-12 hours, the media was exchanged for DPBS.

Flowcytometry Experiments.

Flowcytometry were performed with LSRFortessa™ cell analyzer (BD Biosciences) equipping 640 nm red laser and PE-Cy7 band pass filter. Cells were prepared as described above, and then 3-5 µM CS788 or CS790AM (from 1 mM stock solution in DMSO) was incubated at 37° C., 5% $CO_2$, for 15 min in DPBS. Bathocuproine disulfonate (BCS) was added to cells simultaneously with $CuCl_2$. Cells were washed by DPBS, and then 150 µL of trypsin-EDTA solution (1×, GIBCO) was added. After incubation at 37° C., 5% $CO_2$, for 5 min, 350 µL of DMEM containing 10% FBS was added to deactivate trypsin. To make sure complete removal of cells from coverslips, pipetting was repeated several times. The removed cells were collected to 1.5 mL eppendorf tube, and then the tubes were centrifuged (4000 rpm, 5 min). The supernatants were aspirated, and the cell pellets were suspended in 500 µL of DPBS containing 2% FBS. This process (suspension and centrifugation) was repeated 3 times. The washed cell pellets were suspended in 500 µL of DPBS, and they were kept on ice. Gating was performed based on untreated live control cells, and a minimum of 10,000 live cells was gated per sample. Measurements were performed on three independent samples for each of three tested conditions (−Cu/+Cu, −Cu+BCS/+Cu+BCS, −Cu+NS3'/+Cu+NS3'), with error bars representing the standard deviation of the mean. For chelator experiments, bathocuproine disulfonate (BCS, 200 µM) was added and incubated simultaneously with $CuCl_2$, and NS3' (100 µM) was added and incubated at the same time as CS788 or CS790AM. Data were processed with FACS-Diva software (BD Biosciences).

Cellular Fluorescence Imaging Experiments.

Confocal fluorescence images were acquired at the Molecular Imaging Center at the University of California, Berkeley. Imaging experiments were performed with a Zeiss LSM510 META/NLO Axioplan 2 laser scanning microscope and a 40× water-immersion objective lens. Excitation of the dye-loaded cells was carried out with an argon ion laser, and emission was collected using a META detection system. Excitation of Hoechst-3342 was carried out using a MaiTai two-photon laser at 780-nm pulses (36% laser power, mode-locked Ti:sapphire laser, Tsunami Spectra Physics) and emission was collected between 452-538 nm. A mixture of dye (1-2 µM, from 1 mM stock in DMSO) and Hoescht-3342 (1 µM) was incubated with live cell samples for 15 min at 37° C. under 5% $CO_2$. BCS (200 µM) was added to the cells at the same time with $CuCl_2$, and NS3' (100 µM from a 100 mM stock in DMSO) was added to the cells with the dye. Image analysis was performed in ImageJ.

Fluorescence Imaging Experiments in Living Mice.

Fluorescence images of mice were acquired using a Xenogen IVIS Spectrum instrument. SKH1 mice were obtained from Charles River Labs. Mice were single or group-housed on a 12:12 light-dark cycle at 22° C. with free access to food and water. SKH1 mice, aged 5-10 weeks, were anesthetized with isoflurane and injected with 1) DPBS (i.p., 100 µL), 2) $CuCl_2$ (i.p., 5 mg/kg in 50 µL of DPBS) and DBPS (i.p., 50 µL), 3) $CuCl_2$ (i.p., 5 mg/kg in 50 µL of DPBS) and ATN-224 (i.p., 5 mg/kg in 50 µL of DPBS), or 4) ATN-224 (i.p., 5 mg/kg in 50 µL of DPBS) and DBPS (i.p., 50 µL). 0-24 hours later, the mice were anesthetized with isoflurane and injected (i.p.) with DPBS (50 µL) or a dye (0.1 mM, 50 µL) and imaged immediately or up to 10 days later. All animal studies were approved and performed according to the guidelines of the Animal Care and Use Committee of the University of California, Berkeley.

Summary of Experimental Results

CS790AM and CS788: The data for CS790AM and CS788 indicate that both of these dyes have a large fluorescence increase in the near-infrared region of the electromagnetic spectrum in response to Cu(I). Both dyes also bind selectively to Cu(I) over other transition metals, alkali metals, and alkali earth metals. Furthermore, both dyes are insensitive to pH changes in the physiological pH range, and both demonstrate a 1 to 1 binding with Cu(I). The dyes also demonstrate an increased fluorescence in cells loaded with copper chloride, and this fluorescence increase is reduced with copper chelation. This indicates that the dyes are able to detect changes in copper levels in living cells. Additionally, imaging in living mice shows that the dyes can detect changes in copper levels in mice when mice are injected with copper chloride, a copper chelator, or a combination of both. Finally, fluorescence imaging in mice reveals that the dyes are able to detect endogenous levels of copper in the mice. This result suggests that these compounds will be extremely useful for imaging changes in copper levels that result from disease, aging, diet, drugs or other stimuli.

Tokyo Green-based Dyes (with the exception of TG-CNS4): The data from the Tokyo Green-based dyes indicate that these dyes have a large fluorescence increase in response to Cu(I) and a high selectivity for binding Cu(I) over other transition metals, alkali metals, and alkali earth metals. These dyes also bind Cu(I) very tightly and are generally not affected by physiological changes in pH. The Hill plots indicate that dyes also have one to one binding with Cu(I) with no cooperativity. Finally, cellular imaging demonstrates that the dyes can visualize fluctuations on copper in living cells.

The mice that we used for our in vivo experiments were injected with NIR fluorescent copper sensors intraperitoneally; however, signal from one of the sensors can be seen from all regions of the mice, including the brain. This suggests that this compound is able to enter the blood stream and travel throughout the entire body of the mice. This quality is especially important for studying models of disease such as heart disease and neurodegeneration because the copper sensor is able to reach the organs of interest (heart and brain) easily. Furthermore, the copper sensor can be used to monitor all regions of the body at the same time, and with the help of 3D imaging it could allow links to be made between copper's impact on separate organs in the same disease model. Furthermore, the signal from the fluorescent copper sensors does penetrate the skin of the mice, so surgery is not required to detect the fluorescent signal.

Example 6

Synthesis of an Exemplary Binding-Based Probe According to Formula 2 (Wherein $X^1$ is $Si(CH_3)_2$ Scheme. Synthesis of an exemplary binding-based probe according to Formula 2 (wherein $X^1$ is $Si(CH_3)_2$).

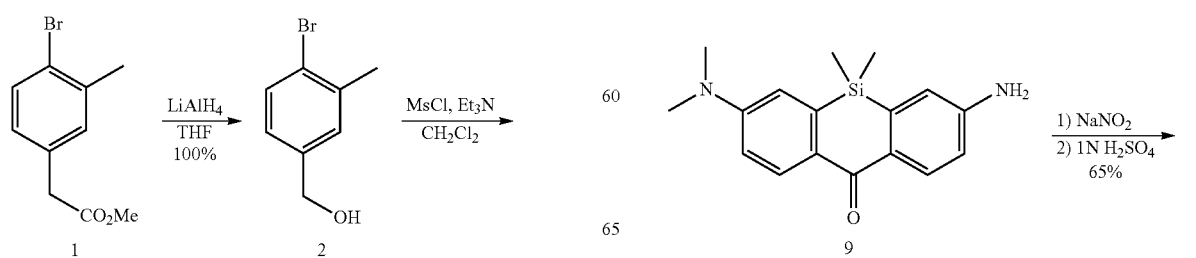

113
-continued

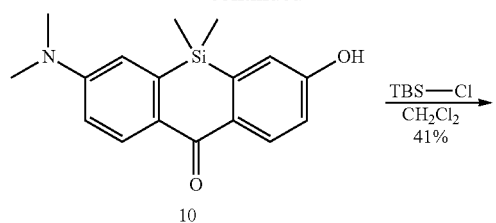

10

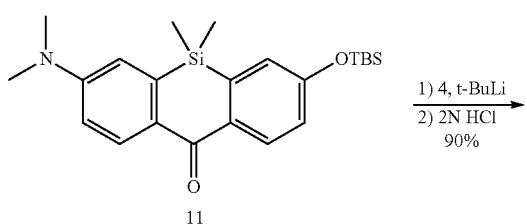

11

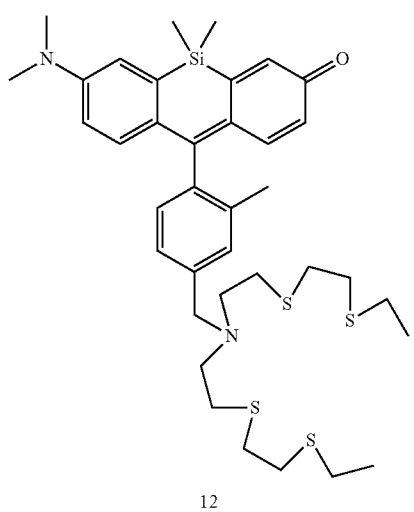

12

4-Bromo-5-methylbenzylalcohol (2)

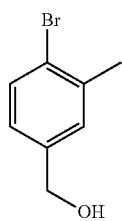

LiAlH₄ (1.75 g, 46 mmol) was added in portions to a stirred solution of 4-bromo-5-methylbenzoic acid (10 g, 46 mmol) in THF (100 mL) at 0° C. After 15 min, H₂O (50 mL) was added drop wise to the reaction which was then extracted with EtAOc (100 mL×3). The combined organic layers were washed with brine (200 mL×2), dried (Na₂SO₄), and concentrated under reduced pressure to yield compound 2 as a light yellow syrup (9.25 g, 46 mmol, 100% yield). ¹H NMR, (400 MHz, CDCl₃): δ 7.52 (d, J=8.2 Hz, 1H), 7.25 (d, J=2.4 Hz, 1H), 6.88-7.10 (m, 1H), 4.63 (s, 2H), 2.43 (s, 3H).

114
4-Bromo-3-methylbenzyl methanesulfonate (3)

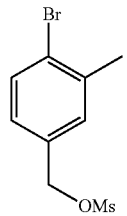

A solution of compound 2 (2.0 g, 9.95 mmol), Et₃N (6.94 mL, 49.7 mmol), and CH₂Cl₂ (100 mL) was cooled to 0° C. and treated with methanesulfonyl chloride (1.54 mL, 19.9 mmol). The solution was stirred at room temperature for 3 hours. The volatiles were removed under reduced pressure and the resultant crude product was used without further purification.

N-(4-Bromo-3-methylbenzyl)-3,6,12,15-tetrathia-9-monoazaheptadecane (4)

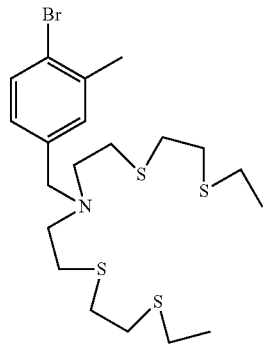 [SMILES: CCSCCSCCN(CCSCCSCC)Cc1ccc(Br)c(C)c1]

A solution of compound 3 (2.83 g, 10 mmol), NS₄' (6.27 g, 20 mmol), K₂CO₃ (5.53 g, 40 mmol), and KI (6.64 g, 40 mmol) in acetonitrile (250 mL) was stirred under nitrogen at reflux for 16 hours. The solvent was removed under reduced pressure and the crude residue was suspended in CH₂Cl₂. The organic fraction was washed with H₂O (50 mL×2), dried (Na₂SO₄), and concentrated under reduced pressure. The crude residue was purified via flash chromatography (1:9 v/v EtOAc/Hexanes) to yield compound 4 as a clear oil (2.21 g, 4.41 mmol, 45% yield over 2-steps). ¹H NMR (400 MHz, CDCl₃): δ 7.41 (d, J=8.0 Hz, 1H), 7.17 (s, 1H), 7.00 (d, J=8.0 Hz, 1H), 3.52 (s, 2H), 2.64 (m, 16H), 2.50 (q, J=7.4 Hz, 4H), 2.35 (s, 3H), 1.21 (t, J=7.4 Hz, 6H).

N,N-Diallyl-3-bromo-4-(2-bromo-4-(dimethylamino)benzyl)aniline (7)

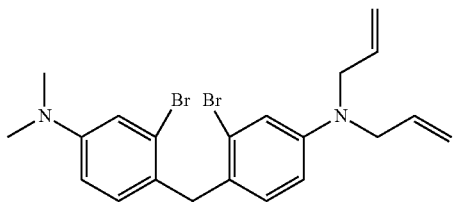 [SMILES: C=CCN(CC=C)c1ccc(Cc2ccc(N(C)C)cc2Br)c(Br)c1]

A solution of 3-bromo-N,N-dimethylaniline (7.54 g, 37.7 mmol) and 3-bromo-N,N-diallylaniline (9.51 g, 37.7 mmol) in glacial AcOH (250 mL) was treated with a 37 wt. % solution of formaldehyde in H$_2$O (30 mL). The resultant suspension was stirred at 80° C. for 2 h. After cooling to room temperature, the volatiles were removed under reduced pressure. The syrupy residue was dissolved in CH$_2$Cl$_2$ (100 mL), washed with sat. Na$_2$CO$_3$ (100 mL×2) and brine (100 mL), dried (Na$_2$SO$_4$), and concentrated under reduced pressure to afford a light brown syrup (16.9 g). $^1$H NMR analysis indicates that this mixture consists of approximately 30% the desired product. The inseparable mixture was used in the subsequent step without further purification. $^1$H NMR (400 MHz, CDCl$_3$): δ 6.91 (d, J=2.8 Hz, 2H), 6.82 (d, J=8.1 Hz, 2H), 6.55 (dd, J=2.8, 8.8 Hz, 2H), 5.78-5.87 (m, 2H), 5.14-5.20 (m, 4H), 3.98 (s, 2H), 3.85-3.87 (m, 4H), 3.15 (s, 6H).

3-Diallylamino-6-dimethylamino-Si-xanthone (8)

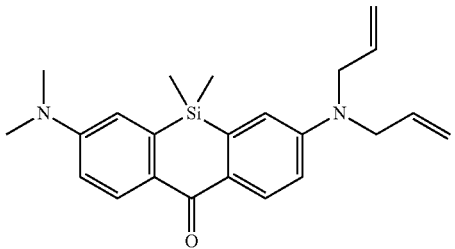 [SMILES: C=CCN(CC=C)c1ccc2c(c1)[Si](C)(C)c1cc(N(C)C)ccc1C2=O]

The mixture containing compound 7 (16.9 g) was dissolved in dry THF (200 mL), cooled to −78° C., and treated with a solution of sec-butyllithium in cyclohexane (1.4 M, 82 mL, 114.8 mmol). After stirring at the same temperature for 20 min, a solution of SiMe$_2$Cl$_2$ (7.39, 76.4 mmol) in dry THF (100 mL) was added drop wise. The mixture was warmed to room temperature and stirred for an additional 1 h. The reaction was quenched by addition of 2 N HCl, neutralized with sat. NaHCO$_3$, and extracted with CH$_2$Cl$_2$ (250 mL×3). The combined organic layers were washed with brine (250 mL), dried (Na$_2$SO$_4$), and concentrated under reduced pressure. The residue was dissolved in acetone (500 mL) and cooled to 0° C. Powered KMnO$_4$ (17.5 g, 111 mmol) was added in portions to the solution over 3 h. The reaction was diluted with CH$_2$Cl$_2$ (500 mL), filtered through a pad of celite, and concentrated under reduced pressure. The crude residue was purified via flash chromatography (100% CH$_2$Cl$_2$) to yield compound 8 as a yellow solid (750 mg, 2.0 mmol, 8% yield over 2-steps). $^1$H NMR (400 MHz, CDCl$_3$): δ 8.34 (d, J=8 Hz, 2H), 6.84-6.80 (m, 4H), 5.80-5.90 (m, 2H), 5.14-5.22 (m, 4H), 4.00-4.04 (m, 4H), 3.17 (s, 6H), 0.43 (s, 6H).

3-Amino-6-dimethylamino-Si-xanthone (9)

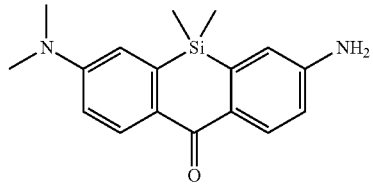 [SMILES: CN(C)c1ccc2c(c1)[Si](C)(C)c1cc(N)ccc1C2=O]

A flame-dried flask charged with compound 8 (160.4 mg, 0.43 mmol), Pd(PPh$_3$)$_4$ (64.4 mg, 0.06 mmol), 1,3-dimethylbarbituric acid (311 mg, 1.99 mmol), and CH$_2$Cl$_2$ (25 mL) was stirred overnight at 35° C. The volatiles were removed under reduced pressure and the resultant crude residue was purified via flash chromatography (1:1 v/v EtOAc/Hexanes) to yield compound 9 as a yellow solid (102 mg, 0.34 mmol, 80%. $^1$H NMR (400 MHz, MeOD): δ 8.15 (d, J=8.4 Hz, 2H), 6.88-6.78 (m, 4H), 3.10 (s, 6H), 0.41 (s, 6H).

3-Hydroxy-6-dimethylamino-Si-xanthone (10)

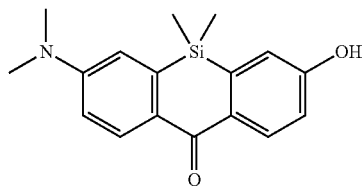 [SMILES: CN(C)c1ccc2c(c1)[Si](C)(C)c1cc(O)ccc1C2=O]

A solution of compound 9 (915 mg, 3.09 mmol) in MeOH (210 mL) and conc. H$_2$SO$_4$ (40 mL) was cooled to 0° C. and then treated with a solution of NaNO$_2$ (718 mg, 10.4 mmol) in H$_2$O (4.5 mL). The resultant mixture was stirred at 0° C. for 1 h and then added drop wise into boiling 1 N H$_2$SO$_4$ (500 mL). The resulting solution was refluxed for another 10 min, allowed to cool to room temperature, and extracted with CH$_2$Cl$_2$ (250 mL×3). The combined organic layers were washed with brine (250 mL), dried (Na$_2$SO$_4$), and concentrated under reduced pressure to afford compound 10 as a purple solid (596 mg, 2 mmol, 65% yield) which was used in the subsequent step without further purification. (400 MHz, MeOD): δ 8.25 (d, J=8.6 Hz, 2H), 7.10 (d, J=2.1 Hz, 2H), 6.94 (dd, J=2.1, 8.6 Hz, 2H), 3.15 (s, 6H), 0.44 (s, 6H).

3-(tert-Butyldimethylsilyloxy)-6-dimethylamino-Si-xanthone (11)

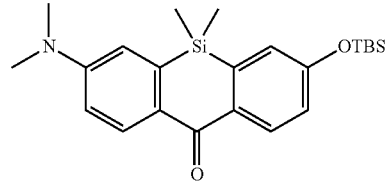 [SMILES: CN(C)c1ccc2c(c1)[Si](C)(C)c1cc(O)ccc1C2=O]

A solution of compound 10 (595 mg, 2.0 mmol) and imidazole (408.5 mg, 6.0 mmol) in CH$_2$Cl$_2$ (110 mL) was cooled to 0° C. and treated with tert-butyldimethylsilyl chloride (603 mg, 4.0 mmol). The reaction was stirred room temperature for 3 h and then poured into H$_2$O (25 mL). The organic phase was separated, washed with brine (25 mL), dried (Na$_2$SO$_4$), and concentrated under reduced pressure. The resultant residue was purified via flash chromatography (3:17 v/v EtOAc/Hexanes) to yield compound 11 as a pale yellow solid (333.5 mg, 0.81 mmol, 41% yield). (400 MHz, CDCl$_3$): δ 8.44 (t, J=8.8 Hz, 2H), 7.10 (d, J=2.0 Hz, 1H), 7.04 (dd, J=2.0, 8.8 Hz, 1H), 6.88 (dd, J=2.0, 8.8 Hz, 1H), 6.83 (d, J=2.0 Hz, 1H), 3.13 (s, 6H), 1.06 (s, 9H), 0.52 (s, 6H), 0.31 (s, 6H).

117

10-(4-((bis(2-(2-(ethylthio)ethylthio)ethyl)amino)methyl)-2-methylphenyl)-7-(dimethylamino)-5,5-dimethyldibenzo[b,e]silin-3(5H)-one (12)

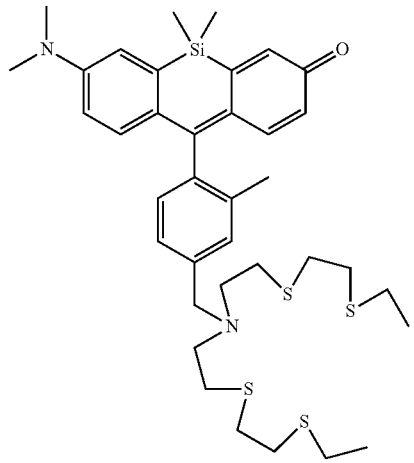 [SMILES: CCSCCSCCN(CCSCCSCC)Cc1ccc(C2=C3C=CC(=O)C=C3[Si](C)(C)c3cc(N(C)C)ccc32)c(C)c1]

An oven-dried 2-neck flask charged with compound 4 (88 mg, 0.18 mmol) and dry THF (1 mL) was cooled to −78° C. A solution of tert-butyllithium in pentane (1.7 M, 106 μL, 0.18 mmol) was added drop wise under nitrogen. After stirring at the same temperature for 10 mins, a solution of compound 11 (41.2 mg, 0.10 mmol) in dry THF (5 mL) was added. The resultant solution was warmed to room temperature and stirred for 60 mins. 2 N HCl (2 mL) was added and the reaction was stirred for a further 30 mins. The reaction was poured into sat. $NaHCO_3$ (10 mL) and extracted with EtOAc (10 mL×3). The combed organic layers were dried ($Na_2SO_4$) and concentrated under reduced pressure. The crude product was purified via flash chromatography (1:19 v/v MeOH/$CH_2Cl_2$) to yield compound 12 as a purple solid (41.8 mg, 0.06 mmol, 60% yield). (400 MHz, $CDCl_3$): δ 7.32 (m, 2H), 7.08 (d, J=7.6 Hz, 1H), 6.98-6.81 (m, 3H), 6.54 (dd, J=2.8, 9.2 Hz, 1H), 6.29 (d, J=10 Hz, 1H), 3.75 (s, 2H), 3.14 (s, 6H), 2.88-2.74 (m, 16H), 2.61 (q, J=7.6 Hz, 4H), 2.10 (s, 3H), 1.30 (t, J=7.2 Hz, 6H), 0.53 (s, 3H), 0.51 (s, 3H).

Example 7

Synthesis of Exemplary Binding-Based Probes According to Formulae 2 and 7 (Wherein $X^1$ is $C(R^{32})(R^{33})$)

Scheme. Synthesis of 3-(tert-Butyldimethylsilyloxy)-6-dialkamino-carbo-xanthone.

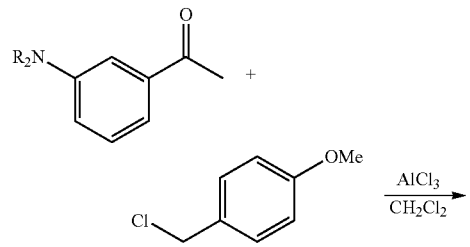

118

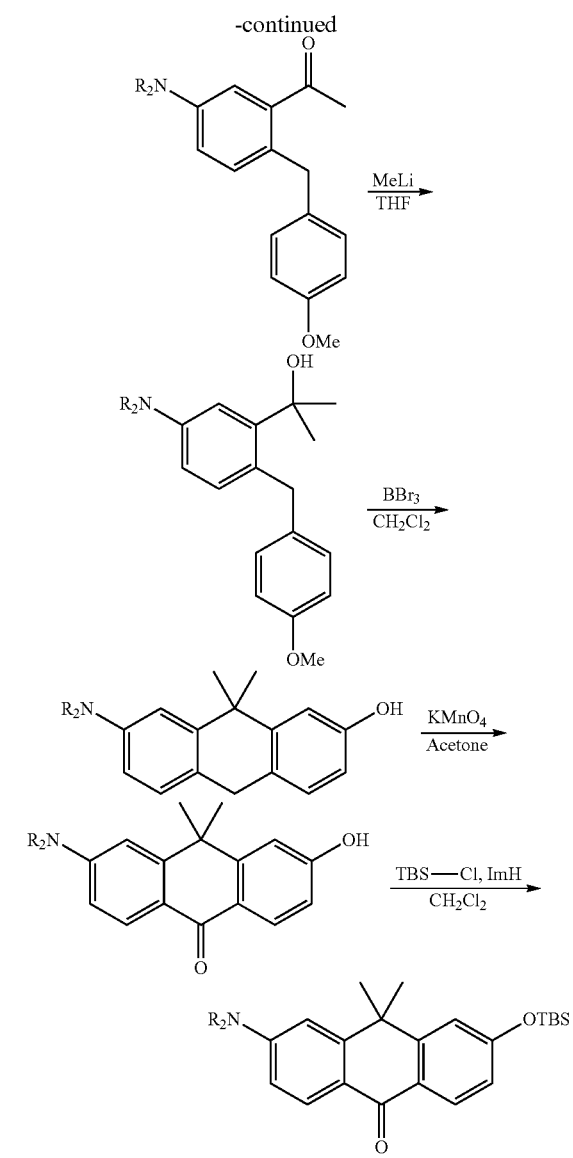

Scheme. Reaction between carbo-xanthones and the corresponding receptor moieties to afford exemplary compounds of Formulea 2 and 7.

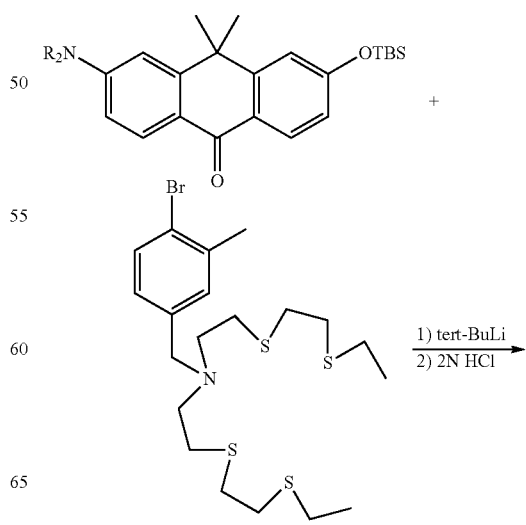

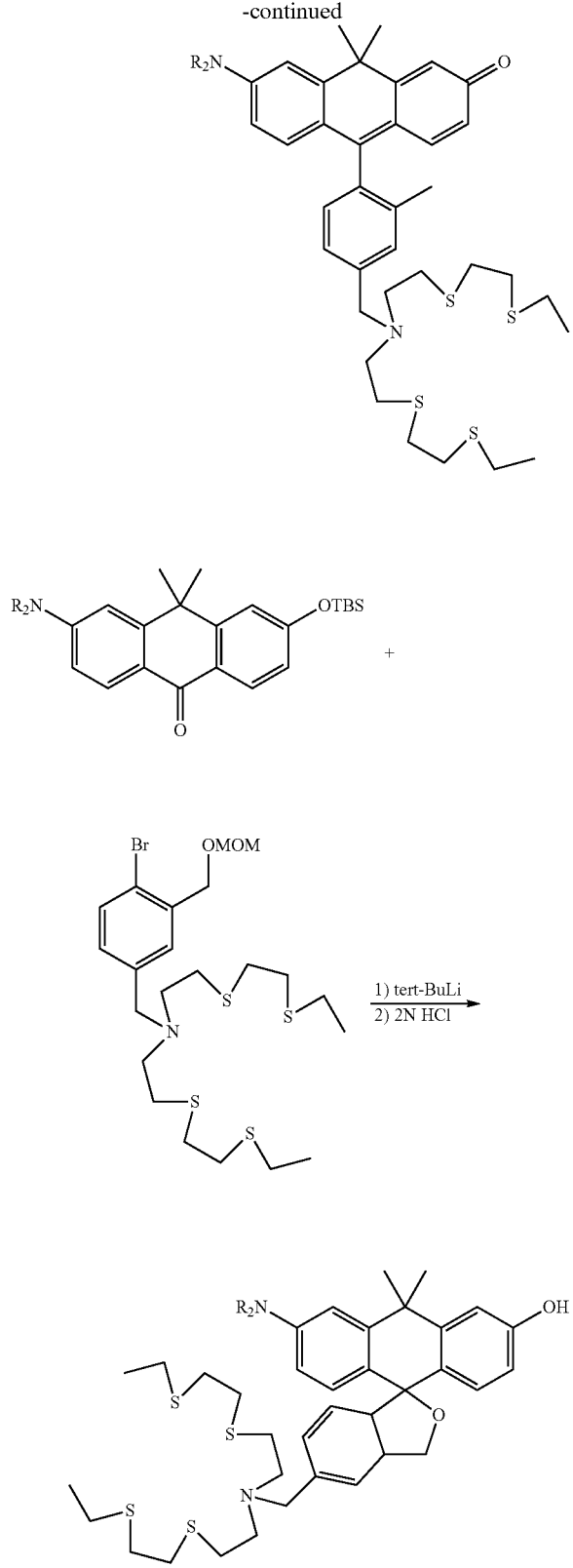
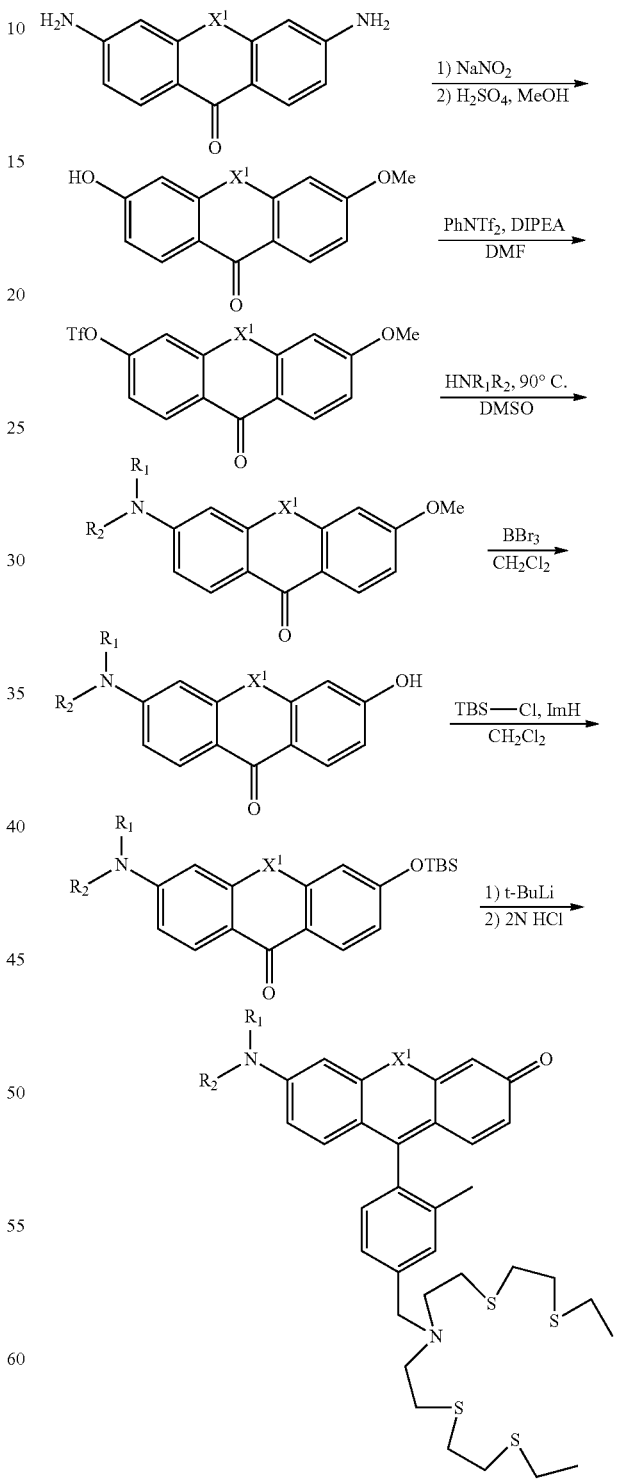
120
Example 8
Synthesis of Exemplary Binding-Based Probes According to Formula 2 (Wherein $X^1$ is $Sn(R^{32})(R^{33})$, $B(R^{32})(R^{33})$, S, Se, or Te)
Compounds according to Formula 2 and Formula 7, respectively, (wherein $X^1$ is $C(R^{32})(R^{33})$, such as $C(CH_3)_2$) can be synthesized according to the schemes above. $R^{32}$ and $R^{33}$ are as defined herein.
$X^1 = Sn(R^{32})(R^{33})$, $B(R^{32})(R^{33})$, S, Se, Te.

Compounds according to Formula 2 (wherein $X^1$ is $Sn(R^{32})(R^{33})$, $B(R^{32})(R^{33})$, S, Se, or Te) can be synthesized according to the scheme above. $R^{32}$ and $R^{33}$ are as defined herein.

The articles "a", "an" and "the" as used herein do not exclude a plural number of the referent, unless context clearly dictates otherwise. The conjunction "or" is not mutually exclusive, unless context clearly dictates otherwise. The term "include" is used to refer to non-exhaustive examples.

All references, publications, patent applications, issued patents, accession records and databases cited herein, including in any appendices, are incorporated by reference in their entirety for all purposes.

We claim:

1. A compound having the structure:

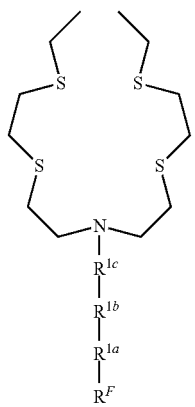

or a salt thereof,
wherein
$R^{1c}$ is a bond or —$CH_2$—;
$R^{1b}$ is a bond or unsubstituted aryl;
$R^{1a}$ is a bond or O; and
$R^F$ is selected from

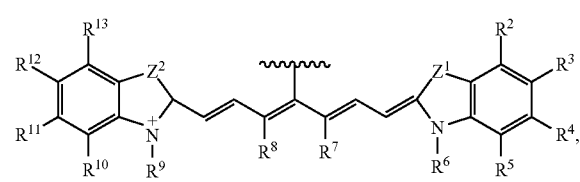

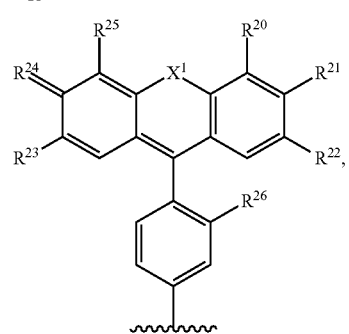

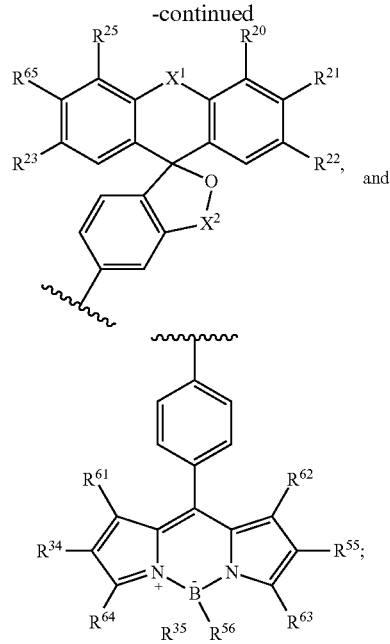

wherein $R^7$ and $R^8$ are independently selected from H, substituted or unsubstituted alkyl, and substituted or unsubstituted heteroalkyl;
wherein $R^7$ and $R^8$ that are independently selected from substituted or unsubstituted alkyl and substituted or unsubstituted heteroalkyl are optionally joined to form, along with the atoms to which they are attached, a substituted or unsubstituted cycloalkyl, substituted or unsubstituted heterocycloalkyl, substituted or unsubstituted aryl, or substituted or unsubstituted heteroaryl;
$Z^1$ is selected from S and —$C(R^{14})(R^{15})$—,
wherein $R^{14}$ and $R^{15}$ are independently selected from H, substituted or unsubstituted alkyl, and substituted or unsubstituted heteroalkyl;
$Z^2$ is selected from S and —$C(R^{50})(R^{51})$—,
wherein $R^{50}$ and $R^{51}$ are independently selected from H, substituted or unsubstituted alkyl, and substituted or unsubstituted heteroalkyl;
$R^2$, $R^3$, $R^4$, $R^5$, $R^{10}$, $R^{11}$, $R^{12}$, and $R^{13}$ are independently selected from H, —$SO_3H$, substituted or unsubstituted alkyl, and substituted or unsubstituted heteroalkyl;
wherein one or two of $R^2$, $R^3$, $R^4$, $R^5$, $R^{10}$, $R^{11}$, $R^{12}$, and $R^{13}$ are optionally —$SO_3H$; and
two of $R^2$, $R^3$, $R^4$, $R^5$, $R^{10}$, $R^{11}$, $R^{12}$, and $R^{13}$ that are adjacent and that are independently selected from substituted or unsubstituted alkyl and substituted or unsubstituted heteroalkyl are optionally joined to form, along with the atoms to which they are attached, a substituted or unsubstituted aryl or substituted or unsubstituted heteroaryl;
$Z^1$ and $R^2$ are optionally joined to form, along with the atoms to which they are attached, a substituted or unsubstituted aryl or substituted or unsubstituted heteroaryl;
$Z^2$ and $R^{13}$ are optionally joined to form, along with the atoms to which they are attached, a substituted or unsubstituted aryl or substituted or unsubstituted heteroaryl;
$R^6$ and $R^9$ are independently selected from substituted or unsubstituted alkyl and substituted or unsubstituted heteroalkyl;

$X^1$ is selected from O, Si($R^{32}$)($R^{33}$), C($R^{32}$)($R^{33}$), Sn($R^{32}$)($R^{33}$), B($R^{32}$)($R^{33}$), S, Se, and Te;
  wherein $R^{32}$ and $R^{33}$ are independently selected from H, substituted or unsubstituted alkyl, and substituted or unsubstituted heteroalkyl;
$R^{20}$, $R^{22}$, $R^{23}$, and $R^{25}$ are independently selected from H, halogen, —SO$_3$H, substituted or unsubstituted alkyl, and substituted or unsubstituted heteroalkyl;
$R^{21}$ is selected from —OR$^{27}$ and —NR$^{28}$R$^{29}$,
  wherein $R^{27}$ is selected from H, substituted or unsubstituted alkyl, substituted or unsubstituted heteroalkyl, —R$^{49}$—OR$^{42}$, —R$^{49}$—C(O)R$^{45}$, —R$^{49}$—C(O)OR$^{42}$, —R$^{49}$—C(O)N(R$^{43}$)R$^{44}$, and —R$^{49}$—N(R$^{43}$)C(O)R$^{45}$;
    wherein $R^{42}$, $R^{43}$, $R^{44}$, and $R^{45}$ are independently selected from H, substituted or unsubstituted alkyl, substituted or unsubstituted heteroalkyl, substituted or unsubstituted aryl, and substituted or unsubstituted heteroaryl; and
    $R^{49}$ is selected from a bond, substituted or unsubstituted alkyl, and substituted or unsubstituted heteroalkyl; and
  $R^{28}$ and $R^{29}$ are independently selected from H, substituted or unsubstituted alkyl, substituted or unsubstituted heteroalkyl, substituted or unsubstituted aryl, and substituted or unsubstituted heteroaryl;
  $R^{28}$ and $R^{29}$ are optionally joined to form, along with the atoms to which they are attached, a substituted or unsubstituted heterocycloalkyl;
  $R^{28}$ and $R^{20}$ are optionally joined to form, along with the atoms to which they are attached, a substituted or unsubstituted heterocycloalkyl;
  $R^{29}$ and $R^{22}$ are optionally joined to form, along with the atoms to which they are attached, a substituted or unsubstituted heterocycloalkyl;
$R^{24}$ is selected from O and NR$^{30}$R$^{31}$,
  wherein $R^{30}$ and $R^{31}$ are independently selected from H, substituted or unsubstituted alkyl, substituted or unsubstituted heteroalkyl, substituted or unsubstituted aryl, and substituted or unsubstituted heteroaryl;
    wherein $R^{30}$ and $R^{31}$ are optionally joined to form, along with the atoms to which they are attached, a substituted or unsubstituted heterocycloalkyl; and $R^{31}$ is optionally present;
  $R^{30}$ and $R^{25}$ or $R^{30}$ and $R^{23}$ are optionally joined to form, along with the atoms to which they are attached, a substituted or unsubstituted heterocycloalkyl;
  $R^{31}$ and $R^{23}$ are optionally joined to form, along with the atoms to which they are attached, a substituted or unsubstituted heterocycloalkyl;
$R^{26}$ is selected from H, —COOH, substituted or unsubstituted alkyl, and substituted or unsubstituted heteroalkyl;
$X^2$ is selected from —CH$_2$— and —C(O)—;
$R^{65}$ is selected from OR$^{68}$ and NR$^{66}$R$^{67}$,
  wherein $R^{66}$, $R^{67}$, and $R^{68}$ are independently selected from H, substituted or unsubstituted alkyl, substituted or unsubstituted heteroalkyl, substituted or unsubstituted aryl, and substituted or unsubstituted heteroaryl;
    wherein $R^{66}$ and $R^{67}$ are optionally joined to form, along with the atoms to which they are attached, a substituted or unsubstituted heterocycloalkyl;

$R^{34}$ is selected from H, substituted or unsubstituted alkyl, substituted or unsubstituted heteroalkyl, —CN, halogen, and

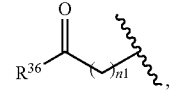

wherein $R^{36}$ is selected from H, substituted or unsubstituted alkyl, substituted or unsubstituted heteroalkyl, —OR$^{46}$, and —N(R$^{47}$)R$^{48}$,
    wherein $R^{46}$, $R^{47}$, and $R^{48}$ are independently selected from H, substituted or unsubstituted alkyl, and substituted or unsubstituted heteroalkyl; and
  n1 is an integer selected from 1, 2, 3, 4, 5, 6, 7, 8, 9, 10, 11, and 12;
$R^{55}$ is selected from H, substituted or unsubstituted alkyl, substituted or unsubstituted heteroalkyl, —CN, halogen, and

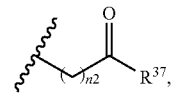

wherein $R^{37}$ is selected from H, substituted or unsubstituted alkyl, substituted or unsubstituted heteroalkyl, —OR$^{52}$, and —N(R$^{53}$)R$^{54}$,
    wherein $R^{52}$, $R^{53}$, and $R^{54}$ are independently selected from H, substituted or unsubstituted alkyl, and substituted or unsubstituted heteroalkyl; and
  n2 is an integer selected from 1, 2, 3, 4, 5, 6, 7, 8, 9, 10, 11, and 12;
$R^{35}$ is selected from halogen, substituted or unsubstituted alkyl, and substituted or unsubstituted heteroalkyl;
$R^{56}$ is selected from halogen, substituted or unsubstituted alkyl, and substituted or unsubstituted heteroalkyl;
$R^{61}$, $R^{62}$, $R^{63}$, and $R^{64}$ are independently selected from H, substituted or unsubstituted alkyl, substituted or unsubstituted alkenyl, substituted or unsubstituted aryl, and halogen;
$R^{63}$ and $R^{55}$ are optionally joined to form, along with the atoms to which they are attached, a ring selected from substituted or unsubstituted cycloalkyl, substituted or unsubstituted heterocycloalkyl, substituted or unsubstituted aryl, and substituted or unsubstituted heteroaryl; and
$R^{64}$ and $R^{34}$ are optionally joined to form, along with the atoms to which they are attached, a ring selected from substituted or unsubstituted cycloalkyl, substituted or unsubstituted heterocycloalkyl, substituted or unsubstituted aryl, and substituted or unsubstituted heteroaryl.

2. The compound or salt according to claim 1, having a structure selected from:

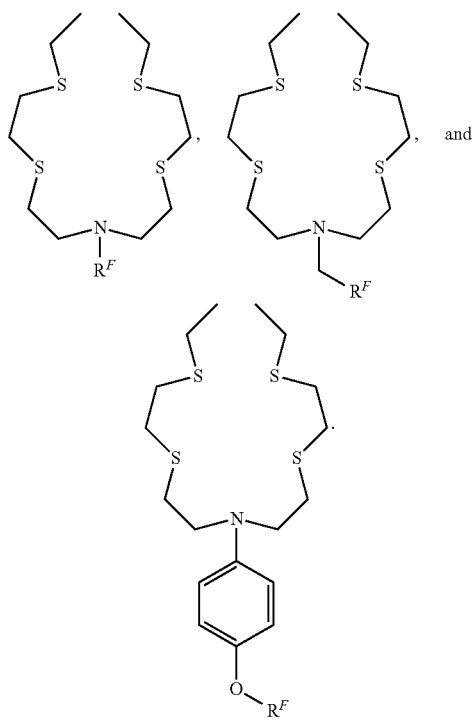

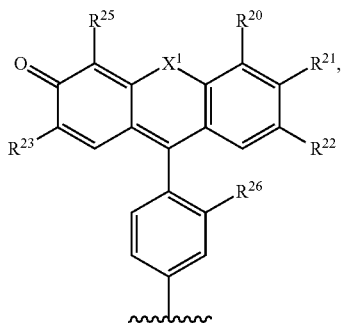

wherein
$R^{20}$, $R^{22}$, $R^{23}$, and $R^{25}$ are independently selected from H and unsubstituted alkyl;
$R^{21}$ is selected from —$OR^{27}$ and —$NR^{28}R^{29}$,
  wherein $R^{27}$ is H;
  $R^{28}$ and $R^{29}$ are independently selected from H, substituted or unsubstituted alkyl, substituted or unsubstituted heteroalkyl, substituted or unsubstituted aryl, and substituted or unsubstituted heteroaryl;
  $R^{28}$ and $R^{29}$ are optionally joined to form, along with the atoms to which they are attached, a substituted or unsubstituted heterocycloalkyl; and
$R^{26}$ is unsubstituted alkyl.

7. The compound or salt according to claim 1, wherein $R^F$ is

3. The compound or salt according to claim 1, wherein $R^F$ is

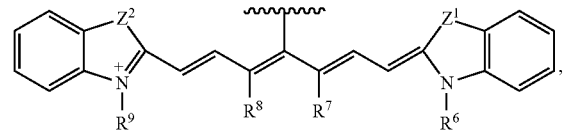

wherein
$R^7$ and $R^8$ are joined to form, along with the atoms to which they are attached, an unsubstituted cycloalkyl;
$Z^1$ is —$C(R^{14})(R^{15})$—,
  wherein $R^{14}$ and $R^{15}$ are unsubstituted alkyl; and
$Z^2$ is —$C(R^{50})(R^{51})$—,
  wherein $R^{50}$ and $R^{51}$ are unsubstituted alkyl.

4. The compound or salt according to claim 3, wherein $R^F$ is

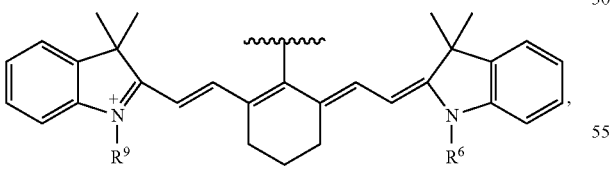

wherein
$R^6$ and $R^9$ are unsubstituted $C_1$ to $C_6$ alkyl; or
$R^6$ and $R^9$ are —$(CH_2)_mC(O)OR^{16}$,
  wherein m is an integer selected from 1, 2, 3, 4, 5, and 6; and
  $R^{16}$ is selected from H, and —$CH_2OC(O)CH_3$.

5. The compound or salt according to claim 4, wherein $R^6$ and $R^9$ are unsubstituted $C_1$ to $C_6$ alkyl.

6. The compound or salt according to claim 1, wherein $R^F$ is

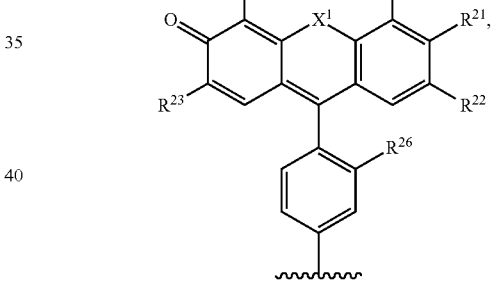

wherein
$X^1$ is selected from O, $Si(R^{32})(R^{33})$, and $C(R^{32})(R^{33})$,
  wherein $R^{32}$ and $R^{33}$ are unsubstituted alkyl;
$R^{20}$, $R^{22}$, $R^{23}$, and $R^{25}$ are independently selected from H and unsubstituted alkyl;
$R^{21}$ is selected from —$OR^{27}$ and —$NR^{28}R^{29}$,
  wherein $R^{27}$ is H;
  $R^{28}$ and $R^{29}$ are independently selected from H, substituted or unsubstituted alkyl, substituted or unsubstituted heteroalkyl, substituted or unsubstituted aryl, and substituted or unsubstituted heteroaryl;
  $R^{28}$ and $R^{29}$ are optionally joined to form, along with the atoms to which they are attached, a substituted or unsubstituted heterocycloalkyl; and
$R^{26}$ is unsubstituted alkyl.

8. The compound or salt according to claim 7, wherein
$X^1$ is selected from O, $Si(R^{32})(R^{33})$, and $C(R^{32})(R^{33})$,
  wherein $R^{32}$ and $R^{33}$ are methyl;
$R^{20}$, $R^{22}$, $R^{23}$, and $R^{25}$ are independently selected from H and methyl;
  wherein $R^{20}$ and $R^{25}$ are the same; and $R^{22}$ and $R^{23}$ are the same;

$R^{21}$ is selected from —OH,

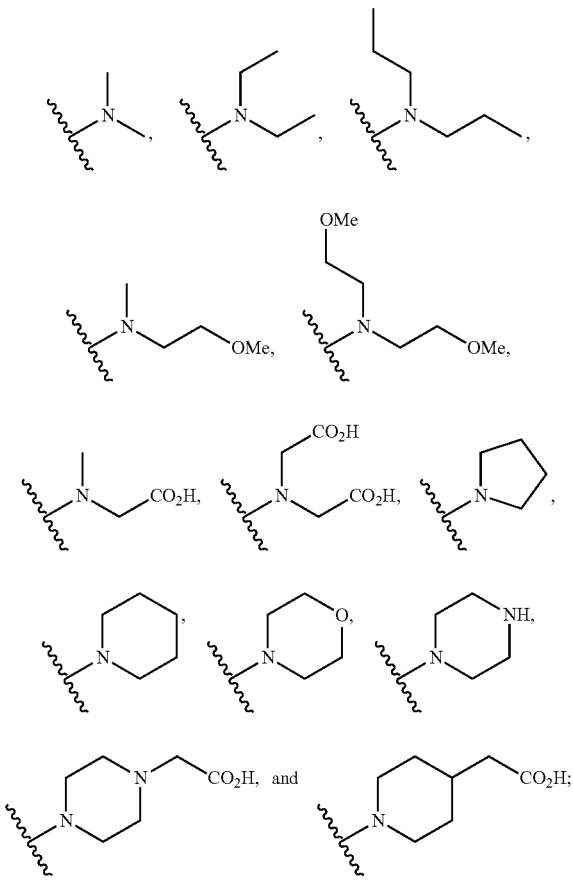

and $R^{26}$ is methyl.

9. The compound or salt according to claim 1, wherein $R^F$ is

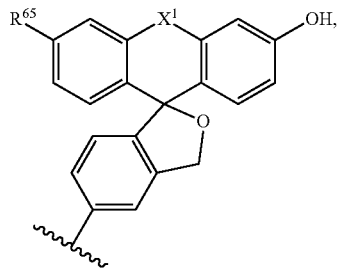

wherein $X^1$ is $C(R^{32})(R^{33})$,
  wherein $R^{32}$ and $R^{33}$ are unsubstituted alkyl; and
$R^{65}$ is $NR^{66}R^{67}$.

10. The compound or salt according to claim 9, wherein $R^{32}$ and $R^{33}$ are methyl.

11. The compound or salt according to claim 1, wherein $R^F$ is

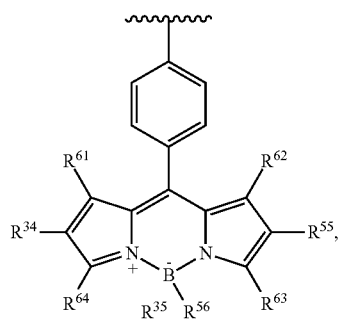

wherein
$R^{34}$ is unsubstituted alkyl;
$R^{55}$ is unsubstituted alkyl;
$R^{35}$ is unsubstituted heteroalkyl;
$R^{56}$ is unsubstituted heteroalkyl; and
$R^{61}$, $R^{62}$, $R^{63}$, and $R^{64}$ are unsubstituted alkyl.

12. The compound or salt according to claim 11, wherein
$R^{34}$ is unsubstituted $C_1$ to $C_6$ alkyl;
$R^{55}$ is unsubstituted $C_1$ to $C_6$ alkyl;
$R^{35}$ is unsubstituted $C_1$ to $C_6$ alkoxy;
$R^{56}$ is unsubstituted $C_1$ to $C_6$ alkoxy; and
$R^{61}$, $R^{62}$, $R^{63}$, and $R^{64}$ are unsubstituted $C_1$ to $C_6$ alkyl.

13. The compound or salt according to claim 1, wherein $R^F$ is selected from:

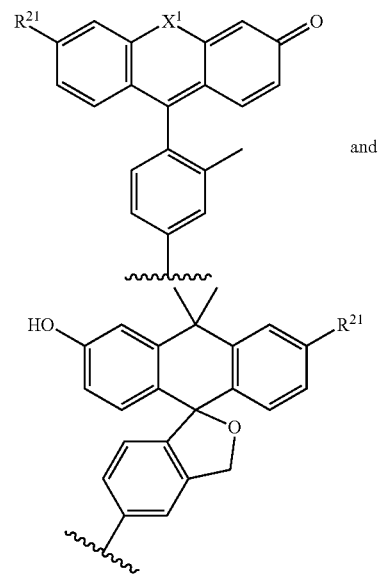

wherein
$X^1$ is selected from $C(CH_3)_2$, $Sn(R^{32})(R^{33})$, $B(R^{32})(R^{33})$, S, Se, and Te; and
$R^{21}$ is —$NR^{28}R^{29}$,
  wherein $R^{28}$ and $R^{29}$ are independently selected from H, substituted or unsubstituted alkyl, substituted or unsubstituted heteroalkyl, substituted or unsubstituted aryl, and substituted or unsubstituted heteroaryl;
  $R^{28}$ and $R^{29}$ are optionally joined to form, along with the atoms to which they are attached, a substituted or unsubstituted heterocycloalkyl.

14. The compound or salt according to claim 13, wherein said compound has a structure selected from:
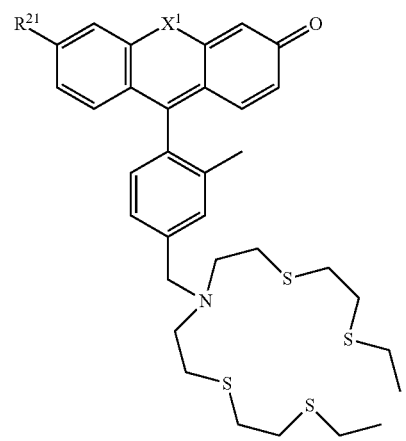
and
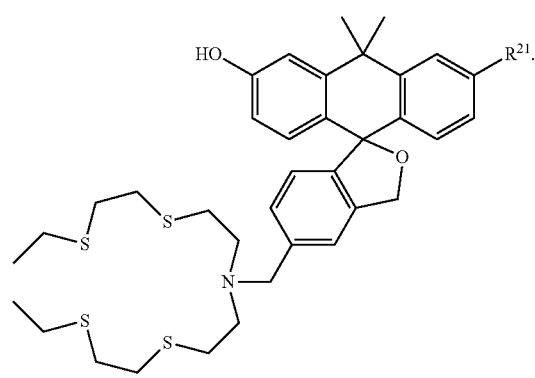
15. The compound or salt according to claim 1, wherein $R^F$ is selected from:
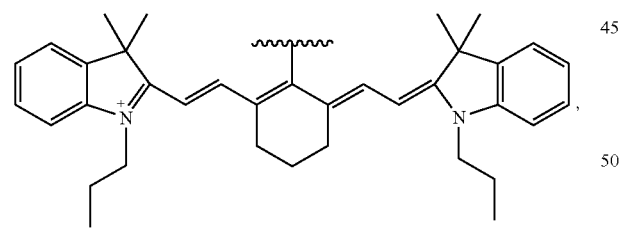
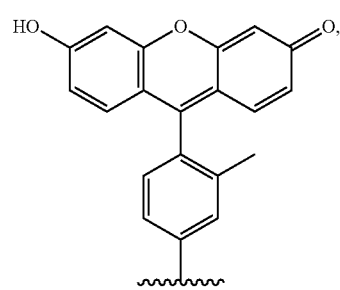
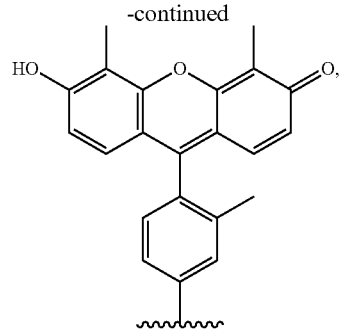
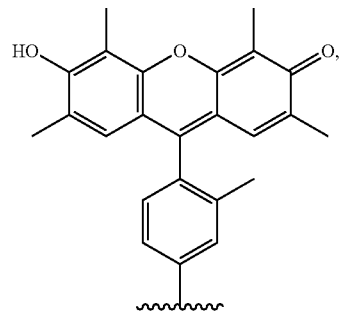
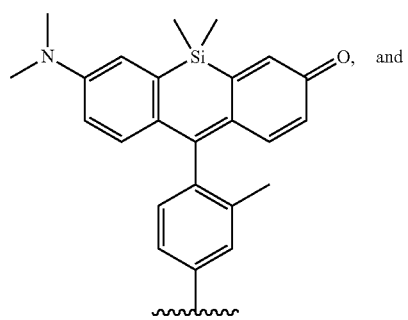
and
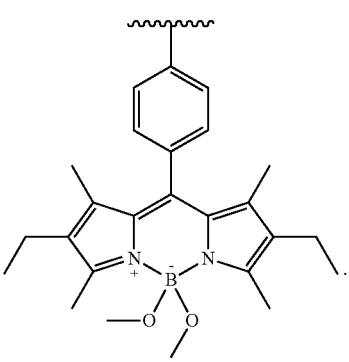
16. The compound or salt according to claim 15, wherein said compound has a structure selected from:

131
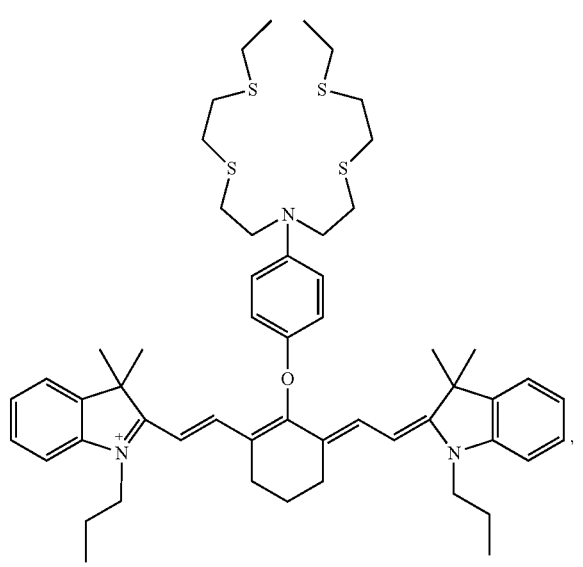
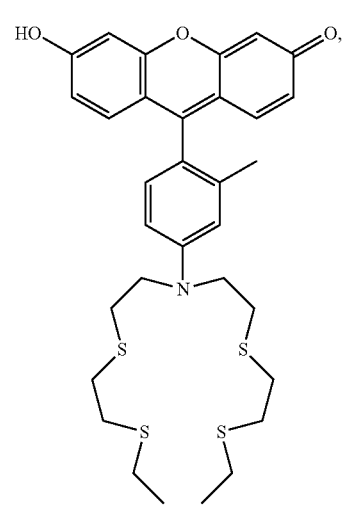
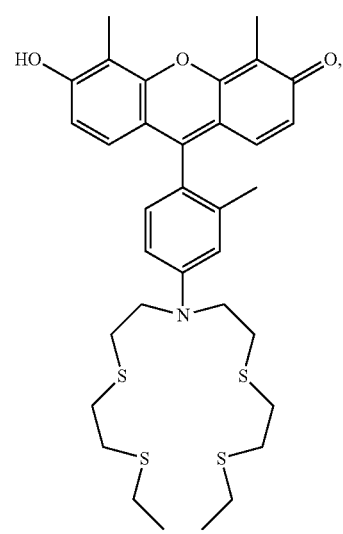
132
-continued
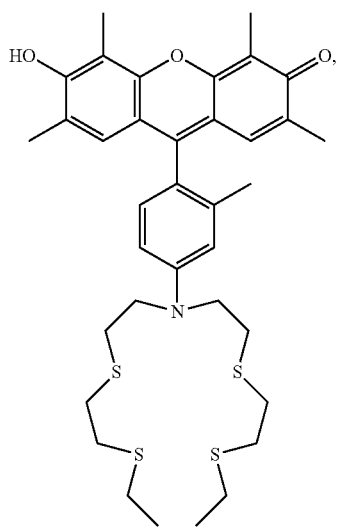
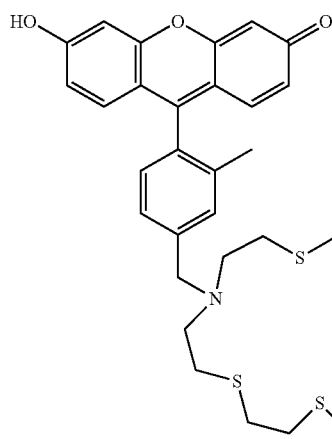
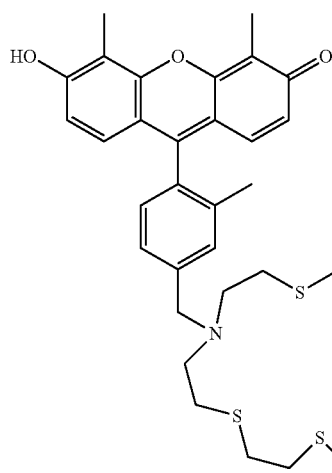

-continued

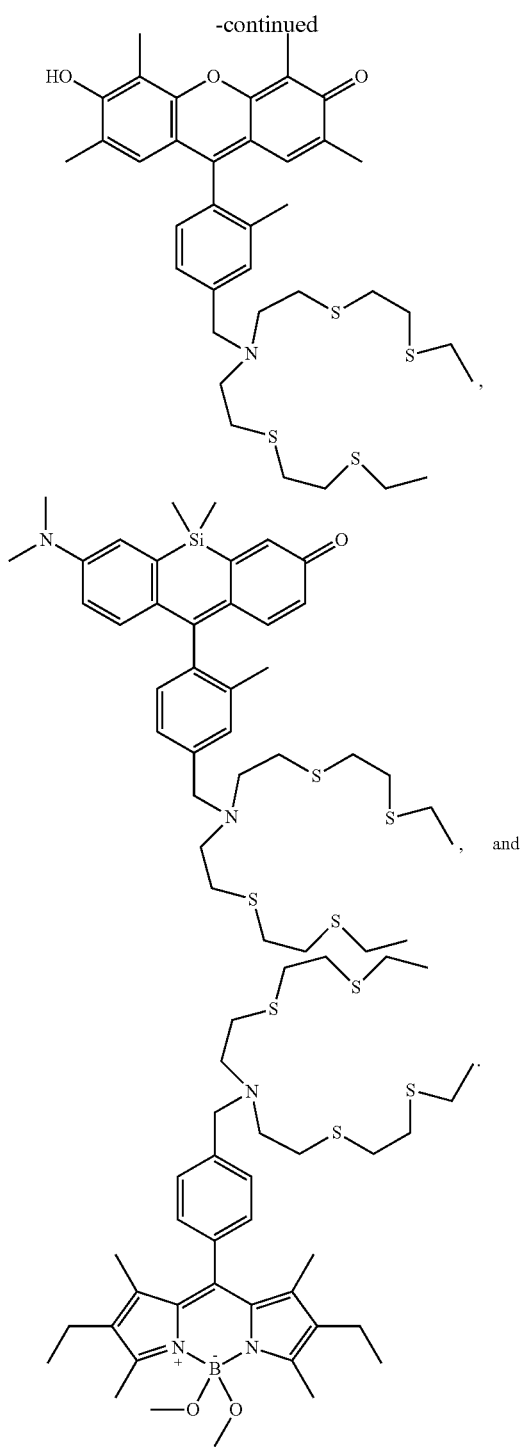

17. The compound or salt according to claim 1, wherein $R^F$ is

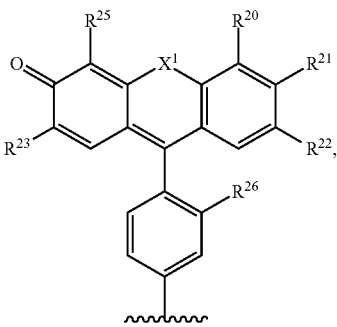

wherein $R^{20}$ $R^{22}$, $R^{23}$, and $R^{25}$ are independently selected from H and unsubstituted alkyl;

$R^{21}$ is selected from $-OR^{27}$ and $-NR^{28}R^{29}$, wherein $R^{27}$ is H;

$R^{28}$ and $R^{29}$ are independently selected from H, substituted or unsubstituted alkyl, substituted or unsubstituted heteroalkyl, substituted or unsubstituted aryl, and substituted or unsubstituted heteroaryl;

$R^{28}$ and $R^{29}$ are optionally joined to form, along with the atoms to which they are attached, a substituted or unsubstituted heterocycloalkyl; and $R^{26}$ is substituted alkyl.

18. The compound or salt according to claim 17, wherein $X^1$ is selected from O, $Si(R^{32})(R^{33})$, and $C(R^{32})(R^{33})$, wherein $R^{32}$ and $R^{33}$ are unsubstituted alkyl.

19. The compound or salt according to claim 17, wherein $R^{26}$ is selected from substituted $C_1$, $C_2$, $C_3$, $C_4$, $C_5$ and $C_6$ alkyl.

20. The compound or salt according to claim 17, wherein $R^{26}$ is alkyl substituted with one or more halogen.

* * * * *